US010039585B2

(12) United States Patent
Beyar et al.

(10) Patent No.: US 10,039,585 B2
(45) Date of Patent: Aug. 7, 2018

(54) METHODS, MATERIALS AND APPARATUS FOR TREATING BONE AND OTHER TISSUE

(75) Inventors: Mordechay Beyar, Caesarea (IL); Oren Globerman, Kfar-Shmaryahu (IL); Abraham Domb, Efrat (IL); Ronen Shavit, Tel-Aviv (IL); Hila Wachsler-Avrahami, Tel-Aviv (IL)

(73) Assignee: DePuy Synthes Products, Inc., Raynham, MA (US)

( * ) Notice: Subject to any disclaimer, the term of this patent is extended or adjusted under 35 U.S.C. 154(b) by 992 days.

(21) Appl. No.: 11/194,411

(22) Filed: Aug. 1, 2005

(65) Prior Publication Data

US 2006/0079905 A1    Apr. 13, 2006

Related U.S. Application Data

(63) Continuation-in-part of application No. PCT/IL2004/000527, filed on Jun. 17, 2004.
(Continued)

(30) Foreign Application Priority Data

Mar. 21, 2004   (IL) .......................................... 160987
Dec. 28, 2004   (IL) .......................................... 166017

(51) Int. Cl.
*A61F 2/28*       (2006.01)
*A61B 17/88*      (2006.01)
(Continued)

(52) U.S. Cl.
CPC ...... *A61B 17/8852* (2013.01); *A61B 17/7095* (2013.01); *A61B 17/8805* (2013.01);
(Continued)

(58) Field of Classification Search
CPC . A61B 17/8802; A61B 17/88; A61B 17/8805; A61B 17/8808; A61B 17/8816;
(Continued)

(56) References Cited

U.S. PATENT DOCUMENTS 229,932 A   7/1880   Witsil
370,335 A   9/1887   Hunter
(Continued)

FOREIGN PATENT DOCUMENTS

AU   724544   11/1996
AU   9865136   9/1998
(Continued)

OTHER PUBLICATIONS

Farrar, D.F. et al., "Rheological Properties of PMMA Bone Cements During Curing," Biomaterials 22:3005-13 (2001).
(Continued)

*Primary Examiner* — Paul Prebilic
(74) *Attorney, Agent, or Firm* — Nutter McClennen & Fish LLP

(57) ABSTRACT

A method of treating a vertebra, comprising:
(a) accessing an interior of a vertebra; and
(b) introducing a sufficient amount of artificial biocompatible material which does not set to a hardened condition in storage, into said bone, with sufficient force to move apart fractured portions of said bone.

12 Claims, 29 Drawing Sheets

Related U.S. Application Data

(60) Provisional application No. 60/592,149, filed on Jul. 30, 2004, provisional application No. 60/647,784, filed on Jan. 31, 2005, provisional application No. 60/654,495, filed on Feb. 22, 2005, provisional application No. 60/478,841, filed on Jun. 17, 2003, provisional application No. 60/529,612, filed on Dec. 16, 2003, provisional application No. 60/534,377, filed on Jan. 6, 2004, provisional application No. 60/554,558, filed on Mar. 18, 2004.

(51) Int. Cl.
*A61B 17/70* (2006.01)
*A61L 24/06* (2006.01)
*A61L 27/16* (2006.01)
*B01F 7/00* (2006.01)
*B01F 15/00* (2006.01)
*B01F 15/02* (2006.01)
*A61B 17/00* (2006.01)

(52) U.S. Cl.
CPC ...... *A61B 17/8811* (2013.01); *A61B 17/8816* (2013.01); *A61B 17/8822* (2013.01); *A61B 17/8833* (2013.01); *A61L 24/06* (2013.01); *A61L 27/16* (2013.01); *B01F 7/00416* (2013.01); *B01F 15/00006* (2013.01); *B01F 15/00058* (2013.01); *B01F 15/00883* (2013.01); *B01F 15/0279* (2013.01); *A61B 17/8819* (2013.01); *A61B 2017/00539* (2013.01); *A61B 2017/00734* (2013.01); *A61L 2400/06* (2013.01); *A61L 2430/38* (2013.01)

(58) Field of Classification Search
CPC ............ A61B 17/8811; A61B 17/8825; A61B 17/8822; A61B 17/3474; A61B 17/1728; A61B 17/1717; A61B 17/1721; A61B 17/1739–17/1767; A61B 2560/04; A61B 2560/0456
USPC .......................................... 606/92–94, 96–98
See application file for complete search history.

(56) References Cited

U.S. PATENT DOCUMENTS

| | | |
|---|---|---|
| 817,973 A | 4/1906 | Hausmann |
| 833,044 A | 10/1906 | Goodhugh |
| 843,587 A | 2/1907 | DePew |
| 1,175,530 A | 3/1916 | Kirchhoff |
| 1,612,281 A | 12/1926 | Goetz |
| 1,612,996 A | 1/1927 | Waagbo |
| 1,733,516 A | 10/1929 | Jamison |
| 1,894,274 A | 1/1933 | Jacques |
| 1,929,247 A | 10/1933 | Hein |
| 408,668 A | 4/1934 | Norman et al. |
| 2,123,712 A | 7/1938 | Clark |
| 2,283,915 A | 5/1942 | Cole |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Meyers et al. |
| 2,745,575 A | 5/1956 | Spencer |
| 2,773,500 A | 12/1956 | Young |
| 2,808,239 A | 10/1957 | Alfred |
| 2,874,877 A | 2/1959 | Spencer |
| 2,918,841 A | 12/1959 | Poupitch |
| 2,928,574 A | 3/1960 | Wagner |
| 2,970,773 A * | 2/1961 | Keryluk et al. ............ 239/142 |
| 3,058,413 A | 10/1962 | Cavalieri |
| 3,063,449 A | 11/1962 | Schultz |
| 3,075,746 A | 1/1963 | Yablonski et al. |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A * | 12/1965 | Di Cosola ..................... 606/94 |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,559,956 A | 2/1971 | Gray |
| 3,568,885 A | 3/1971 | Spencer |
| 3,572,556 A | 3/1971 | Pogacar |
| 3,605,745 A | 9/1971 | Hodosh |
| 3,615,240 A | 10/1971 | Sanz |
| 3,674,011 A | 7/1972 | Michel et al. |
| 3,701,350 A | 10/1972 | Guenther |
| 3,750,667 A | 8/1973 | Pshenichny et al. |
| 3,789,727 A | 2/1974 | Moran |
| 3,796,303 A | 3/1974 | Abbel-Coche |
| 3,798,982 A | 3/1974 | Lundquist |
| 3,846,846 A | 11/1974 | Fischer |
| 3,850,158 A | 11/1974 | Elias et al. |
| 3,867,728 A | 2/1975 | Stubstad et al. |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden et al. |
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildenbrandt et al. |
| 3,993,250 A | 11/1976 | Shure |
| 4,011,602 A | 3/1977 | Rybicki et al. |
| 4,062,274 A | 12/1977 | Knab |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | Dewijn |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,180,070 A | 12/1979 | Genese |
| 4,185,072 A | 1/1980 | Puderbaugh et al. |
| 4,189,065 A | 2/1980 | Herold |
| 4,198,383 A | 4/1980 | Konsetov et al. |
| 4,198,975 A | 4/1980 | Haller |
| 4,204,531 A | 5/1980 | Aginsky |
| 4,239,113 A | 12/1980 | Gross et al. |
| 4,250,887 A | 2/1981 | Dardik et al. |
| 4,257,540 A | 3/1981 | Wegmann et al. |
| 4,268,639 A | 5/1981 | Seidel et al. |
| 4,274,163 A * | 6/1981 | Malcom et al. ............... 606/94 |
| 4,276,878 A | 7/1981 | Storz |
| 4,277,184 A | 7/1981 | Solomon |
| 4,298,144 A | 11/1981 | Pressi |
| 4,309,777 A | 1/1982 | Patil |
| 4,312,343 A | 1/1982 | LaVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A * | 9/1983 | Scales ............................ 606/93 |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |

(56) References Cited

U.S. PATENT DOCUMENTS

| | | |
|---|---|---|
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Miller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilivie et al. |
| 4,642,099 A | 2/1987 | Phillips et al. |
| 4,650,469 A | 3/1987 | Berg et al. |
| 4,651,904 A | 3/1987 | Schuckman |
| 4,653,487 A | 3/1987 | Maale |
| 4,653,489 A | 3/1987 | Tronzo et al. |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Abjpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |
| 4,735,616 A | 4/1988 | Eibl et al. |
| 4,737,151 A | 4/1988 | Clement et al. |
| 4,747,832 A | 5/1988 | Buffet |
| 4,758,096 A | 7/1988 | Gunnarsson |
| 4,758,234 A | 7/1988 | Orentreich et al. |
| 4,759,769 A | 7/1988 | Hedman et al. |
| 4,762,515 A | 8/1988 | Grimm |
| 4,767,033 A | 8/1988 | Gemperle |
| 4,772,287 A | 9/1988 | Ray et al. |
| 4,782,118 A | 11/1988 | Fontanille et al. |
| 4,786,184 A | 11/1988 | Berezkina et al. |
| 4,791,150 A | 12/1988 | Braden et al. |
| 4,792,577 A | 12/1988 | Chen et al. |
| 2,067,458 A | 2/1989 | Nichols |
| 4,804,023 A | 2/1989 | Frearson |
| 4,813,870 A | 3/1989 | Pitzen |
| 4,815,454 A | 3/1989 | Dozier |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,854,716 A | 8/1989 | Ziemann et al. |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,973,301 A | 1/1990 | Nissenkorn |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenet |
| 4,968,303 A | 11/1990 | Clarke et al. |
| 4,969,888 A | 11/1990 | Scholten et al. |
| 4,973,168 A | 11/1990 | Chan |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioli et al. |
| 5,006,112 A | 4/1991 | Metzner |
| 5,012,066 A | 4/1991 | Matsutani et al. |
| 5,012,413 A | 4/1991 | Sroka et al. |
| 5,015,233 A | 5/1991 | McGough et al. |
| 5,018,919 A | 5/1991 | Stephan |
| 5,022,563 A | 6/1991 | Marchito et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,062,128 A | 10/1991 | Jahr et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |
| 5,102,413 A | 4/1992 | Poddar |
| 5,108,403 A | 4/1992 | Stern |
| 5,108,404 A | 4/1992 | Scholten et al. |
| 5,112,333 A | 5/1992 | Fixel |
| 5,114,240 A | 5/1992 | Kindt-Larsen et al. |
| 5,116,335 A | 5/1992 | Hannon |
| 5,122,400 A | 6/1992 | Stewart |
| 5,123,926 A | 6/1992 | Pisharodi |
| 5,125,971 A | 6/1992 | Nonami et al. |
| 5,131,382 A | 7/1992 | Meyer |
| 5,141,496 A | 8/1992 | Dalto et al. |
| 5,145,250 A | 9/1992 | Planck et al. |
| 5,147,903 A | 9/1992 | Podszun et al. |
| 5,171,248 A | 12/1992 | Ellis |
| 5,171,278 A | 12/1992 | Pisharodi |
| 5,181,918 A | 1/1993 | Brandhorst et al. |
| 5,188,259 A | 2/1993 | Petit |
| 5,190,191 A | 3/1993 | Reyman |
| 5,192,327 A | 3/1993 | Brantigan |
| 5,193,907 A | 3/1993 | Facciolli |
| 5,203,773 A | 4/1993 | Green |
| 5,209,753 A | 5/1993 | Biedermann et al. |
| 5,217,147 A | 6/1993 | Kaufman |
| 5,219,897 A | 6/1993 | Murray |
| 5,236,445 A | 8/1993 | Hayhurst et al. |
| 5,242,983 A | 9/1993 | Kennedy et al. |
| 5,252,301 A | 10/1993 | Nilson et al. |
| 5,254,092 A | 10/1993 | Polyak |
| 5,258,420 A | 11/1993 | Posey-Dowty et al. |
| 5,264,215 A | 11/1993 | Nakabayashi et al. |
| 5,268,001 A | 12/1993 | Nicholson et al. |
| 5,269,762 A | 12/1993 | Armbruster et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,290,260 A | 3/1994 | Stines |
| 5,295,980 A * | 3/1994 | Ersek .................. 604/272 |
| 5,302,020 A | 4/1994 | Kruse |
| 5,303,718 A | 4/1994 | Kajicek |

(56) References Cited

U.S. PATENT DOCUMENTS

| | | | |
|---|---|---|---|
| 5,304,147 A | 4/1994 | Johnson et al. | |
| 5,318,532 A * | 6/1994 | Frassica | 604/97.01 |
| 5,328,262 A | 7/1994 | Lidgren et al. | |
| 5,328,362 A | 7/1994 | Watson et al. | |
| 5,331,972 A | 7/1994 | Wadhwani et al. | |
| 5,333,951 A | 8/1994 | Wakoh | |
| 5,334,184 A | 8/1994 | Bimman | |
| 5,334,626 A | 8/1994 | Lin | |
| 5,336,699 A | 8/1994 | Cooke et al. | |
| 5,336,700 A | 8/1994 | Murray | |
| 5,344,232 A | 9/1994 | Nelson et al. | |
| 5,348,391 A | 9/1994 | Murray | |
| 5,348,548 A | 9/1994 | Meyer et al. | |
| 5,350,372 A | 9/1994 | Ikeda et al. | |
| 5,354,287 A | 10/1994 | Wacks | |
| 5,356,382 A | 10/1994 | Picha et al. | |
| 5,368,046 A | 11/1994 | Scarfone et al. | |
| 5,368,386 A | 11/1994 | Murray | |
| 5,370,221 A | 12/1994 | Magnusson et al. | |
| 5,372,583 A | 12/1994 | Roberts et al. | |
| 5,374,427 A | 12/1994 | Stille et al. | |
| 5,375,583 A | 12/1994 | Roberts | |
| 5,376,123 A | 12/1994 | Klaue et al. | |
| 5,380,772 A | 1/1995 | Hasegawa et al. | |
| 5,385,081 A | 1/1995 | Sneddon | |
| 5,385,566 A | 1/1995 | Ullmaerk | |
| 5,387,191 A | 2/1995 | Hemstreet et al. | |
| 5,390,683 A | 2/1995 | Pisharodi | |
| 5,395,167 A | 3/1995 | Murray | |
| 5,395,326 A | 3/1995 | Haber et al. | |
| 5,398,483 A | 3/1995 | Smith et al. | |
| 5,401,806 A | 3/1995 | Braden et al. | |
| 5,407,266 A | 4/1995 | Dotsch et al. | |
| 5,411,180 A | 5/1995 | Dumelle | |
| 5,415,474 A | 5/1995 | Nelson et al. | |
| 5,423,824 A | 6/1995 | Akerfeldt et al. | |
| 5,423,850 A | 6/1995 | Berger | |
| 5,431,654 A | 7/1995 | Nic | |
| 5,435,645 A | 7/1995 | Faccioli | |
| 5,441,502 A * | 8/1995 | Bartlett | 606/104 |
| 5,443,182 A | 8/1995 | Tanaka et al. | |
| 5,445,639 A | 8/1995 | Kuslich et al. | |
| 5,450,924 A | 9/1995 | Tseng | |
| 5,454,365 A | 10/1995 | Bonutti | |
| 5,456,267 A | 10/1995 | Stark | |
| 5,468,245 A | 11/1995 | Vargas, III | |
| 5,480,400 A | 1/1996 | Berger | |
| 5,480,403 A | 1/1996 | Lee | |
| 5,482,187 A | 1/1996 | Poulsen et al. | |
| 5,492,247 A | 2/1996 | Shu et al. | |
| 5,494,349 A | 2/1996 | Seddon | |
| 5,501,374 A * | 3/1996 | Laufer et al. | 222/391 |
| 5,501,520 A | 3/1996 | Lidgren et al. | |
| 5,501,695 A | 3/1996 | Anspach, Jr. et al. | |
| 5,512,610 A | 4/1996 | Lin | |
| 5,514,135 A | 5/1996 | Earle | |
| 5,514,137 A | 5/1996 | Coutts | |
| 5,518,498 A | 5/1996 | Lindenberg et al. | |
| 5,520,690 A | 5/1996 | Errico et al. | |
| 5,522,816 A | 6/1996 | Dinello et al. | |
| 5,522,899 A | 6/1996 | Michelson | |
| 5,526,853 A | 6/1996 | McPhee et al. | |
| 5,531,519 A | 7/1996 | Earle | |
| 5,531,683 A | 7/1996 | Kriesel et al. | |
| 5,534,028 A | 7/1996 | Bao et al. | |
| 5,536,262 A | 7/1996 | Velasquez | |
| 5,545,460 A | 8/1996 | Tanaka et al. | |
| 5,548,001 A | 8/1996 | Podszun et al. | |
| 5,549,380 A | 8/1996 | Lidgren et al. | |
| 5,549,381 A | 8/1996 | Hays et al. | |
| 5,549,679 A | 8/1996 | Kuslich | |
| 5,551,778 A | 9/1996 | Hauke et al. | |
| 5,554,101 A | 9/1996 | Matula et al. | |
| 5,556,201 A | 9/1996 | Veltrop et al. | |
| 5,558,136 A | 9/1996 | Orrico | |
| 5,558,639 A | 9/1996 | Gangemi et al. | |
| 5,571,189 A | 11/1996 | Kuslich et al. | |
| 5,573,265 A | 11/1996 | Pradel | |
| 5,578,035 A | 11/1996 | Lin | |
| 5,586,821 A | 12/1996 | Bonitati et al. | |
| 5,588,745 A | 12/1996 | Tanaka et al. | |
| 5,591,197 A | 1/1997 | Orth et al. | |
| 5,601,557 A | 2/1997 | Hayhurst | |
| 5,603,701 A | 2/1997 | Fisher | |
| 5,609,637 A | 3/1997 | Biedermann et al. | |
| 5,624,184 A | 4/1997 | Chan | |
| 5,630,806 A | 5/1997 | Inagaki et al. | |
| 5,634,880 A | 6/1997 | Feldman et al. | |
| 5,637,097 A | 6/1997 | Yoon | |
| 5,638,997 A | 6/1997 | Hawkins et al. | |
| 5,641,010 A | 6/1997 | Maier | |
| 5,645,598 A | 7/1997 | Brosnahan, III | |
| 5,647,856 A | 7/1997 | Eykmann | |
| 5,653,686 A | 8/1997 | Coulter et al. | |
| 5,658,310 A | 8/1997 | Berger | |
| 5,660,186 A | 8/1997 | Bachir | |
| 5,665,067 A | 9/1997 | Linder et al. | |
| 5,681,317 A | 10/1997 | Caldarise | |
| 5,683,451 A | 11/1997 | Lenker et al. | |
| 5,685,826 A | 11/1997 | Bonutti | |
| 5,690,606 A | 11/1997 | Slotman | |
| 5,693,100 A | 12/1997 | Pisharodi | |
| 5,697,977 A | 12/1997 | Pisharodi | |
| 5,698,611 A | 12/1997 | Okada et al. | |
| 5,702,448 A | 12/1997 | Buechel et al. | |
| 5,704,895 A | 1/1998 | Scott et al. | |
| 5,707,390 A | 1/1998 | Bonutti | |
| 5,718,707 A | 2/1998 | Mikhail | |
| 5,720,753 A | 2/1998 | Sander et al. | |
| 5,725,341 A | 3/1998 | Hofmeister | |
| 5,725,529 A | 3/1998 | Nicholson et al. | |
| 5,747,553 A | 5/1998 | Guzauskas | |
| 5,752,935 A | 5/1998 | Robinson et al. | |
| 5,752,969 A | 5/1998 | Cunci et al. | |
| 5,752,974 A | 5/1998 | Rhee | |
| 5,755,732 A | 5/1998 | Green et al. | |
| 5,759,186 A | 6/1998 | Bachmann et al. | |
| 5,763,092 A | 6/1998 | Lee et al. | |
| 5,779,356 A | 7/1998 | Chan | |
| 5,782,713 A | 7/1998 | Yang | |
| 5,782,747 A | 7/1998 | Zimmon | |
| 5,782,830 A | 7/1998 | Farris | |
| 5,782,838 A | 7/1998 | Beyar et al. | |
| 5,785,647 A | 7/1998 | Tompkins et al. | |
| 5,785,682 A | 7/1998 | Grabenkort | |
| 5,792,044 A | 8/1998 | Foley | |
| 5,795,922 A | 8/1998 | Demian et al. | |
| 5,797,678 A | 8/1998 | Murray | |
| 5,800,169 A | 9/1998 | Muhlbauer | |
| 5,800,409 A * | 9/1998 | Bruce | 604/523 |
| 5,800,549 A | 9/1998 | Bao et al. | |
| 5,800,550 A | 9/1998 | Sertich | |
| 5,820,321 A | 10/1998 | Gruber | |
| 5,824,087 A * | 10/1998 | Aspden et al. | 606/94 |
| 5,826,713 A | 10/1998 | Sunago et al. | |
| 5,826,753 A | 10/1998 | Fehlig et al. | |
| 5,827,217 A | 10/1998 | Silver et al. | |
| 5,827,289 A | 10/1998 | Reiley et al. | |
| 5,829,875 A | 11/1998 | Nagel et al. | |
| 5,830,194 A | 11/1998 | Anwar et al. | |
| 5,836,306 A * | 11/1998 | Duane et al. | 600/585 |
| 5,839,621 A | 11/1998 | Tada | |
| 5,842,785 A | 12/1998 | Brown et al. | |
| 5,842,786 A | 12/1998 | Solomon | |
| 5,865,802 A | 2/1999 | Yoon et al. | |
| 5,876,116 A | 3/1999 | Barker et al. | |
| 5,876,457 A | 3/1999 | Picha et al. | |
| 5,882,340 A | 3/1999 | Yoon et al. | |
| 5,884,818 A | 3/1999 | Campbell | |
| 5,893,488 A | 4/1999 | Hoag et al. | |
| 5,893,850 A | 4/1999 | Cachia | |
| 5,902,839 A | 5/1999 | Lautenschlager et al. | |
| 5,911,721 A | 6/1999 | Nicholson et al. | |
| 5,918,702 A | 7/1999 | Cheng et al. | |

(56) References Cited

U.S. PATENT DOCUMENTS

| | | | |
|---|---|---|---|
| 5,918,770 A | 7/1999 | Camm et al. | |
| 5,925,051 A | 7/1999 | Mikhail | |
| 5,928,239 A | 7/1999 | Mirza | |
| 5,931,347 A | 8/1999 | Haubrich | |
| 5,941,851 A | 8/1999 | Coffey et al. | |
| 5,954,671 A | 9/1999 | O'Neill | |
| 5,954,728 A | 9/1999 | Heller et al. | |
| 5,961,211 A | 10/1999 | Barker et al. | |
| 5,968,008 A | 10/1999 | Grams | |
| 5,968,044 A | 10/1999 | Nicholson et al. | |
| 5,968,999 A | 10/1999 | Ramp et al. | |
| 5,972,015 A | 10/1999 | Scribner et al. | |
| 5,980,527 A | 11/1999 | Cohen et al. | |
| 5,993,535 A | 11/1999 | Sawamura et al. | |
| 5,997,544 A | 12/1999 | Nies et al. | |
| 6,004,325 A | 12/1999 | Vargas, III | |
| 6,007,496 A | 12/1999 | Brannon | |
| 6,017,349 A | 1/2000 | Heller et al. | |
| 6,019,765 A | 2/2000 | Thornhill et al. | |
| 6,019,776 A | 2/2000 | Preissman et al. | |
| 6,019,789 A | 2/2000 | Dinh et al. | |
| 6,020,396 A | 2/2000 | Jacobs | |
| 6,022,339 A | 2/2000 | Fowles et al. | |
| 6,033,105 A | 3/2000 | Barker et al. | |
| 6,033,411 A | 3/2000 | Preissman | |
| 6,039,761 A | 3/2000 | Li et al. | |
| 6,040,408 A | 3/2000 | Koole | |
| 6,041,977 A | 3/2000 | Lisi | |
| 6,042,262 A | 3/2000 | Hajianpour | |
| 6,045,555 A | 4/2000 | Smith et al. | |
| 6,048,346 A | 4/2000 | Reiley | |
| 6,049,026 A | 4/2000 | Muschler | |
| 6,075,067 A | 6/2000 | Lidgren | |
| 6,080,579 A | 6/2000 | Hanley, Jr. | |
| 6,080,801 A | 6/2000 | Draenert et al. | |
| 6,080,811 A | 6/2000 | Schehlmann et al. | |
| 6,083,229 A | 7/2000 | Constantz et al. | |
| 6,086,594 A | 7/2000 | Brown | |
| 6,103,779 A | 8/2000 | Guzauskas | |
| 6,116,773 A | 9/2000 | Murray | |
| 6,120,174 A | 9/2000 | Hoag et al. | |
| 6,124,373 A * | 9/2000 | Peter et al. | 523/116 |
| 6,126,689 A | 10/2000 | Brett | |
| 6,127,597 A | 10/2000 | Beyar et al. | |
| 6,129,763 A | 10/2000 | Chauvin et al. | |
| 6,132,396 A | 10/2000 | Antanavich et al. | |
| 6,136,038 A | 10/2000 | Raab | |
| 6,139,509 A | 10/2000 | Yuan et al. | |
| 6,142,998 A | 11/2000 | Smith et al. | |
| 6,146,401 A | 11/2000 | Yoon et al. | |
| 6,149,651 A | 11/2000 | Drewry et al. | |
| 6,149,655 A | 11/2000 | Constantz et al. | |
| 6,149,664 A | 11/2000 | Kurz | |
| 6,160,033 A | 12/2000 | Nies | |
| 6,161,955 A | 12/2000 | Rademaker | |
| 6,168,597 B1 | 1/2001 | Biedermann et al. | |
| 6,174,935 B1 | 1/2001 | Matsunae et al. | |
| 6,176,607 B1 | 1/2001 | Hajianpour | |
| 6,183,441 B1 | 2/2001 | Kriesel et al. | |
| 6,183,516 B1 | 2/2001 | Burkinshaw et al. | |
| 6,187,015 B1 | 2/2001 | Brenneman | |
| 6,190,381 B1 | 2/2001 | Olsen et al. | |
| 6,206,058 B1 | 3/2001 | Nagel et al. | |
| 6,221,029 B1 | 3/2001 | Mathis et al. | |
| 6,210,031 B1 | 4/2001 | Murray | |
| 6,214,012 B1 | 4/2001 | Karpman et al. | |
| 6,214,016 B1 | 4/2001 | Williams et al. | |
| 6,214,037 B1 | 4/2001 | Mitchell et al. | |
| 6,217,566 B1 | 4/2001 | Ju et al. | |
| 6,217,581 B1 | 4/2001 | Tolson | |
| 6,217,608 B1 | 4/2001 | Penn et al. | |
| 6,224,604 B1 | 5/2001 | Suddaby | |
| 6,228,049 B1 | 5/2001 | Schroeder et al. | |
| 6,228,068 B1 | 5/2001 | Yoon | |
| 6,228,082 B1 | 5/2001 | Baker et al. | |
| 6,231,615 B1 | 5/2001 | Preissman | |
| 6,235,043 B1 | 5/2001 | Reiley et al. | |
| 6,238,399 B1 | 5/2001 | Heller et al. | |
| 6,241,734 B1 * | 6/2001 | Scribner et al. | 606/93 |
| 6,245,101 B1 | 6/2001 | Drasler et al. | |
| 6,248,110 B1 * | 6/2001 | Reiley et al. | 606/93 |
| 6,254,268 B1 | 7/2001 | Long | |
| 6,261,289 B1 | 7/2001 | Levy | |
| 6,264,618 B1 | 7/2001 | Landi et al. | |
| 6,264,659 B1 | 7/2001 | Ross et al. | |
| 6,264,660 B1 | 7/2001 | Schmidt et al. | |
| 6,273,916 B1 | 8/2001 | Murphy | |
| 6,281,271 B1 | 8/2001 | Rumphorst et al. | |
| 6,309,395 B1 | 10/2001 | Smith et al. | |
| 6,309,420 B1 | 10/2001 | Preissman | |
| 6,312,149 B1 | 11/2001 | Sjovall et al. | |
| 6,325,812 B1 | 12/2001 | Dubrul et al. | |
| 6,348,055 B1 | 2/2002 | Preissman | |
| 6,348,518 B1 | 2/2002 | Montgomery | |
| 6,350,271 B1 | 2/2002 | Kurz et al. | |
| 6,361,539 B1 | 3/2002 | Heller et al. | |
| 6,364,865 B1 | 4/2002 | Lavi et al. | |
| 6,367,962 B1 | 4/2002 | Mizutani et al. | |
| 6,375,659 B1 | 4/2002 | Erbe et al. | |
| 6,375,682 B1 | 4/2002 | Fleischmann et al. | |
| 6,383,188 B2 | 5/2002 | Kuslich et al. | |
| 6,383,190 B1 | 5/2002 | Preissman | |
| 6,395,007 B1 | 5/2002 | Bhatnagar | |
| 6,402,701 B1 | 6/2002 | Kaplan et al. | |
| 6,402,758 B1 | 6/2002 | Tolson | |
| 6,406,175 B1 | 6/2002 | Marino | |
| 6,409,972 B1 | 6/2002 | Chan | |
| 6,410,612 B1 | 6/2002 | Hatanaka | |
| 6,425,885 B1 | 7/2002 | Fischer et al. | |
| 6,425,887 B1 | 7/2002 | McGuckin et al. | |
| 6,431,743 B1 | 8/2002 | Mizutani et al. | |
| 6,433,037 B1 | 8/2002 | Guzauskas | |
| 6,436,143 B1 * | 8/2002 | Ross et al. | 623/17.16 |
| 6,439,439 B1 | 8/2002 | Rickard et al. | |
| 6,443,334 B1 | 9/2002 | John et al. | |
| 6,447,478 B1 | 9/2002 | Maynards | |
| 6,450,973 B1 | 9/2002 | Murphy | |
| 6,458,117 B1 | 10/2002 | Pollins, Sr. | |
| 6,479,565 B1 | 11/2002 | Stanley | |
| 6,488,667 B1 | 12/2002 | Murphy | |
| 6,494,868 B2 * | 12/2002 | Amar | 604/273 |
| 6,500,182 B2 | 12/2002 | Foster | |
| 6,502,608 B1 | 1/2003 | Burchett et al. | |
| 6,527,144 B2 | 3/2003 | Ritsche et al. | |
| 6,550,957 B2 | 4/2003 | Mizutani et al. | |
| 6,554,833 B2 | 4/2003 | Levy et al. | |
| 6,568,439 B1 | 5/2003 | Se et al. | |
| 6,572,256 B2 | 6/2003 | Seaton et al. | |
| 6,575,331 B1 | 6/2003 | Peeler et al. | |
| 6,575,919 B1 * | 6/2003 | Reiley et al. | 600/567 |
| 6,582,439 B1 | 6/2003 | Sproul | |
| 6,592,559 B1 | 7/2003 | Pakter et al. | |
| 6,595,967 B2 * | 7/2003 | Kramer | 604/264 |
| 6,599,293 B2 | 7/2003 | Tague et al. | |
| 6,599,520 B2 | 7/2003 | Scarborough et al. | |
| 6,613,018 B2 | 9/2003 | Bagga | |
| 6,613,054 B2 | 9/2003 | Scribner et al. | |
| 6,626,912 B2 | 9/2003 | Speitling | |
| 6,641,587 B2 | 11/2003 | Scribner et al. | |
| 6,645,213 B2 | 11/2003 | Sand et al. | |
| 6,662,969 B2 | 12/2003 | Peeler et al. | |
| 6,676,664 B1 | 1/2004 | Al-Assir | |
| 6,689,823 B1 | 2/2004 | Bellare et al. | |
| 6,702,455 B2 | 3/2004 | Vendrely et al. | |
| 6,712,853 B2 | 3/2004 | Kuslich | |
| 6,716,216 B1 | 4/2004 | Boucher et al. | |
| 6,719,761 B1 | 4/2004 | Reiley et al. | |
| 6,720,417 B1 | 4/2004 | Walter | |
| 6,730,095 B2 | 5/2004 | Olson, Jr. et al. | |
| 6,752,180 B2 | 6/2004 | Delay | |
| 6,758,837 B2 | 7/2004 | Peciat et al. | |
| 6,759,449 B2 | 7/2004 | Kimura et al. | |
| 6,767,973 B2 | 7/2004 | Suau et al. | |
| 6,770,079 B2 | 8/2004 | Bhatnagar | |

(56) References Cited

U.S. PATENT DOCUMENTS

| | | |
|---|---|---|
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 | 4/2005 | Foster |
| 6,875,219 B2 | 4/2005 | Arramon et al. |
| 6,887,246 B2 | 5/2005 | Bhatnagar |
| 6,916,308 B2 | 7/2005 | Dixon et al. |
| 6,957,747 B2 | 10/2005 | Peeler et al. |
| 6,974,247 B2 | 12/2005 | Frei et al. |
| 6,974,416 B2 | 12/2005 | Booker et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1* | 2/2006 | Jaggi et al. .................. 606/93 |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2* | 8/2006 | McGuckin et al. .......... 604/158 |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,264,622 B2 | 9/2007 | Michelson |
| 7,270,667 B2 | 9/2007 | Faccioli |
| 7,278,778 B2 | 10/2007 | Sand |
| 7,320,540 B2 | 1/2008 | Coffeen |
| 7,326,203 B2 | 2/2008 | Papineau et al. |
| 7,456,024 B2 | 11/2008 | Dahm et al. |
| 7,470,258 B2 | 12/2008 | Barker et al. |
| 7,559,932 B2 | 7/2009 | Truckai et al. |
| 7,572,263 B2 | 8/2009 | Preismann |
| 7,604,618 B2 | 10/2009 | Dixon et al. |
| 7,666,205 B2 | 2/2010 | Weikel et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 8,038,682 B2 | 10/2011 | McGill et al. |
| 8,066,713 B2 | 11/2011 | DiMauro et al. |
| 8,070,753 B2 | 12/2011 | Truckai et al. |
| 8,333,773 B2 | 12/2012 | DiMauro et al. |
| 8,360,629 B2 | 1/2013 | Globerman et al. |
| 8,361,078 B2 | 1/2013 | Beyar et al. |
| 8,415,407 B2 | 4/2013 | Beyar et al. |
| 8,540,722 B2* | 9/2013 | Beyar et al. .................. 606/94 |
| 8,809,418 B2 | 8/2014 | Beyar et al. |
| 8,950,929 B2 | 2/2015 | Globerman et al. |
| 8,956,368 B2 | 2/2015 | Beyar et al. |
| 9,186,194 B2 | 11/2015 | Ferreyro et al. |
| 9,259,696 B2 | 2/2016 | Globerman et al. |
| 9,381,024 B2 | 7/2016 | Globerman et al. |
| 9,504,508 B2 | 11/2016 | Beyar et al. |
| 9,642,932 B2 | 5/2017 | Beyar et al. |
| 9,750,840 B2 | 9/2017 | Beyar et al. |
| 9,839,460 B2 | 12/2017 | DiMauro et al. |
| 2001/0012968 A1 | 8/2001 | Preissman |
| 2001/0024400 A1 | 9/2001 | Van Der Wel |
| 2001/0034527 A1 | 10/2001 | Scribner et al. |
| 2002/0008122 A1 | 1/2002 | Ritsche et al. |
| 2002/0010471 A1 | 1/2002 | Wironen |
| 2002/0010472 A1 | 1/2002 | Kuslich et al. |
| 2002/0013553 A1 | 1/2002 | Pajunk |
| 2002/0099385 A1 | 1/2002 | Ralph et al. |
| 2002/0049448 A1 | 4/2002 | Sand et al. |
| 2002/0049449 A1* | 4/2002 | Bhatnagar et al. ........... 606/94 |
| 2002/0058947 A1* | 5/2002 | Hochschuler et al. ........ 606/94 |
| 2002/0067658 A1 | 6/2002 | Vendrely et al. |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0082605 A1 | 6/2002 | Reiley et al. |
| 2002/0099384 A1* | 7/2002 | Scribner et al. .............. 606/92 |
| 2002/0118595 A1 | 8/2002 | Miller |
| 2002/0123716 A1 | 9/2002 | VanDiver et al. |
| 2002/0156483 A1* | 10/2002 | Voellmicke et al. .......... 606/93 |
| 2002/0161373 A1 | 10/2002 | Osorio et al. |
| 2002/0177866 A1 | 11/2002 | Weikel et al. |
| 2002/0183851 A1 | 12/2002 | Spiegelberg et al. |
| 2002/0188300 A1 | 12/2002 | Arramon |
| 2002/0191487 A1 | 12/2002 | Sand |
| 2003/0009177 A1 | 1/2003 | Middleman et al. |
| 2003/0018339 A1 | 1/2003 | Higueras et al. |
| 2003/0031698 A1 | 2/2003 | Roeder et al. |
| 2003/0032929 A1 | 2/2003 | McGuckin et al. |
| 2003/0036763 A1 | 2/2003 | Bhatnager et al. |
| 2003/0040718 A1 | 2/2003 | Keahey et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 | 10/2003 | Vendrely et al. |
| 2003/0220414 A1 | 11/2003 | Axen et al. |
| 2003/0225364 A1 | 12/2003 | Kraft et al. |
| 2003/0227816 A1 | 12/2003 | Okamoto et al. |
| 2003/0231545 A1 | 12/2003 | Seaton |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0066706 A1 | 4/2004 | Barker et al. |
| 2004/0068264 A1* | 4/2004 | Treace ............................ 606/86 |
| 2004/0073139 A1 | 4/2004 | Hirsch et al. |
| 2004/0080357 A1 | 4/2004 | Chuang et al. |
| 2004/0092946 A1 | 5/2004 | Bagga et al. |
| 2004/0098015 A1 | 5/2004 | Weikel et al. |
| 2004/0106913 A1 | 6/2004 | Eidenschink et al. |
| 2004/0122438 A1 | 6/2004 | Abrams |
| 2004/0132859 A1 | 7/2004 | Puckett, Jr. et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1 | 8/2004 | Soffiati et al. |
| 2004/0157954 A1 | 8/2004 | Imai et al. |
| 2004/0162559 A1 | 8/2004 | Arramon et al. |
| 2004/0167532 A1 | 8/2004 | Olson et al. |
| 2004/0167562 A1 | 8/2004 | Osorio et al. |
| 2004/0167625 A1 | 8/2004 | Beyar et al. |
| 2004/0193171 A1 | 9/2004 | DiMauro |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm |
| 2005/0015148 A1 | 1/2005 | Jansen et al. |
| 2005/0025622 A1 | 2/2005 | Djeridane et al. |
| 2005/0058717 A1 | 3/2005 | Yetlinler |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1 | 3/2005 | Mazzuca |
| 2005/0083782 A1 | 4/2005 | Gronau et al. |
| 2005/0113762 A1* | 5/2005 | Kay et al. .................... 604/181 |
| 2005/0143827 A1 | 6/2005 | Globerman et al. |
| 2005/0154081 A1 | 7/2005 | Yin et al. |
| 2005/0159724 A1 | 7/2005 | Enerson |

(56) References Cited

U.S. PATENT DOCUMENTS

| | | |
|---|---|---|
| 2005/0180806 A1 | 8/2005 | Green |
| 2005/0203206 A1 | 9/2005 | Trieu |
| 2005/0209695 A1 | 9/2005 | de Vries et al. |
| 2005/0216025 A1 | 9/2005 | Chern Lin et al. |
| 2005/0256220 A1 | 11/2005 | Lavergne et al. |
| 2005/0281132 A1 | 12/2005 | Armstrong et al. |
| 2006/0035997 A1 | 2/2006 | Orlowski et al. |
| 2006/0041033 A1 | 2/2006 | Bisig et al. |
| 2006/0052794 A1 | 3/2006 | McGill |
| 2006/0074433 A1 | 4/2006 | McGill et al. |
| 2006/0079905 A1 | 4/2006 | Beyar et al. |
| 2006/0116643 A1 | 6/2006 | Dixon et al. |
| 2006/0116689 A1 | 6/2006 | Albans et al. |
| 2006/0116690 A1 | 6/2006 | Pagano |
| 2006/0122614 A1 | 6/2006 | Truckai et al. |
| 2006/0148923 A1 | 7/2006 | Ashman et al. |
| 2006/0164913 A1 | 7/2006 | Arramon |
| 2006/0167148 A1 | 7/2006 | Engquist et al. |
| 2006/0181959 A1 | 8/2006 | Weiss et al. |
| 2006/0235338 A1 | 10/2006 | Pacheco |
| 2006/0241644 A1 | 10/2006 | Osorio et al. |
| 2006/0264695 A1 | 11/2006 | Viole et al. |
| 2006/0264967 A1 | 11/2006 | Ferreyro et al. |
| 2006/0266372 A1 | 11/2006 | Miller et al. |
| 2006/0271061 A1 | 11/2006 | Beyar et al. |
| 2006/0276819 A1 | 12/2006 | Osorio et al. |
| 2007/0019802 A1 | 1/2007 | Ubriaco et al. |
| 2007/0027230 A1 | 2/2007 | Beyar et al. |
| 2007/0032567 A1 | 2/2007 | Beyar et al. |
| 2007/0055266 A1 | 3/2007 | Osorio et al. |
| 2007/0055267 A1 | 3/2007 | Osorio et al. |
| 2007/0055278 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio |
| 2007/0055300 A1 | 3/2007 | Osorio et al. |
| 2007/0060941 A1 | 3/2007 | Reiley et al. |
| 2007/0118142 A1 | 5/2007 | Krueger |
| 2007/0121422 A1 | 5/2007 | Sand |
| 2007/0142842 A1 | 6/2007 | Krueger |
| 2007/0197935 A1 | 8/2007 | Reiley et al. |
| 2007/0198013 A1 | 8/2007 | Foley et al. |
| 2007/0198023 A1 | 8/2007 | Sand et al. |
| 2007/0198024 A1 | 8/2007 | Plishka et al. |
| 2007/0255282 A1 | 11/2007 | Simonton et al. |
| 2007/0282443 A1 | 12/2007 | Globerman et al. |
| 2008/0039856 A1 | 2/2008 | DiMauro et al. |
| 2008/0044374 A1 | 2/2008 | Lavergne et al. |
| 2008/0058827 A1 | 3/2008 | Osorio et al. |
| 2008/0065087 A1 | 3/2008 | Osorio et al. |
| 2008/0065089 A1 | 3/2008 | Osorio et al. |
| 2008/0065137 A1 | 3/2008 | Boucher et al. |
| 2008/0065142 A1 | 3/2008 | Reiley et al. |
| 2008/0065190 A1 | 3/2008 | Osorio et al. |
| 2008/0071283 A1 | 3/2008 | Osorio et al. |
| 2008/0086133 A1 | 4/2008 | Kuslich et al. |
| 2008/0132935 A1 | 6/2008 | Osorio et al. |
| 2008/0140079 A1 | 6/2008 | Osorio et al. |
| 2008/0140084 A1 | 6/2008 | Osorio et al. |
| 2008/0200915 A1 | 8/2008 | Globerman et al. |
| 2008/0212405 A1 | 9/2008 | Globerman et al. |
| 2008/0228192 A1 | 9/2008 | Beyar et al. |
| 2009/0264892 A1 | 10/2009 | Beyar et al. |
| 2009/0264942 A1 | 10/2009 | Beyar et al. |
| 2009/0270872 A1 | 10/2009 | DiMauro et al. |
| 2010/0065154 A1 | 3/2010 | Globerman |
| 2010/0069786 A1 | 3/2010 | Globerman |
| 2010/0152855 A1 | 6/2010 | Kuslich et al. |
| 2010/0168271 A1 | 7/2010 | Beyar |
| 2010/0268231 A1 | 10/2010 | Kuslich et al. |
| 2012/0307586 A1 | 12/2012 | Globerman et al. |
| 2013/0123791 A1 | 5/2013 | Beyar et al. |
| 2013/0261217 A1 | 10/2013 | Beyar et al. |
| 2013/0345708 A1 | 12/2013 | Beyar et al. |
| 2014/0088605 A1 | 3/2014 | Ferreyro et al. |
| 2014/0148866 A1 | 5/2014 | Globerman et al. |
| 2015/0122691 A1 | 5/2015 | Globerman et al. |
| 2015/0127058 A1 | 5/2015 | Beyar et al. |
| 2015/0148777 A1 | 5/2015 | Ferreyro et al. |
| 2016/0051302 A1 | 2/2016 | Ferreyro et al. |
| 2016/0235459 A1 | 8/2016 | Globerman et al. |
| 2017/0216483 A1 | 8/2017 | Beyar et al. |

FOREIGN PATENT DOCUMENTS

| | | |
|---|---|---|
| CN | 1138001 A | 12/1996 |
| CN | 1310026 A | 8/2001 |
| DE | 136018 C | 11/1902 |
| DE | 368497 C | 2/1953 |
| DE | 1283448 B | 11/1968 |
| DE | 1810799 A1 | 6/1970 |
| DE | 2821785 A1 | 11/1979 |
| DE | 3003947 A1 | 8/1980 |
| DE | 2947875 A1 | 6/1981 |
| DE | 3443167 | 6/1986 |
| DE | 8716073 U1 | 2/1988 |
| DE | 3730298 A1 | 3/1988 |
| DE | 3817101 | 11/1989 |
| DE | 4016135 A1 | 11/1990 |
| DE | 4104092 | 8/1991 |
| DE | 19612276 | 10/1997 |
| DE | 10258140 | 7/2004 |
| EP | 20207 | 6/1908 |
| EP | 486638 | 6/1938 |
| EP | 0044877 | 2/1982 |
| EP | 0190504 | 3/1986 |
| EP | 0177781 | 4/1986 |
| EP | 0 235 905 A1 | 9/1987 |
| EP | 0235905 | 9/1987 |
| EP | 0301759 | 7/1988 |
| EP | 0425200 | 10/1990 |
| EP | 0423916 | 4/1991 |
| EP | 0475077 | 3/1992 |
| EP | 0511868 | 4/1992 |
| EP | 0493789 | 7/1992 |
| EP | 0 242 672 B1 | 10/1992 |
| EP | 0581387 | 2/1994 |
| EP | 0614653 | 9/1994 |
| EP | 0669100 | 8/1995 |
| EP | 0748615 | 12/1996 |
| EP | 0763348 | 3/1997 |
| EP | 1 074 231 A1 | 2/2001 |
| EP | 1074231 | 2/2001 |
| EP | 1095667 | 5/2001 |
| EP | 1103237 | 5/2001 |
| EP | 1104260 | 6/2001 |
| EP | 1 247 454 A1 | 10/2002 |
| EP | 1464292 | 10/2004 |
| EP | 1 517 655 A1 | 3/2005 |
| EP | 1148850 | 4/2005 |
| EP | 1552797 | 7/2005 |
| EP | 1570873 | 9/2005 |
| EP | 1 596 896 A2 | 11/2005 |
| EP | 1598 015 | 11/2005 |
| EP | 1148851 | 5/2006 |
| EP | 1829518 | 9/2007 |
| EP | 1 886 648 A1 | 2/2008 |
| EP | 1886647 | 2/2008 |
| FR | 1548575 A | 12/1968 |
| FR | 2606282 | 5/1988 |
| FR | 2629337 | 10/1989 |
| FR | 2638972 | 5/1990 |
| FR | 2674119 | 9/1992 |
| FR | 2690332 | 10/1993 |
| FR | 2712486 | 5/1995 |
| FR | 2722679 | 1/1996 |
| GB | 2045 | 0/1795 |
| GB | 8331 | 0/1904 |
| GB | 190720207 A | 6/1908 |
| GB | 408668 | 4/1934 |
| GB | 486638 A | 6/1938 |
| GB | 2114005 | 8/1983 |
| GB | 2156824 | 10/1985 |
| GB | 2197691 | 5/1988 |

(56) References Cited

FOREIGN PATENT DOCUMENTS

| | | |
|---|---|---|
| GB | 2268068 | 1/1994 |
| GB | 2276560 | 10/1994 |
| GB | 2411849 | 9/2005 |
| GB | 2413280 | 10/2005 |
| GB | 2469749 | 10/2010 |
| JP | S51-134465 A | 11/1976 |
| JP | 54-009110 | 1/1979 |
| JP | 55-009242 U | 1/1980 |
| JP | 55-109440 | 8/1980 |
| JP | 62-068893 | 3/1987 |
| JP | 63-194722 A | 8/1988 |
| JP | 02-122017 | 5/1990 |
| JP | 02-166235 | 6/1990 |
| JP | 02-125730 U | 10/1990 |
| JP | 4 329956 | 11/1992 |
| JP | 07-000410 | 1/1995 |
| JP | 8322848 | 12/1996 |
| JP | 10146559 | 6/1998 |
| JP | 10-511569 | 10/1998 |
| JP | 2001-514922 A | 9/2001 |
| JP | 2004-16707 | 1/2004 |
| JP | 2005-500103 A | 1/2005 |
| JP | 2008-55367 | 3/2008 |
| RO | 116784 | 6/2001 |
| RU | 1011119 | 4/1983 |
| RU | 1049050 | 10/1983 |
| WO | 88/10129 A1 | 12/1988 |
| WO | WO 90/00037 | 1/1990 |
| WO | WO 92/14423 | 9/1992 |
| WO | WO 94/12112 | 6/1994 |
| WO | 94/26213 A1 | 11/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18866 | 4/1999 |
| WO | WO 99/18894 | 4/1999 |
| WO | WO 99/29253 | 6/1999 |
| WO | WO 99/37212 | 7/1999 |
| WO | WO 99/39661 | 8/1999 |
| WO | WO 99/49819 | 10/1999 |
| WO | WO 99/52446 | 10/1999 |
| WO | WO 00/06216 | 2/2000 |
| WO | WO 00/44319 | 8/2000 |
| WO | WO 00/44321 | 8/2000 |
| WO | WO 00/44946 | 8/2000 |
| WO | WO 00/54705 | 9/2000 |
| WO | WO 00/56254 | 9/2000 |
| WO | WO 01/008571 | 2/2001 |
| WO | WO 01/013822 | 3/2001 |
| WO | 01/56514 A1 | 8/2001 |
| WO | WO 01/54598 | 8/2001 |
| WO | WO 01/060270 | 8/2001 |
| WO | WO 01/60270 | 8/2001 |
| WO | WO 01/76514 | 10/2001 |
| WO | WO 02/00143 | 1/2002 |
| WO | WO 02/02033 | 1/2002 |
| WO | WO 02/19933 | 3/2002 |
| WO | 02/064195 A2 | 8/2002 |
| WO | WO 02/064062 | 8/2002 |
| WO | WO 02/064194 | 8/2002 |
| WO | WO 02/072156 | 9/2002 |
| WO | WO 02/096474 | 12/2002 |
| WO | WO 03/007854 | 1/2003 |
| WO | WO 03/015845 | 2/2003 |
| WO | WO 03/022165 | 3/2003 |
| WO | WO 03/061495 | 7/2003 |
| WO | WO 03/078041 | 9/2003 |
| WO | WO 03/101596 | 12/2003 |
| WO | WO 04/002375 | 1/2004 |
| WO | WO 04/01980 | 3/2004 |
| WO | WO 04/019810 | 3/2004 |
| WO | WO 04/071543 | 8/2004 |
| WO | WO 2004/075965 | 9/2004 |
| WO | WO 2004/080357 | 9/2004 |
| WO | WO 04/110292 | 12/2004 |
| WO | WO 04/110300 | 12/2004 |
| WO | WO 05/000138 | 1/2005 |
| WO | 2005/017000 A1 | 2/2005 |
| WO | WO 05/032326 | 4/2005 |
| WO | WO 2005/048867 | 6/2005 |
| WO | WO 2005/051212 | 6/2005 |
| WO | WO 05/110259 | 11/2005 |
| WO | WO 06/011152 | 2/2006 |
| WO | WO 06/11152 | 2/2006 |
| WO | WO 06/039159 | 4/2006 |
| WO | 2006/062939 A2 | 6/2006 |
| WO | WO 06/090379 | 8/2006 |
| WO | WO 06/90379 | 8/2006 |
| WO | WO 07/015202 | 2/2007 |
| WO | WO 07/036815 | 4/2007 |
| WO | WO 07/148336 | 12/2007 |
| WO | WO 08/004229 | 1/2008 |
| WO | WO 08/032322 | 3/2008 |
| WO | WO 08/047371 | 4/2008 |

OTHER PUBLICATIONS

Mousa, W.F. et al., "Biological and Mechanical Properties of PMMA-Based Bioactive Bone Cements," Biomaterials 21:2137-46 (2000).
Serbetci, K. et al., "Thermal and Mechanical Properties of Hydroxyapatite Impregnated Acrylic Bone Cements," Polymer Testing 23:145-55 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003).
Carrodegus et al., "Injectable Acrylic Bone Cements for Vertebroplasty with Improved Properties," J. Biomed. Materials Res. 68(1):94-104 (Jan. 2004).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Pascual, B. et al., "New Aspects of the Effect of Size and Size Distribution on the Setting Parameters and Mechanical Properties of Acrylic Bone Cements," Biomaterials 17(5):509-16 (1996).
Robinson, R. et al., "Mechanical Properties of Poly(methyl methacrylate) Bone Cement," J. Biomed. Materials Res. 15(2):203-08 (2004).
Saha, S. et a., "Mechanical Properties of Bone Cement: A Review," J. Biomed. Materials Res. 18(4):435-62 (1984).
Andersen, M. et al., "Vertebroplastik, ny behandling of osteoporotiske columnafrakturer?", Ugeskr Laefer 166/6:463-66 (Feb. 2, 2004).
Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.
Chinese Office Action, from CN Appl No. 200680013255.5, dated Jan. 23, 2009.

(56) References Cited

OTHER PUBLICATIONS

European Communication, from EP Appl No. 06711221.9, dated Nov. 24, 2008.
European Search Report, from EP05763930.4; dated Sep. 11, 2008.
Lewis, G., "Properties of Acrylic Bone Cement: State of the Art Review," J. Biomed. Mat. Res. 38(2):155-82 (1997).
Lewis, G., "Toward Standardization of Methods of Determination of Fracture Properties of Acrylic Bone Cement and Statistical Analysis of Test Results," J. Biomed. Mat. Res. 53(6):748-68 (2000).
U.S. Office Action, from U.S. Appl No. 11/461,072, dated Jan. 28, 2009.
U.S. Office Action, from U.S. Appl. No. 11/360,251, dated Apr. 17, 2009.
Cole et al., "AIM Titanium Humeral Nail System," Surgical Technique. DePuy Orthopaedics 17P (2000).
Lewis, "Properties of Ascrylic Bone Cement: State of the Art Review," J. Biomed. Mat. Res. Appl. Biomaterials 38(2):155-82 (p. 158 s.Viscosity) (1997).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Steen, "Laser Surface Treatment," Laser Mat. Processing, Springer 2d ed. ch. 6:218-71 (2003).
Varela et al., "Closed Intramedullary Pinning of Metacarpal and Phalanx Fractures," Orthopaedics 13(2):213-15 (1990).
Supp. EP Search Report, from EP Appl. No. 05763930.4, dated Sep. 11, 2008.
Japanese Interrogation for Application No. 2009-516062 (Appeal No. 2013-002371) dated Jul. 9, 2013 (9 Pages).
Feldman, H., "Die Geschichte der Injektionen," Laryngo-Rhino-Othol 79:239-46 (2000).
Glasgow Medico-Chirurgical Society, The lancet 1364 (May 18, 1907).
Greenberg, "Filling Root Canals by an Injection Technique," Dental Digest 61-63 (Feb. 1963).
Greenberg, "Filling Root Canals in Deciduous Teeth by an Injection Technique," Dental Digest 574-575 (Dec. 1961).
Greig, D., "A New Syringe for Injecting Paraffin," The Lancet 611-12 (Aug. 29, 1903).
International Search Report, from corresponding PCT/IL07/01257, dated Jul. 15, 2008.
Lake, R., "The Restoration of the Inferior Turbinate Body by Paraffin Injections in the Treatment of Atrophic Rhinitis," The Lancet 168-69 (Jan. 17, 1903).
Paget, S., "The Uses of Paraffin in Plastic Surgery," The Lancet 1354 (May 16, 1903).
Walton, A, "Some Cases of Bone Cavities Treated by Stopping With Paraffin," The Lancet 155 (Jan. 18, 1908).
Baroud, G., "Influence of Mixing Method on the Cement Temperature-Mixing Time History and Doughing Time of Three Acrylic Cements for Vertebroplasty," Wiley Periodicals Inc. 112-116 (2003), (Jun. 2003).
European Search Report, from EP 10182769.9, dated Mar. 2, 2011.
European Search Report, from EP 10182693.1, dated Mar. 2, 2011.
European Search Report, from EP 10192302.7, dated Mar. 24, 2011.
European Search Report, from EP 10192301.9, dated Mar. 24, 2011.
European Search Report, from EP 10192300.1, dated Mar. 24, 2011.
Hide, I. et al., "Percutaneous Vertebroplasty: History, Technique and current Perspectives," Clin. Radiology 59:461-67 (2004), (Jan. 2004).
Hu, M. et al., "Kyphoplasty for Vertebral Compression Fracture Via a Uni-Pedicular Approach," Pain Phys. 8:363-67 (2005), (Oct. 2005).
Liang, B. et al., "Preliminary Clinical Application of Percutaneous Vertebroplasty," Zhong Nan Da Xue Bao Yi Xue Ban 31(1):114-9 (2006)(abs. only),( Feb. 2006).
Supp. EP Search Report, from EP Appl. No. 07766863.0, dated Apr. 12, 2011.

JP Office Action, from JP Appl No. 2008-532910, dated Jul. 19, 2011.
Japanese Office Action for Application No. 2009-517607, dated Aug. 27, 2013. (6 pages).
European Search Report, from EP07827231.7, dated Sep. 12, 2011.
European Search Report for Application No. 12181745.6, dated Sep. 25, 2012. (9 pages).
Japanese Office Action for Application No. 2009-517607, dated Aug. 28, 2012. (4 pages).
Japanese Office Action for Application No. 2009-516062, dated Oct. 16, 2012 (6 pages).
International Search Report, from PCT/IL06/00239, dated Jan. 26, 2007.
International Search Report, from PCT/IL05/00812, dated Feb. 28, 2007.
International Search Report, from PCT/IB06/052612, dated Oct. 2, 2007.
International Search Report, for PCT/IL07/00808, dated Aug. 22, 2008.
Marks, Standard handbook for mechanical engineers, section 5 (Tenth ed. 1996).
Supp. EP Search Report, from EP 07766838.2, dated May 18, 2011.
JP Office Action, from JP Appl No. 2009-517607, dated Aug. 9, 2011.
Japanese Office Action dated Feb. 21, 2012 for Application No. 2009-516062 (6 Pages).
Japanese Office Action dated Dec. 6, 2011 for Application No. 2008-524651 (9 Pages).
Mendizabal et al., Modeling of the curing kinetics of an acrylic bone cement modified with hydroxyapatite. International Journal of Polymeric Materials. 2003;52:927-938, (Oct. 2003).
Morejon et al., Kinetic effect of hydroxyapatite types on the polymerization of acrylic bone cements. International Journal of Polymeric Materials. 2003;52(7):637-654, (Jul. 2003).
Sreeja et al., Studies on poly(methyl methacrylate)/polystyrene copolymers for potential bone cement applications. Metals Materials and Processes. 1996:8(4):315-322, (Mar. 1997).
Yang et al., Polymerization of acrylic bone cement investigated by differential scanning calorimetry: Effects of heating rate and TCP content. Polymer Engineering and Science. Jul. 1997;1182-1187.
Australian Office Action dated Mar. 7, 2013 for Application No. 2012203300 (4 pages).
Japanese Office Action dated Apr. 9, 2013 for Application No. 2007-556708.
Kuehn et al., Acrylic bone cements: composition and properties. Orthop Clin North Am. Jan. 2005;36(1):17-28, v.
Japanese Office Action for Application No. 2009-517607, dated Feb. 4, 2014. (8 pages).
European Search Report for Application No. 13174874.1, dated Nov. 13, 2013 (6 pages).
Lindeburg, M., "External Pressurized Liquids," Mechanical Eng. Ref. Manual for the PE Exam, 10:14-15(May 1997).
Lu Orthopedic Bone Cement. Biomechanics and Biomaterials in Orthopedics. Ed. Poitout London: Springer-Verlag London Limited Jul. 2004 86-88.
Chinese Office Action for Application No. 201310064546.9, dated Jul. 31, 2014 (24 pages).
Extended European Search Report for Application No. 14166420.1, dated Jul. 14, 2014 (9 pages).
Baroud et al. "Injection Biomechanics of Bone Cements Used in Vertebroplasty", Biomedical Maerials and Engineering, 00: 1-18, 2004.
Heini et al. "The Use of a Side-Opening Injection Cannula in Vertebroplasty", Spine, 27(1): 105-109, 2002.
Hernandez et al. "Influence of Powder Particle Size Distribution on complex Viscosity and other Properties of Acrylic Bone Cement for Vetebroplasty and Kyphoplasty", Journal of Biomed. Material Research, Part. B, 77B: 98-103, 2006.
Ishikawa et al. "Effects of Neutral Sodium Hydrogen Phosphate on Setting Reaction and Mechanical Strength of Hydroxyapatite Putty",Journal of Biomedical Meterials Research, 44: 322-329, (1999).

(56) References Cited

OTHER PUBLICATIONS

Ishikawa et al. "Non-Decay Type Fast-Setting Calcium Phosphate Cement: Hydroxyapatite Putty Containing an Increased Amount of Sodium Alginate", Journal of Biomed. Materials Research, 36: 393-399, 1997.
Krause et al. "The Viscosity of Acrylic Bone Cements", Jouirnal of Biomedical Materials Research, 16: 219-243, 1982.
Nussbaum et al. "The Chemistry of Acrylic Bone Cements and Implications for Clinical Use in Image-Guided Therapy", Journal of Vasc. Interv. Radiol., 15: 121-126, 2004.
Weissman et al. "Trochanteric Fractures of the Femur. Treatment With a Strong Nail and Early Weight-Bearing", Clinical Orthopedics and Related Research, 67: 143-150, 1969. Fig.
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).
Avalione & Baumeister III, Marks' Standard Handbook for Mechanical Engineers, 10 ed, pp. 5-6 (1996).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An in Vitro Biomechanical Evaluation of Bone Cements Used in Percutaneous Vertebroplasty," Bone 25(2):23S-26S (1999).
Blinc, A et al., "Methyl-methacrylate bone cement surface does not promote platelet aggregation or plasma coagulation in vitro," Thrombosis Research 114:179-84 (2004).
Canale et al., "Campbell's operative orthopaedic-vol. 3-ninth ed", Mosby:P207,2121,2184-85,2890-96, (1998) abstracts.
Codman & Shurtleff, "V-MAX™ Mixing and Delivery Device," Catalog No. 43-1056.
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-76 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
DeWijn, J.R., Characterization of Bone Cements, The Institute of Dental Materials Science and Technology and the Dept of Ortho., Catholic University, Netherlands 46:38-51 (1975).
Edeland, "Some additional suggestions for an intervertebral disc prothesis," J. Biomed. Eng. XP008072822, 7(1):57-62 (1985.
European Search Report, from EP09151379.6, dated Oct. 20, 2009.
European Search Report, from EP06780252.0, dated Oct. 29, 2009.
Fessler, Richard D. et al., "Vertebroplasty," Neurosurgical Operative Atlas 9:233-240 (2000).
Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Gangi, A., "Percutaneous Vertebroplasty Guided by a Combination of CT and Fluoroscopy," AJNR 15:83-86 (1994).
Garfin, S. R. et al., "New Technologies in Spine, Kyphoplasty and Vertebroplasty for the Treatment of Painful Osteoporotic Compression Fractures," Spine 26(14:1511-15 (2001).
Grados F. et al.,"Long-Term Observations of Vertebral Osteoporotic Fractures Treated by Percutaneous Vertebroplasty," Rheumatology 39:1410-14 (2000).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini, P., "Percutaneous Transpedicular Vertebroplasty with PMMA: Operative Technique and Early Results," EUR Spine J. v. 9, pp. 445-450, Springer-Verlag (2000).
Heraeus Palacos R, 2008, Palacos R, high Viscosity Bone Cement.
International Preliminary Report on Patentability, from PCT/IB06/053014, dated Apr. 10, 2008.
International Search Report, from PCT/IL07,00833, dated Apr. 4, 2008.
International Search Report, from PCT/IL07/00484, dated Apr. 17, 2008.
International Search Report, for PCT/MX03/000027, dated Mar. 14, 2003.
Jasper, L.E. et al., "The Effect of Monomer-to-Powder Ratio on the Material Properties of Cranioplastic," Bone 25(2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Jensen, Mary E. et al., "Percutaneous Vertebroplasty in the Treatment of Osteoporotic Compression Fractures," SPINE INTERVENTIONS 10(3):547-568 (2000).
Johnson & Johnson Orthopaedics, The CEMVAC Method, Raynham, MA.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Kuhn, Klaus-Dieter, Bone Cements—Uptodate Comparison of Physical and Chemical Properties of Commercial Materials, Springer-Verlag Heidelberg Germany p. 7-8, 17, 38 (2000).
Kyphom Medical Professionals, KyphXProducts (Nov. 8, 2001).
Li, C. et al., "Thermal Characterization of PMMA-Based Bone Cement Curing," J. Materials Sci.: Materials in Medicine 15:84-89 (2004).
Lieberman, I.H. et al., "Initial Outcome and Efficacy of Kyphoplasty in the Treatment of Painful Osteoporotic Vertebral Compression Fractures," Spine 26(14:1631-38 (2001).
Mathis, John et al., "Percutaneous Vertebroplasty: A Developing Standard of Care for Vertebral Compression Fractures," AJNR Am. J. Neurorad. 22:373-81 (2001).
Medsafe Palacos R 2007, Data Sheet : Palacos R Bone cement with Garamycin pp. 1-7; http://www.medsafe.govt.nz/profs/datasheet/p/palacosbonecements.htm.
O'Brien, J. et al., "Vertebroplasty in patients with Severe Vertebral Compression Fractures: A Technical Report," AJNR 21:1555-58 (2000).
Odian, G., "Principles of Polymerization," pp. 20-23, (1970).
Padovani, B. et al., "Pulmonary Embolism Caused by Acrylic Cement: A Rare Complication of Percutaneous Vertebroplasty," AJNR 20:375-77 (1999).
Palacos R Bone Cement With Garamycin, Data Sheet, http://www.medsafe.govt.nz/profs/datasheet/p/palacosbonecements.htm (Jan. 13, 2010).
Palacos R high viscosity, radiopaque bone cement (Heraeus Dec. 2008).
Parallax Medical, Inc., Exflow Cement Delivery System (May 16, 2000).

(56) References Cited

OTHER PUBLICATIONS

Rimnac, CM, et al., "The effect of centrifugation on the fracture properties of acrylic bone cements," JB&JS 68A(2):281-87 (1986).
Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).
Shah, T., Radiopaque Polymer Formulations for Medical Devices; Medical Plastics and Biomaterials Special Section; Medical device & Diagnostic Industry pp. 102-111 (2000).
Supp. EP Search Report, from EP Appl. No. 06711221.9, dated Sep. 15, 2008.
Vasconcelos, C., "Transient Arterial Hypotension Induced by Polymethyacrylated Injection During Percutaneous Vertebroplasty," Letter to the Editor, JVIR (Aug. 2001).
Wimhurst, J.A., et al., "The Effects of Particulate Bone Cements at the Bone-Implant Interface," J. Bone & Joint Surgery pp. 588-592 (2001).
Wimhurst, J.A. et al., "Inflammatory Responses of Human Primary Macrophages to Particulate Bone Cements in Vitro," J. Bone & Joint Surgery 83B:278-82 (2001).
[No Author Listed] ASTM Designation F 451-99a ε1, Standard Specification for Acrylic Bone Cement, Published Jul. 1999, Editorially corrected Jun. 2003, ASTM International, 8 pages.
[No Author Listed] DePuy CMW Heritage Bone Cements, Product Information, © 2016, DePuy Synthes, Johnson & Johnson Medical Limited; brochure issued Oct. 2016, 8 pages.
Chinese Office Action for Application No. 201510099411.5, dated Aug. 16, 2017 (10 pages).
European Communication dated Jul. 1, 2015 for Application No. 10182769.9, enclosing third party observations concerning patentability (Submission dated Jun. 25, 2015) (6 pages).
Notice of Opposition to a European Patent for Patent No. 2314259, from KIPA AB (EP Application No. 10182769.9), dated Apr. 28, 2016 (72 pages).
Notice of Opposition to a European Patent for Patent No. 2314259, from Loyer & Abello (EP Application No. 10182769.9), dated Apr. 28, 2016 (40 pages).
Submission in Opposition Proceedings in European Patent No. 2314259, by KIPA AB, dated Sep. 21, 2017 (16 pages).
Submission in Opposition Proceedings in European Patent No. 2314259, by Layer & Abello, dated Sep. 20, 2017 (10 pages).
European Communication for Application No. 10192301.9, dated Sep. 17, 2015, enclosing third party observations concerning patentability (Submission dated Sep. 11, 2015 (22 pages).
Extended European Search Report for Application No. 16173186.4, dated Oct. 6, 2016 (11 pages).

* cited by examiner

METHODS, MATERIALS AND APPARATUS FOR TREATING BONE AND OTHER TISSUE

RELATED APPLICATIONS

The present application claims priority from Israel Application No. 166017 filed on Dec. 28, 2004. The present application claims the benefit under 35 USC 119(e) of U.S. Provisional Application No. 60/592,149 filed on Jul. 30, 2004; 60/647,784 filed on Jan. 31, 2005 and 60/654,495 filed on Feb. 22, 2005. The present application is also a Continuation-in-Part of PCT Application No. PCT/IL2004/000527 filed on Jun. 17, 2004, which claims priority from Israel Application No. 160987 filed on Mar. 21, 2004, and which claims the benefit under 35 USC 119(e) of the following U.S. Provisional Applications 60/478,841 filed on Jun. 17, 2003; 60/529,612 filed on Dec. 16, 2003; 60/534,377 filed on Jan. 6, 2004 and 60/554,558 filed on Mar. 18, 2004. The disclosures of all of these applications are incorporated herein by reference.

FIELD OF THE INVENTION

The present invention relates to structural enhancement of the human body, for example, by injection of a material which does not set to a hardened condition.

BACKGROUND OF THE INVENTION

A common occurrence in older persons is compression fractures of the vertebrae, causing both pain and a shortening (or other distortion) of stature. One common treatment is vertebroplasty, in which cement is injected into a fractured vertebra. While this treatment fixes the fracture and reduces pain, it does not restore the vertebra and person to their original height. Another problem is that the injected cement may be injected out of the vertebra or may migrate out through cracks in the vertebra. This may cause considerable bodily harm.

Another common treatment is kyphoplasty, in which the fracture is reduced, for example by first inflating a balloon inside the vertebra and then injecting a fixing material and/or an implant. The problem of cement migration is reduced, but not avoided, as a lower pressure can be used to inject the cement.

Some fixing materials, such as polymethylmethacrylate (PMMA), emit heat and possibly toxic materials while setting. These may further weaken the bone and possibly cause the cement to loosen and/or the bone to fracture.

It has recently been suggested that some fixing materials, being harder than bone, induce fractures in nearby bones.

It is also known to use bone-like repair materials, such as a slurry of bone chips, which apparently do not induce such fractures. However, injecting such materials is difficult due to their viscosity. There have also been attempts to reduce cement migration by injecting more viscous cement, for example, during the doughing time and the beginning of polymerization. However, the injection methods suggested require higher pressures for the more viscous material. Also, some types of viscous materials, such as hardening PMMA, have a small workability window at high viscosities, as they harden very quickly once they reach a high viscosity. This has generally prevented very viscous materials and the associated very high pressures from being used. One possible reason is that as pressures increase, the physician is prevented from receiving feedback on the resistance of the body to the injection of the cement. Thus, over-injection can easily occur.

Another way of increasing viscosity for injection is increasing a monomer-powder concentration ratio (MPR). However, it should be noted that increasing a cement's MPR can lead to marked drops in some of its mechanical properties, such as elastic modulus, yield strength and ultimate strength.

US patents and U.S. Pat. Nos. 4,969,888, 5,108,404, 6,383,188, 2003/0109883, 2002/0068974, U.S. Pat. Nos. 6,348,055, 6,383,190, 4,494,535, 4,653,489 and 4,653,487, the disclosures of which are incorporated herein by reference describe various tools and methods for treating bone. The present application is related to U.S. application Ser. No. 09/890,172 (now U.S. Pat. No. 7,621,950) filed on Jul. 25, 2001 and U.S. application Ser. No. 09/890,318 (now U.S. Pat. No. 7,097,648) filed on Jul. 25, 2001, the disclosure of which are incorporated herein by reference.

SUMMARY OF THE INVENTION

An aspect of some embodiments of the invention relates to both moving and supporting bone using a same material, which is not enclosed by a bag to prevent migration of the material. In an exemplary embodiment of the invention, a material which does not set to a hardened condition is injected into a bone which is fractured and the pressure of the injected material moves the fractured pieces of the bone. The injected material remains in the bone to provide support and prevent retrograde motion of the bone, for example, permanently or until the bone heals. Optionally, an additional material or implant may be provided to further support the bone, however, the injected material supports at least 20%, 30%, 40%, 50% of the forces applied by the bone pieces, or smaller, intermediate or greater percentages. Optionally, the additional material is a cement which sets to a hardened condition.

In an exemplary embodiment of the invention, the material used is an artificial material. In an alternative embodiment of the invention, the material is natural.

In various embodiments of the invention, the following types of materials are used:

(a) Relatively (to bone) soft solid materials which can optionally undergo substantial plastic deformation without tearing and optionally include no cross-linking above type I. In an exemplary embodiment of the invention, these materials are compressed radially and provided through a narrow diameter aperture into the bone. In an alternative exemplary embodiment of the invention, the material is provided in a small profile condition and either compressed axially for loading into a delivery system or simply advanced into the bone without initial compression.

In an exemplary embodiment of the invention, the soft materials are plastically deforming materials. In the example of intra-vertebral use, at least 50%, 80%, 90%, 95% or more of deformation is optionally plastic deformation. Optionally, the materials have an elastic deformation of 0.1% or less. In an exemplary embodiment of the invention, for a material 1 mm in thickness, elastic spring-back is less than 0.1 mm, less than 0.05 mm or less.

(b) High viscosity fluids, such as bone slurry, semi-hardened cement and putty-like materials. These materials are flowed through the delivery system, optionally under a high pressure. In some cases, the fluids set to a hardened condition, for example, due to a polymerization process or due to contact with body fluids.

An aspect of some embodiments of the invention relates to fracture reduction (e.g., height restoration in a vertebra), using a soft material that is not constrained by an enclosure. In an exemplary embodiment of the invention, the material is a soft material softer than 60A, 70A, 80A, 90A or 100A shore. Optionally, the material is at least 10A shore or 20A shore, for example, at least 20A or 30A shore.

In an alternative exemplary embodiment of the invention, the material is a flowable material, for example, with a viscosity greater than 100 Pascal-second, 300 Pascal-second, 500 Pascal-second, 600 Pascal-second, 800 Pascal-second, 1000 Pascal-second or more. Optionally, the material has a viscosity of less than 4,000 Pascal-second, optionally less than 1,800 Pascal-second, optionally less than 1,400 Pascal-second, optionally less than 1,100 Pascal second or smaller intermediate or larger values.

An aspect of some embodiments of the invention relates to the use of materials which do not set to a hardened condition for supporting bone. In an exemplary embodiment of the invention, the material is injected into a bone.

As used herein, the term "setting" is used to define materials whose mechanical properties, such as strength and/or hardness, increase for chemical reasons, for example, due to polymerization during and/or shortly after implantation, e.g., after a few hours, a few days or a few weeks. It should be noted that a material which sets to a non-hardened condition is a setting material. A pre-set soft material will also generally not set to a hardened condition.

As used herein the term "hardened condition" is used to describe materials that are 50% or more the hardness of cortical bone. In some cases it is desirable to compare the strength and/or young modulus of the material to cortical and/or trabecular bone, in which case, values within 110% or 120% or 130% or intermediate values of the values for the bone in question bone may be desirable.

In an exemplary embodiment of the invention, the injected material is selected to have a high viscosity or is a soft material which can undergo plastic deformation, for example, by the material not tearing during an injection via a small diameter tube. Optionally, the material is mechanically sheared during injection.

In an exemplary embodiment of the invention, the use of a non-hardening material allows more flexibility in injection methods, due to the relieving of time constraints typically involved in using a cement which sets to a hardened condition, such as PMMA, in which the time between mixing and setting and especially the time at a given viscosity range, constrains the physician. Optionally, a non-hardening material is more convenient to use, as it does not require the user to mix the material at the time of use. In an exemplary embodiment of the invention, the material is provided in a pre-loaded magazine or delivery system.

A potential property of using a viscous or soft solid material is that there is less danger of leakage out of the vertebra. Optionally, various components are added to the material, for example, a bone growth factor or a radio-opaque material.

A potential advantage of some pre-set or non-setting materials is that an exothermic setting reaction is avoided.

In an exemplary embodiment of the invention, the injected material is free of cross-linking or includes only type I cross-linking.

Optionally, the injected material softens over time.

In an exemplary embodiment of the invention, the material is formulated so that only hardens in the presence of water or other materials common in the body but does not set or harden outside the body. Thus the material can be pre-formulated and mixed and will only set after being introduced into the body. Optionally, the material sets after 10-30 minutes or longer.

An aspect of some embodiments of the invention relates to treatment of body tissues by injecting a non-solid or soft-solid material harder than 10A shore. In an exemplary embodiment of the invention, the injected material flows into or is forced into an intra-body space to be filled thereby. In an exemplary embodiment of the invention, the injected material is viscous enough or solid enough so it does not inadvertently migrate out of a tissue into which it is injected, for example, out of a vertebra. This viscosity level used may depend on the size and/or shape of voids leading out of the tissue being treated. Optionally, the material sets to a hardened condition. Alternatively, the material does not.

In an exemplary embodiment of the invention, the material is provided under a pressure of greater than 40 atmospheres.

An aspect of some embodiments of the invention relates to a method of providing a flowable or soft-solid material into the body, in discrete units, optionally of predetermined quantities. In an exemplary embodiment of the invention, a delivery system with a first quantity of material is provided and a user can select a discrete amount of this first quantity to be injected. This is in contrast to continuous methods in which material is injected until a user stops the injection or the material is all used up. Optionally, the material to be injected is provided in a magazine from which a unit of material can be selected for injection. Optionally, selection is by cutting the material away from the magazine.

In an exemplary embodiment of the invention, a treatment for a bone is provided by injecting two, three, four or more discrete units of material.

A potential advantage of working in discrete portions which are considerably smaller than a total therapeutic amount, in some embodiments of the invention, is that a friction between the material and a delivery system is reduced, as the amount of material advanced at each time is reduced.

An aspect of some embodiments of the invention relates to using a sleeve for delivering material or a device implant that have a high friction to a delivery system, to a site inside the body. In an exemplary embodiment of the invention, the sleeve is designed to reduce friction between the delivered material and a delivery system. Optionally, the sleeve is provided inside of a delivery tube. Optionally, force is applied directly on the sleeve to deliver the material or implant.

An aspect of some embodiments of the invention relates to a system for delivering material into a bone which system is adapted to travel over a guidewire. Optionally, the system travels over a guidewire when loaded. Alternatively or additionally, the system is loaded after being introduced into the body. In an exemplary embodiment of the invention, the system comprises a distal end adapted to penetrate bone, for example vertebral bone. In an exemplary embodiment of the invention, the system is adapted to deliver the material into a vertebra in a manner which will at least partially restore a height of said vertebra. In an exemplary embodiment of the invention, the material surrounds the guidewire.

An aspect of some embodiments of the invention relates to a system for delivering material into a bone under pressure, the system being adapted to penetrate bone. In an exemplary embodiment of the invention, the system comprises a distal tip adapted to penetrate bone. Optionally, an aperture is formed near the distal tip for delivering of said material.

An aspect of some embodiments of the invention relates to materials for use in the body for supporting hard tissue and which do not set to a hardened condition when in storage (e.g., for over 1 hour or over one day or 1 week). In an exemplary embodiment of the invention, the material comprises polymers without cross-linking or with type I cross-linking. Optionally, the composition of the material is a mixture of Laurylmethacrylate (LMA) and methylmethacrylate (MMA), for example in a ratio of between 90:10 and 10:90. Optionally, the material is thermoplastic rather than thermosetting.

In an exemplary embodiment of the invention, the material is a putty-like material. In one example, the material is composed of a mixture of hydroxyapatite and sufficient sodium alginate, such that the mixture remains putty like after time, at least if not in contact with water.

In an exemplary embodiment of the invention, the material softens over time. Optionally, the material is composed of MMA and LMA with poly-HEMA added, and softens by the absorption of body fluids by the composition.

Alternatively or additionally, water soluble materials, such as salts or materials which degrade in body fluids, such as some sugars and plastics, are added and when they degrade, soften the material.

In an exemplary embodiment of the invention, the material hardens over time, but does not harden completely. Optionally, the material includes a solvent, such as NMP (N-methyl pyrolidone), which is soluble in water and as it is carried away, the material hardens somewhat.

Optionally, the actually injected material includes one or more added components. Optionally, one or more of a radio opaque marker, antibiotic, anti-inflammatory and/or bone growth factor, are provided as the added components. Optionally, an added component is added by volume of less than 30% of the material volume and in total less than 50% for all the added components.

Optionally, the added materials are chemically inert but may have a structural effect, for example, due to bulk thereof.

Optionally, non-inert materials are added, for example, 5% of a cement which sets to a hardened condition may be added. Optionally, such non-inert materials are mixed-in at a coarse grain.

An aspect of some embodiments of the invention relates to using a material which sets to a hardened condition, which maintains a high viscosity value during a substantial window of time. In an exemplary embodiment of the invention, the viscosity is between 600 Pascal-second and 1,800 Pascal-second during a period of at least 5 or at least 8 minutes. In an exemplary embodiment of the invention, the material is composed of a mixture of PMMA beads and/or styrene beads and MMA monomers, with the increase in viscosity being provided by the size of the beads of, for example, 10-200 microns and/or by changing the ratio between beads and liquid MMA monomer. Optionally, as setting progresses, viscosity due to the beads is replaced/increased by viscosity due to the polymerization process.

An aspect of some embodiments of the invention relates to treating compression fractures by heating a compressed vertebra. Optionally, the heating is provided by a stand-alone tool. Optionally, the heating is provided to replace heating which is otherwise provided by the setting of a cement. Optionally, a thermocouple or other temperature sensor is used to control the amount of heating provided.

An aspect of some embodiments of the invention relates to a method of selecting mechanical properties of an implant to match those of a bone, cortical and/or trabecular, being treated. In an exemplary embodiment of the invention, one or more of hardness, strength and/or Young modulus are matched.

There is thus provided in accordance with an exemplary embodiment of the invention, a method of treating a vertebra, comprising:

(a) accessing an interior of a vertebra; and (b) introducing a sufficient amount of artificial biocompatible material which does not set to a hardened condition in storage, into said bone, with sufficient force to move apart fractured portions of said bone.

Optionally, said material does not set to a hardened condition after introduction into the body.

In an exemplary embodiment of the invention, said material can be stored for over 1 day.

In an exemplary embodiment of the invention, said material softens after implantation.

In an exemplary embodiment of the invention, said material partly hardens after implantation.

In an exemplary embodiment of the invention, said material does set to a hardened condition after introduction into the body.

In an exemplary embodiment of the invention, said material does not set to a hardened condition in storage.

In an exemplary embodiment of the invention, said material is artificial.

In an exemplary embodiment of the invention, said material is a plastically deforming material. Optionally, said material has a hardness of between 10A shore and 100A shore. Alternatively or additionally, said material is free of cross-linking higher than type I. Alternatively or additionally, said material is thermoplastic. Alternatively or additionally, said material comprises LMA (lauryl methacrylate) and MMA (methyl methacrylate).

In an exemplary embodiment of the invention, said material is a viscous fluid. Optionally, said material has a viscosity between 600 Pascal-second and 1,800 Pascal-second.

In an exemplary embodiment of the invention, introducing comprises introducing at a pressure of at least 40 atmospheres.

In an exemplary embodiment of the invention, introducing comprises introducing at a pressure of at least 100 atmospheres.

In an exemplary embodiment of the invention, introducing comprises introducing through a delivery channel having a diameter of less than 6 mm and a length of at least 70 mm.

In an exemplary embodiment of the invention, introducing comprises introducing through an extrusion aperture having a minimum dimension of less than 3 mm.

In an exemplary embodiment of the invention, introducing comprises introducing through an extrusion aperture having a minimum dimension of less than 1.5 mm.

In an exemplary embodiment of the invention, introducing comprises introducing through a plurality of extrusion apertures simultaneously.

In an exemplary embodiment of the invention, introducing comprises changing an introduction direction during said introduction.

In an exemplary embodiment of the invention, introducing comprises changing an introduction position during said introduction.

In an exemplary embodiment of the invention, said material comprises at least one material adapted to function in a capacity other than structural support.

In an exemplary embodiment of the invention, introducing comprises advancing said material using a motor.

In an exemplary embodiment of the invention, introducing comprises advancing said material using a hydraulic source.

In an exemplary embodiment of the invention, introducing comprises introducing said material in discrete unit amounts. Optionally, at least some of the units have different mechanical properties form each other.

In an exemplary embodiment of the invention, introducing comprises cutting said material away from a delivery system.

In an exemplary embodiment of the invention, introducing comprises not twisting said material during said introducing.

In an exemplary embodiment of the invention, introducing comprises shaping an extrusion form of said material using an exit aperture.

In an exemplary embodiment of the invention, accessing comprises accessing using a guidewire and providing a delivery system over the guidewire.

In an exemplary embodiment of the invention, accessing comprises accessing using a delivery system of said material.

In an exemplary embodiment of the invention, introducing comprises introducing without a separate void forming act.

In an exemplary embodiment of the invention, introducing comprises introducing without a spatially constraining enclosure.

In an exemplary embodiment of the invention, introducing comprises introducing in a spatially constraining enclosure.

In an exemplary embodiment of the invention, introducing comprises also introducing at least 10% by volume of a material which sets to a hardened condition.

In an exemplary embodiment of the invention, the method comprises selecting said material to have at least one of hardness and Young modulus properties less than those of trabecular bone of said vertebra, after a week from said implantation.

In an exemplary embodiment of the invention, said introduced material is operative to support at least 30% of a weight of vertebra within a week after implantation.

There is also provided in accordance with an exemplary embodiment of the invention, a surgical set comprising:

at least one tool adapted to deliver a material into a vertebra; and at least 1 cc of artificial biocompatible prepared material that does not set to a hardened condition outside the body. Optionally, said at least one tool comprises a pressure delivery mechanism capable of delivering said material at a pressure of above 100 atmospheres. Alternatively or additionally, said set comprises a disposable hydraulic actuator. Alternatively or additionally, said set comprises a replaceable magazine for storing said material.

There is also provided in accordance with an exemplary embodiment of the invention, a method of treating bone, comprising:

(a) accessing an interior of a bone; and (b) introducing a sufficient amount of biocompatible material into said bone, without an enclosure between said material and the bone, said introducing being with sufficient force to move apart fractured portions of said bone. Optionally, the method comprises leaving said material in said bone to resist at least 30% of a normative force which urges said portions together.

Optionally, said bone is a vertebra. Optionally, said material does not set to a hardened condition in storage. Alternatively or additionally, said material does not set to a hardened condition in the body.

There is also provided in accordance with an exemplary embodiment of the invention, a method of treating a vertebra, comprising:

(a) accessing an interior of a vertebra; and (b) introducing a sufficient amount of spatially unconstrained biocompatible soft material having a hardness of less than 100A Shore into said vertebra, with sufficient force to move apart fractured portions of said bone.

There is also provided in accordance with an exemplary embodiment of the invention, a surgical set comprising:

at least one tool adapted to deliver a material into a vertebra; and at least 1 cc of biocompatible prepared material that has a Young modulus of less than 120% of healthy vertebral trabecular bone and is prepared at least 1 day ahead of time.

There is also provided in accordance with an exemplary embodiment of the invention, a method of treating a bone, comprising:

(a) accessing an interior of a bone; and (b) introducing, via a delivery tube, into said bone an unconstrained plastically deformable solid material harder than 10A shore and softer than 100A shore.

There is also provided in accordance with an exemplary embodiment of the invention, apparatus for delivering a material or an implant into a bone, comprising:

(a) a delivery tube having a lumen and a distal end adapted for insertion into a body;

(b) a payload comprising at least one of material and an implant inside said lumen;

(c) a lining disposed between said tube and said payload; and (d) an advancing mechanism adapted to move said liner and said payload to said distal end, wherein said liner reduces a friction of said payload against said delivery tube. Optionally, the apparatus comprises a splitter which splits said sleeve.

In an exemplary embodiment of the invention, said mechanism pulls said sleeve.

In an exemplary embodiment of the invention, said mechanism pushes said payload.

In an exemplary embodiment of the invention, said sleeve folds over said delivery tube.

There is also provided in accordance with an exemplary embodiment of the invention, a biocompatible material which does not set to a hardened condition and does not include cross-linking of a type greater than type I and formed of MMA (methyl methacrylate). Optionally, said material is formed of a mixture of MMA and LMA (lauryl methacrylate)

There is also provided in accordance with an exemplary embodiment of the invention, a second medical use of PMMA for height restoration of vertebral bones when applied directly into a vertebra. Optionally, said PMMA is applied during setting while at a viscosity higher than 400 Pascal-second.

There is also provided in accordance with an exemplary embodiment of the invention, a second medical use of bone putty for vertebral treatment when applied under pressure through a tubular delivery system into a vertebral bone.

There is also provided in accordance with an exemplary embodiment of the invention, a polymerizing composition, comprising:

(a) a first quantity of beads having a set of sizes; and (b) a second quantity of monomer, wherein said quantities are selected so that a mixture of said quantities results in a setting material having a workability window of at least 5 minutes at a viscosity between 500 and 2000 Pascal-second.

There is also provided in accordance with an exemplary embodiment of the invention, a method of treating bone, comprising providing a heat source into a vertebra in a controlled manner.

There is also provided in accordance with an exemplary embodiment of the invention, a composite tool for accessing bone, comprising:

an elongate body having:

(a) a head adapted to penetrate bone;

(b) an aperture adapted to extrude material into bone, near said head; and (c) a lumen adapted to deliver material to said aperture; and a source of material under pressure. Optionally, the tool comprises a lumen for a guidewire.

There is also provided in accordance with an exemplary embodiment of the invention, a composite tool for accessing bone comprising:

a drill tool including a lumen;

a separable guidewire adapted to fit in said lumen; and a handle adapted to control the relative positions of said drill tool and said guidewire.

BRIEF DESCRIPTION OF THE FIGURES

Exemplary non-limiting embodiments of the invention will be described with reference to the following description of embodiments in conjunction with the figures. Identical structures, elements or parts which appear in more than one figure are generally labeled with a same or similar number in all the figures in which they appear, in which.

DETAILED DESCRIPTION OF EXEMPLARY EMBODIMENTS

Overview of Exemplary Process

Figure 1A:
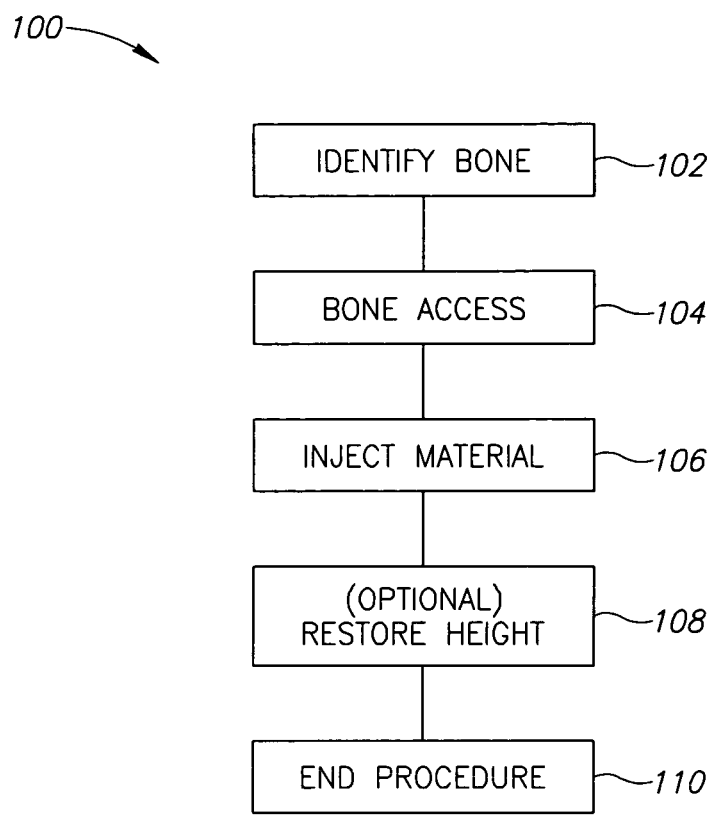
FIG. 1A is a general flowchart of a process of treating a compression fracture, in accordance with an exemplary embodiment of the invention.

FIG. 1A is a general flowchart 100 of a process of treating a compression fracture, in accordance with an exemplary embodiment of the invention.

At 102, a bone to be treated is identified. In the case of a vertebra, this usually involves X-ray or CT images to identify a vertebra or other bone that is fractured, for example by a compression fracture. The following description focuses on vertebral compression fractures but some embodiments of the invention are not limited to such cases.

In an exemplary embodiment of the invention, the access is minimally invasive, for example, only a single channel is formed into the body. Optionally, the procedure is carried out via a cannula having a diameter of, for example of 5 mm, 4 mm or less in diameter is inserted into the body. In some cases, multiple openings into the body are formed. The procedure can also be carried out using a surgical or keyhole incision, however, this may require a longer recuperation period by the patient. Optionally, the cannula (and corresponding length of a delivery tube described below) is at least 50 mm, 70 mm, 100 mm or more or intermediate or smaller values.

At 104, the vertebra is accessed.

At 106, a material, having a high viscosity in some embodiments of the invention, is injected into the vertebra.

At 108, material is optionally provided in a manner and/or amount which restores at least part of the height of the vertebra, for example, 20%, 40%, 50% or intermediate or a higher percentage of a pre-compression height. A particular feature of some embodiments of the invention is that the provided material is of sufficient viscosity or sufficiently solid that leakage from the vertebra is reduced or prevented, as compared to liquid PMMA cement. A pressure used to advance the material may be higher than what is known in the art to match the increased viscosity.

At 110, the procedure is completed and the tube is removed.

Exemplary Bone Access Set

Figure 2:
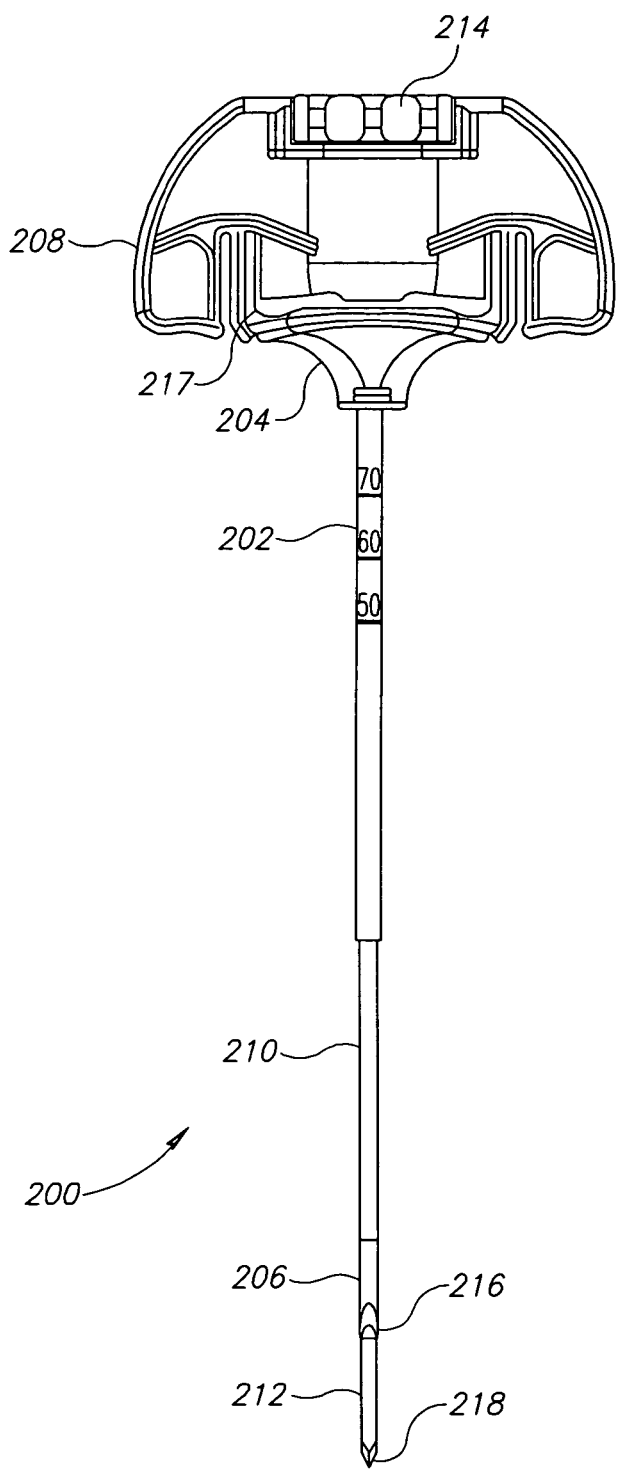
FIG. 2 shows a composite tool for accessing a vertebra, in accordance with an exemplary embodiment of the invention.

Before going into the details of the procedure, the tools used are first described. FIG. 2 shows a composite tool 200 optionally used for accessing the bone, in accordance with an exemplary embodiment of the invention. In an exemplary embodiment of the invention, the access tools used comprise a set of component tools that interlock to act, selectively, as a single tool or as separate tools. In an exemplary embodiment of the invention, this composite set/tool serves as a one step access system in which only a single insertion of objects into the body is required. Optionally, as described below, the delivery system is also inserted at the same time. Optionally, a cannula portion of the tool is omitted, for example as described in the embodiments of FIGS. 12A-12C.

In an exemplary embodiment of the invention, the components of tool 200 are coaxially matched components, which fit one within the lumen of the next.

An optional cannula 202 comprises a handle 204 and a body including a lumen.

An optional drill tool 206 includes an elongate body adapted for drilling and a handle 208. Optionally, handle 208 selectively rotationally locks to handle 204, for manipulation using a single hand, optionally using a snap-lock 217. The body of tool 206 fits in the lumen of cannula 202. Optionally, a section 210 of tool 206 is marked to be visible on an x-ray image, even in contrast to cannula 202. Optionally, this allows the difference in diameters between cannula 202 and drill tool 206 to be minimal. Absent such a marker, in some cases, the difference in diameters may not be visible on an x-ray image and the two tools cannot be distinguished.

An optional guidewire 212 is provided inside a lumen of drill tool 206. Optionally, a knob or other control 214 is provided for selective advancing and/or retracting of guidewire 212 relative to drill 216. The knob may be marked with relative or absolute positions.

Optional depth marking are provided on cannula 202.

Figure 1B:
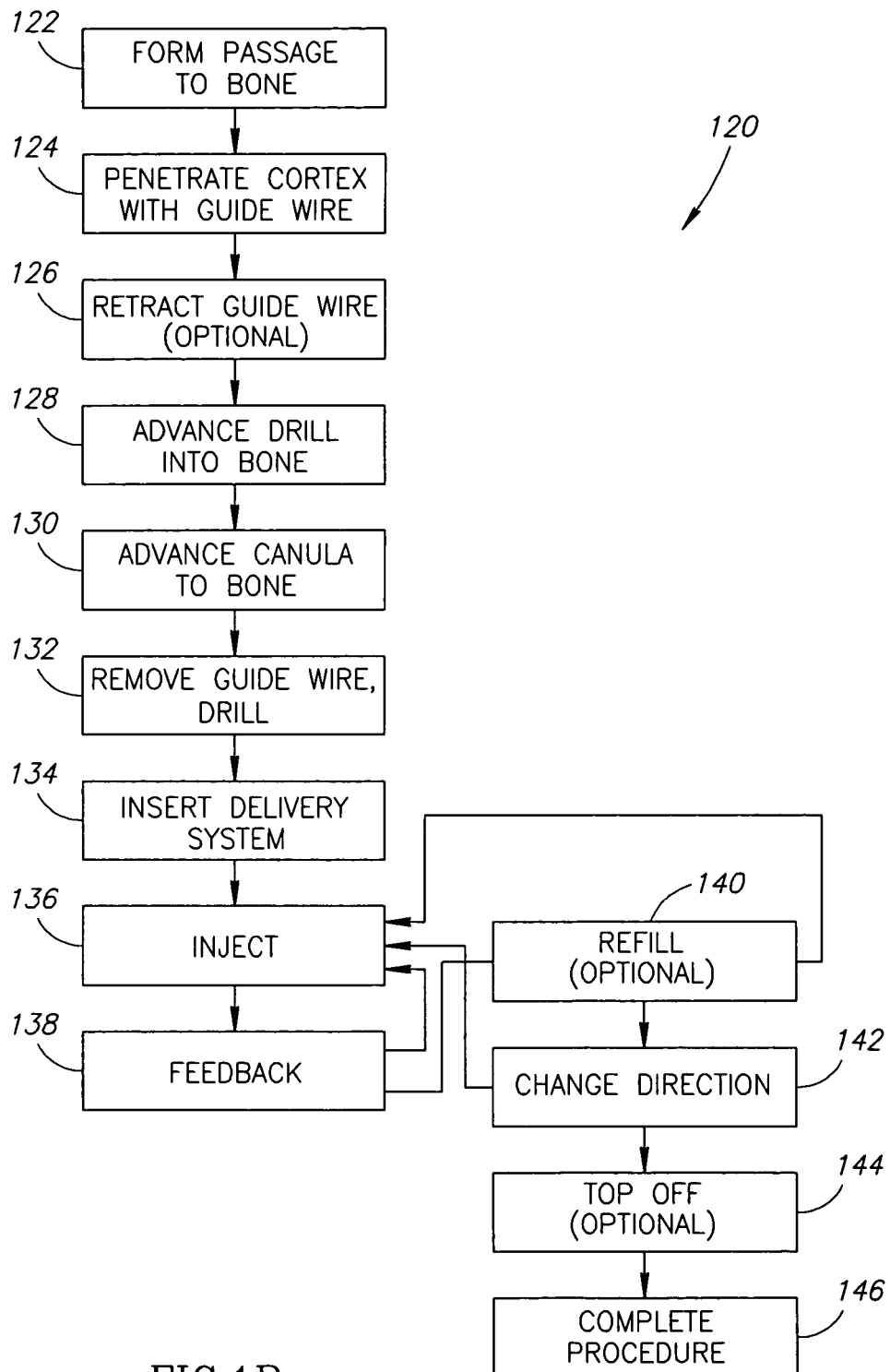
FIG. 1B is a more detailed flowchart of a process of treating a compression fracture, in accordance with an exemplary embodiment of the invention.

An exemplary use of these tools will be described below, in which FIGS. 3A-3F schematically show the progress as a vertebra 300 having a compression fracture 306 is being treated, paralleling a detailed flowchart 120 shown in FIG. 1B.

Penetrate to Bone

At 122 (FIG. 1B), a passage is formed to the bone through a skin layer 312 and intervening tissue, such as muscle and fat. Optionally, the passage is formed by advancing composite tool/set 200 until a tip 218 of guidewire 212 contacts the bone. In some embodiments, tip 218 is designed to drill in soft tissue (e.g., includes a cutting edge). Alternatively or additionally, tip 218 includes a puncturing point adapted to form a puncture in soft tissue.

Figure 3A:
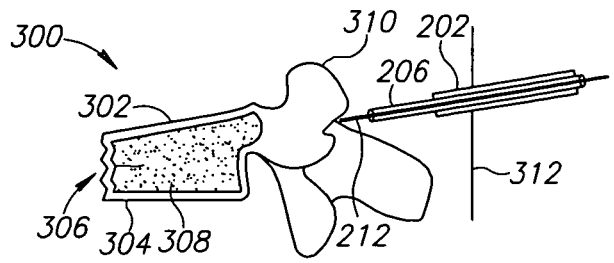
FIGS. 3A-3F show stages of a method of treatment according to FIGS. 1A and 1B, in an exemplary implementation of the method.

This is shown in FIG. 3A. Also shown are cortical plates 302 and 304 of the vertebra and a cancellous bone interior 308.

A single pedicle 310 is shown, due to the view being cross-sectional. Optionally, the access to the vertebra is via a pedicle. Optionally, the access is via both pedicles. Optionally, an extrapedicular approach is used. Optionally, the access point or points are selected to assist in an even lifting of the vertebra.

Penetrate Bone

Figure 3B:
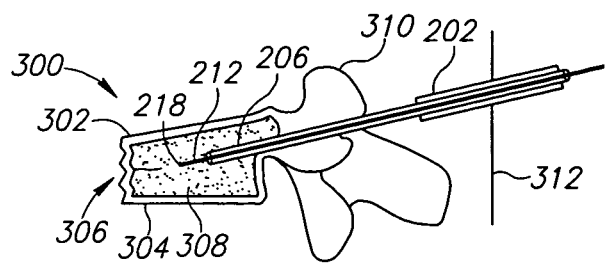

At 124, tip 218 penetrates through the cortex of the bone being treated (FIG. 3B). In an exemplary embodiment of the invention, tip 218 is separately manipulated from the rest of composite tool 200. Optionally, tip 218 is advanced until it contacts a far side of the vertebra.

In an exemplary embodiment of the invention, tip 218 of guidewire 212 is formed to drill in bone and is advanced through the vertebral cortex by rotation or vibration. Optionally, it is advanced by tapping thereon or applying pressure thereto.

Optionally, a relative position of the guidewire and the cannula is noted, to assist in determining the inner extent of the vertebra.

At 126, the guidewire is optionally retracted. Optionally, the guidewire is axially locked to drill tool 206. Optionally, guidewire 212 and drill tool 206 align so that tip 218 and a tip 216 of the drill tool form a single drilling tip.

Figure 3C:
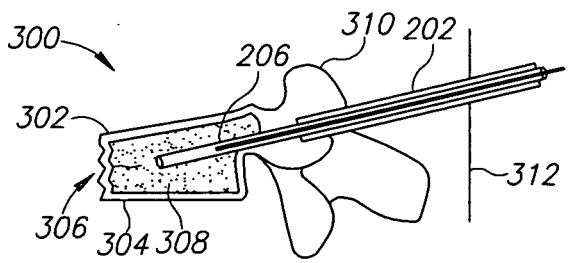

At 128, drill tool 206 is advanced into the bone (FIG. 3C). Optionally, tip 216 of drill tool 206 designed for drilling and/or is advanced, for example, by tapping, rotation and/or vibration. Optionally, the drill tool is advanced to the far side of the vertebra. Optionally, the previous depth marking of the guidewire is used to limit this advance. Optionally, the guidewire is not retracted at 126. Instead, drill tool 206 is advanced over the guidewire until it reaches the end of the guidewire.

At 130, cannula 202 is optionally advanced to the bone over the drill. Optionally, the leading edge of the cannula is threaded or otherwise adapted to engage the bone at or about the bore formed by the drill tool. Optionally, the cannula is inserted into the bone.

Figure 3D:
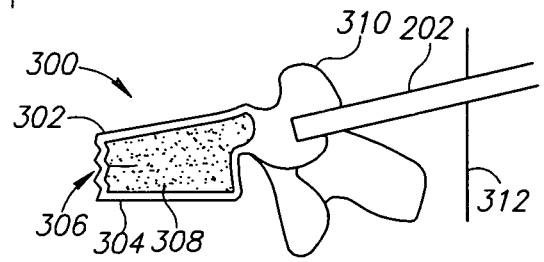

At 132, the guidewire and/or drill tool are optionally removed (FIG. 3D).

In some embodiments, the cannula is not advanced all the way to the bone. In others, the cannula may be advanced into the bone, for example, to prevent contact between the treatment and cortical bone and/or weak or fractured bone. Optionally, the cannula is advanced past the pedicle and to the vertebral interior 308.

Optionally, a reamer (not shown) is inserted into the cannula and used to remove tissue from interior 308.

Inject Material

Figure 3E:
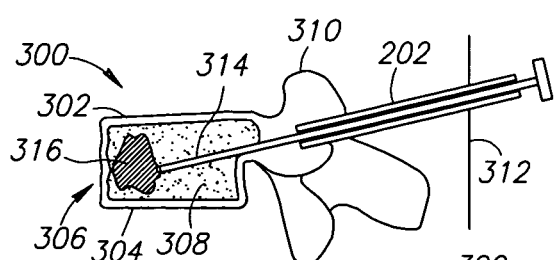

At 134, a material delivery system 314 is provided into cannula 202 (shown in FIG. 3E). Optionally, the delivery system delivers material to a side thereof (described below).

At 136, system 134 is activated to inject material 316 into interior 308. FIG. 3E shows that when enough material is injected, vertebral height may be partially or completely restored. The injected material may partially or completely compress interior 308.

Feedback

At 138, feedback is optionally provided to an operator, to decide if injection is completed. Optionally, feedback is provided by fluoroscopic imaging of the site. However, other imaging methods may be used.

Optionally, non-imaging feedback is provided, for example a pressure inside the vertebra, using a pressure sensor (not shown), or using an indicator (visual or audio) for the amount of material injected.

Optionally, the feedback is used to decide if the procedure is progressing as desired, e.g., desired amount of height restoration (if any), verify a lack of material leakage, determine symmetry or asymmetry and/or the presence of new fractures in bone.

Repeat and/or Change

Optionally, the material is provided in a magazine having a fixed amount (described below). If that magazine is finished and additional material is required, a refill may be provided (140), for example by replacing the magazine with a new one.

Optionally, a property of the delivery of material is changed, for example one or more of a delivery pressure, a delivery rate, an amount of delivery when delivery is in discrete units, a viscosity, composition and/or type of the delivered material, a pre-heating or pre-cooling of the material, a location of provision inside the vertebra, a spatial pattern of provision and/or a direction of provision in the vertebra.

Optionally, the direction of provision of the material is changed (142), for example, to assist in maintaining symmetry of lifting or to point in the injection of material away from a fracture or towards an empty space. Optionally, the direction of provision is changed by rotating delivery system 314. Alternatively or additionally, injection is continued through a new access hole in the vertebra. Optionally, the cannula is moved axially.

Optionally, a different material is used to top off the procedure, for example, a cement which sets to a hardened condition (e.g., PMMA) is used to seal the entry hole and/or stiffen the non-hardening material (144).

Complete Procedure

Figure 3F:
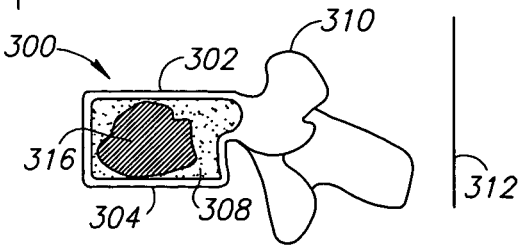

At 146, the tools are removed. FIG. 3F shows vertebra 300 after the procedure is completed. Optionally, the entry incision is sealed, for example, using tissue glue or a suture.

Exemplary Basic Delivery System

Figure 4A:
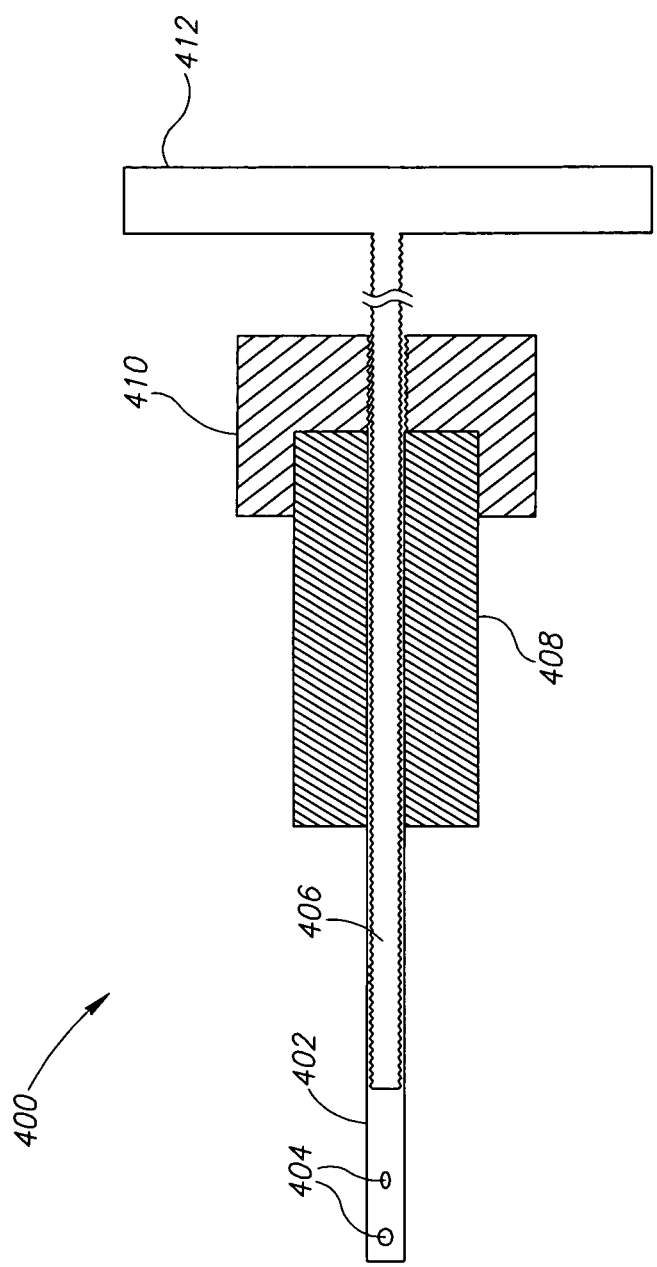
FIGS. 4A and 4B illustrate basic material delivery systems, in accordance with exemplary embodiments of the invention.
Figure 4B:
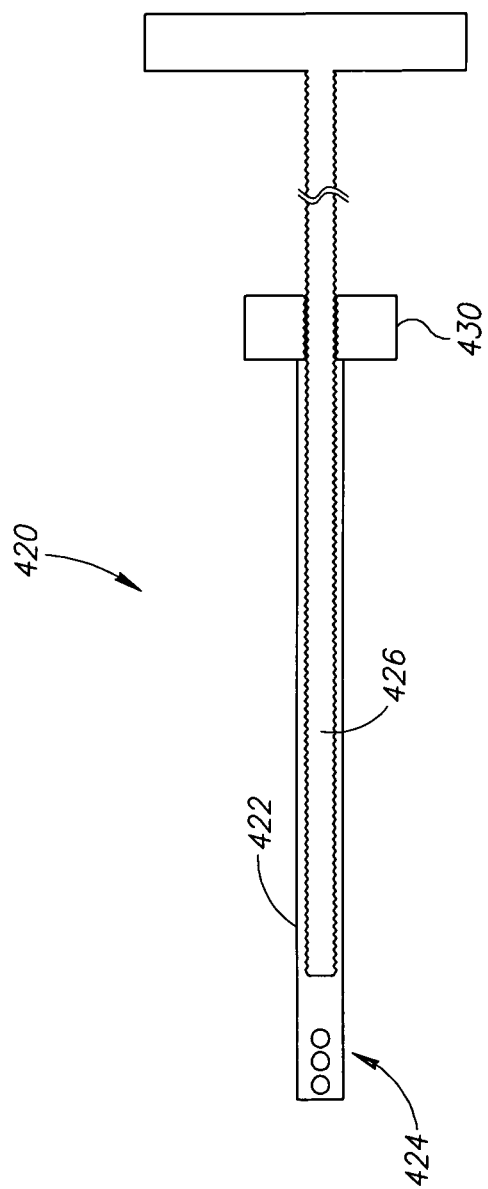

FIGS. 4A and 4B illustrate basic delivery systems, in accordance with exemplary embodiments of the invention FIG. 4A is a cross-sectional view of a delivery system 400, comprising generally of a delivery tube 402 having one or more extrusion apertures 404. Optionally, the distal end of tube 402 is sealed. Alternatively it may be at least partially open, so forward injection of material is provided. It is noted that when the end is sealed, there may be less force acting to retract the delivery system from the vertebra. Material inside tube 402 is advanced by a threaded pusher 406.

In the design shown, tube 402 is attached to a barrel 408 with a permanent or temporary attachment method. Threading (not shown) may be provided inside of barrel 408, to match the threading on pusher 406. Alternatively (not shown), the inner diameter of barrel 408 is greater than that of tube 402. Optionally, barrel 408 and/or tube 402 serve as a reservoir of material.

A body 410 which acts as a nut and includes an inner threading engages pusher 406. In an exemplary embodiment of the invention, when a handle 412 of pusher 402 is rotated (while holding on to body/nut 410), pusher 406 is advanced, injecting material out of apertures 404 into the body. Optionally, barrel 408 is detachable from body 410, for example, for replacing barrel 408 with a material-filled barrel, when one barrel is emptied. The coupling can be, for example, a threading or a quick connect, for example, a rotate-snap fit. Optionally, tube 402 is detachable from barrel 408, for example using the same type of coupling.

In an exemplary embodiment of the invention, when the distal tip of pusher 406 goes past apertures 404 (in embodiments where it is that long), the passage cuts the material in front of the pusher away from the material exiting the aperture, releasing the exiting material from the delivery system.

FIG. 4B shows an alternative embodiment of a delivery system, 420, in which a different design of apertures 424 is used. In the embodiment, a delivery tube 422 serves as a barrel and storage for the material and is optionally detachable from a threaded nut body 430. Optionally, tube 422 is long enough to include an amount of material sufficient for injection, for example, 8-10 cc. Optionally, body 430 includes a pistol or other grip (not shown) and, as above, may be threaded to engage a pusher 426.

In an exemplary embodiment of the invention, the delivery system is made of metal, for example, stainless steel. Alternatively or additionally, at least some of the components are made of a polymer material, for example, PEEK, PTFE, Nylon and/or polypropylene. Optionally, one or more components are formed of coated metal, for example, a coating with Teflon to reduce friction.

In an exemplary embodiment of the invention, the threading of the pusher is made of Nitronic 60 (Aramco) or Gall-Tough (Carpenter) stainless steels.

In an exemplary embodiment of the invention, instead of a standard threading, a ball screw is used. Optionally, the use of a ball screw increases energy efficiency and makes operation easier for manual systems as shown in FIGS. 4A and 4B. Optionally, a gasket is provided to separate the balls from the material.

In an exemplary embodiment of the invention, the delivered material is provided as an elongate sausage with a diameter similar to that of the delivery tube and/or aperture(s). Optionally, a long delivery tube is provided. Alternatively, a plurality of such strings/sausages are implanted. Optionally, the material is provided in a diameter smaller than that of the delivery tube, for example, 0.1-0.01 mm smaller so that there is reduced friction.

Exemplary Extrusion Details

Referring back to FIG. 4A, it is noted that the more proximal extrusion aperture 404 is optionally smaller than the more distal one. Optionally, the relative sizes are selected so that the extrusion rate and/or forces at the two holes is the same. Alternatively, the holes are designed so that the rates and/or forces are different. Referring to FIG. 4B, three axially spaced apertures may be provided and the profile of extrusion can be that a greatest extrusion and/or force is applied at the middle hole.

In an exemplary embodiment of the invention, the sizes of apertures are selected so that the total amount of material ejected is as desired, taking into account the possible sealing of some of the apertures by the advance of the pusher.

In an exemplary embodiment of the invention, the apertures are designed so that the extruded material is ejected perpendicular to the delivery system. Optionally, the delivery system is shaped so that the ejection is at an angle, for example, an angle in the plane of the axis and/or an angle in a plane perpendicular to the axis. Optionally, the angle is selected to offset forces which tend to push the delivery system out of the vertebra. Alternatively or additionally, the angle is selected to match a desired lifting direction of the vertebra or, for example, to prevent direct lifting by the extruded material. Optionally, the delivery system is inserted at a desired angle into the vertebra. Optionally, the angles of different apertures, for example, apertures on opposite sides of the delivery tube, are different, for example, defining a 180 degree angle between the apertures on opposite sides or a more acute (towards the proximal side) or oblique angle.

In an exemplary embodiment of the invention, the extrusion angle is 30 degrees, 45 degrees, 60 degrees, 80 degrees or smaller, intermediate or larger angles to the tube axis. Optionally, the material is extruded with a bend radius of 1 mm, 2 mm, 3 mm, 4 mm, 5 mm, 10 mm or intermediate, smaller or larger radii.

The radial arrangement of the extrusion apertures can be of various designs. In one example, for example to ensure even filling of space 308, three, four or more axial rows of apertures are provided. Each row can have, for example, one, two, three or more apertures. In another example, apertures are provided only on opposing sides, so that, for example, a user can select if to extrude towards cortical plates 302 and/or 304, or not.

Rather than rows, a staggered arrangement may be used. One possible advantage for a staggered arrangement is that the delivery tube may be overly weakened by aligned rows of apertures.

Figure 5A:
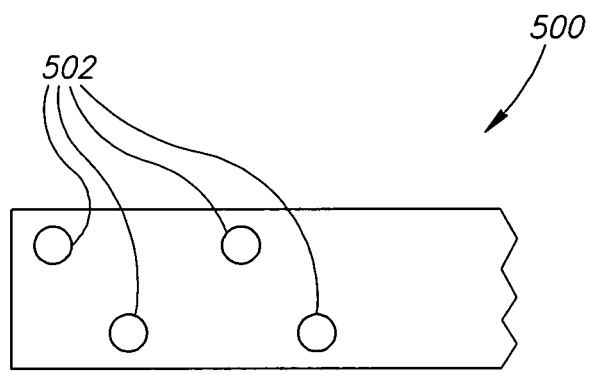
FIGS. 5A and 5B show details of material extruder tips, in accordance with exemplary embodiments of the invention.
Figure 5B:
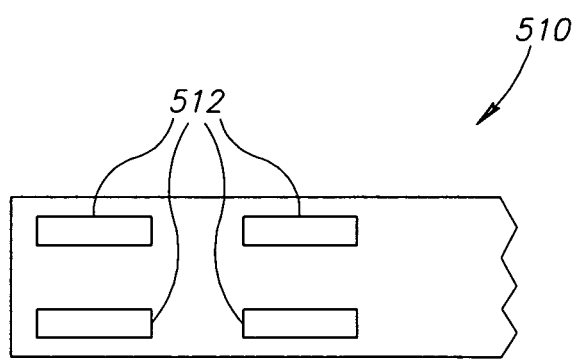

FIG. 5A shows a design of a delivery tip 500 in which round apertures 502 in a staggered row design are used. FIG. 5B shows a design of a delivery tip 510 in which elongated rectangular apertures 512 are arranged in a non-staggered manner.

As shown, the shape of the apertures can be various, for example, round, ellipsoid, rectangular, axially symmetric or asymmetric, parallel to the tube axis or not and/or elongate. Optionally, the edges of the apertures are jagged. Optionally, the shape of the apertures is selected for one or more of the following reasons: shape of extrusion, preventing failure of the aperture and/or preventing failure of the delivery tip. Optionally, the apertures have a lip (optionally pointing inwards), which may assist in shaping the extrusion. For example, the lip may be between 0.1 and 1 mm in width, for example, 0.3 mm or 0.5 mm.

In an exemplary embodiment of the invention, the delivery tube is rigid. Optionally, the delivery tube is flexible or is mechanically shaped (e.g., using a vise) before insertion. In an exemplary embodiment of the invention, the cannula is flexible and allows the insertion of a delivery tube which is curved at its end.

In an exemplary embodiment of the invention, the type of delivery tip used is selected by a user. Optionally, the delivery tip is replaceable, for example attached by a threading to the delivery system.

Optionally, an overtube or ring is selectively provided over part of the delivery system to selectively block one or more of the apertures.

Figure 7A:
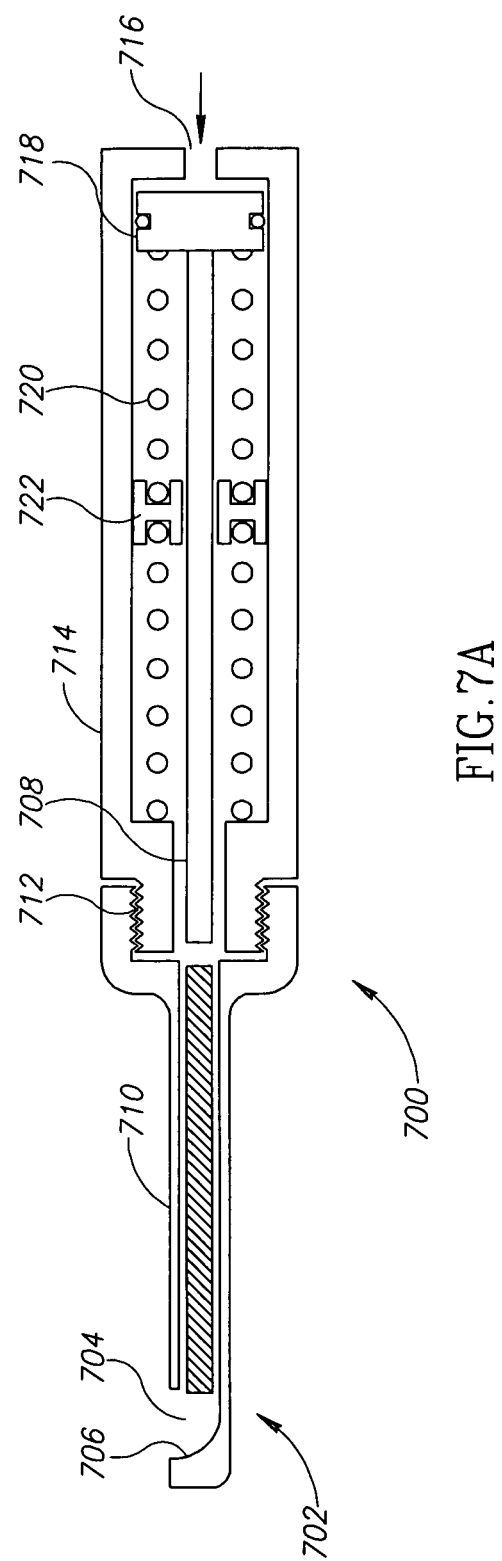
FIG. 7A illustrates a hydraulic delivery system, in accordance with an exemplary embodiment of the invention.

Referring briefly to FIG. 7A, a delivery tip 702 is shown, in which a guiding incline 706 is provided to guide the ejected material out of an aperture 704. Optionally, the use of such an incline reduces turbulence in the flow/distortion of the material and/or may assist in reducing friction and/or improving control over the shape of the extrusion. Also to be noted is that material extrusion is provided on only one side of the delivery system. This may allow better control over the force vectors inside the vertebra, caused by the extrusion. In an exemplary embodiment of the invention, the angles defined by the guiding incline (90 degrees and in the plane of the tube axis) help determine the extrusion direction.

Also shown in FIG. 7A is a non-twisting pusher 708, which may reduce turbulence, friction and/or other difficulties in extruding the material, such as voids.

Figure 5C:
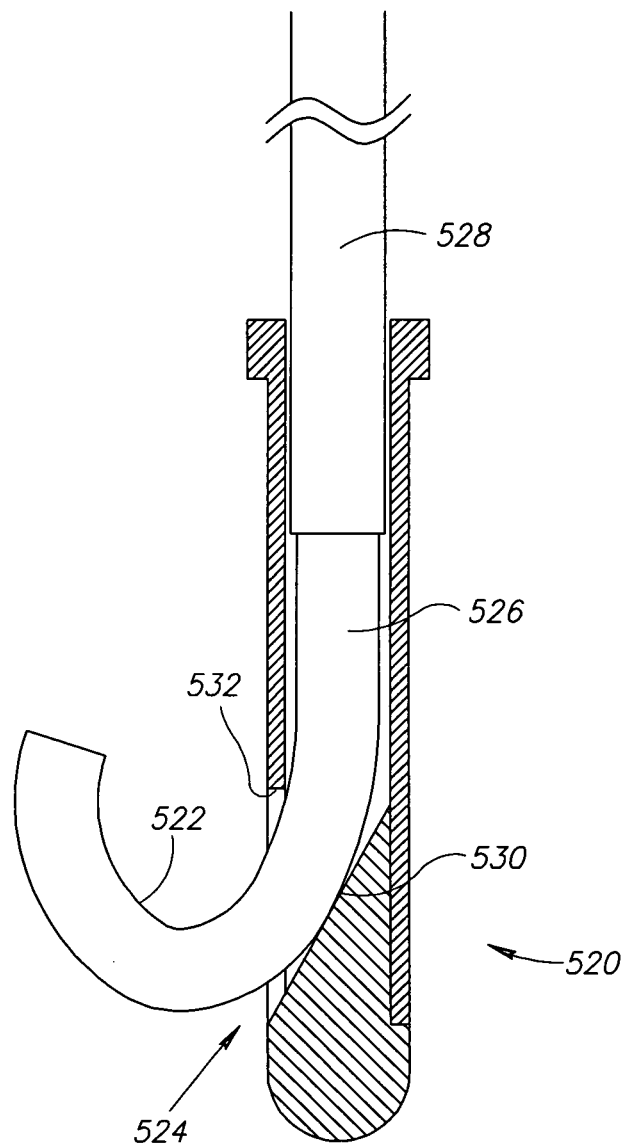
FIG. 5C shows an elongated and curved extrusion of material, in accordance with an exemplary embodiment of the invention.

FIG. 5C shows a delivery tip 520, from which a material 526 is extruded by a pusher 528 in a curved extrusion shape 522. In an exemplary embodiment of the invention, the curvature is controlled by controlling the relative friction on a proximal side 532 and on a distal side 530 of an aperture 524. Alternatively or additionally, the degree of curvature depends on the size of the aperture and the shape of the incline. Optionally, the material is plastically deformed by the extrusion and may maintain a shape conferred thereby barring contact with a deforming surface (e.g., a bone plate).

Alternatively or additionally, extrusion 522 can be curved or bent due to axial or rotational motion of tip 520. Optionally, the rotation is used to more uniformly fill space 308.

In an exemplary embodiment of the invention, the delivery tube moves and/or rotates during delivery. Optionally, a gear mechanism couples movement of the pusher with rotation and/or axial motion of the tube. Optionally, a manual motion is provided by an operator. Optionally, a vibrator is coupled to the delivery system.

Figure 6C:
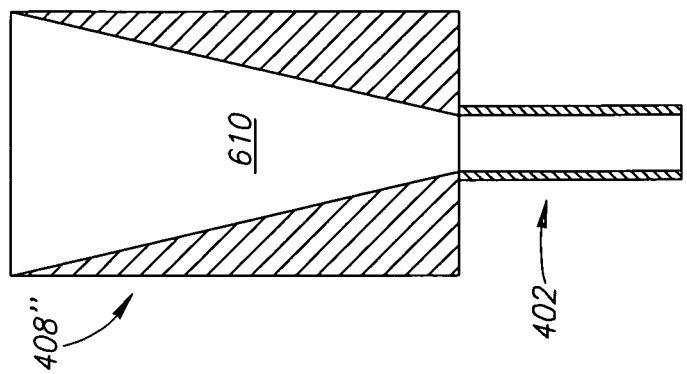
FIGS. 6A-6C illustrate narrowing lumen sections of a delivery system, in accordance with an exemplary embodiment of the invention.

One consideration mentioned above, is that the amount of material in barrel 408 may not be sufficient for a complete procedure. A matching design is illustrated in FIG. 6A, in which the diameter of an inner lumen 602 of barrel 408 is the same as the diameter of an inner lumen 604 of delivery tube 402. A longer delivery tube/barrel maybe required to reduce the number of barrel changes.

Figure 6B:
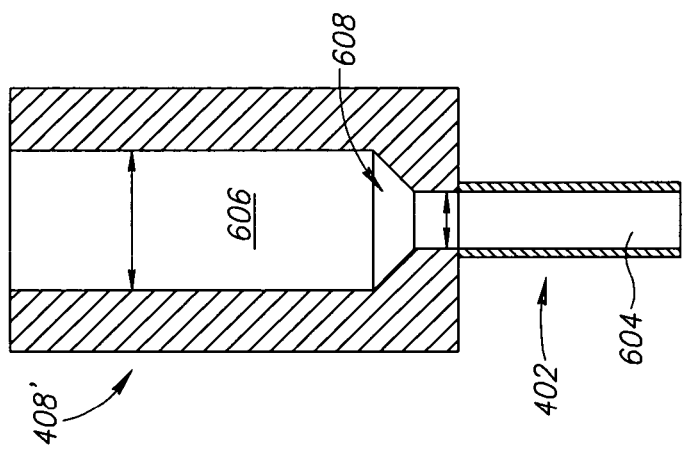
Figure 6A:
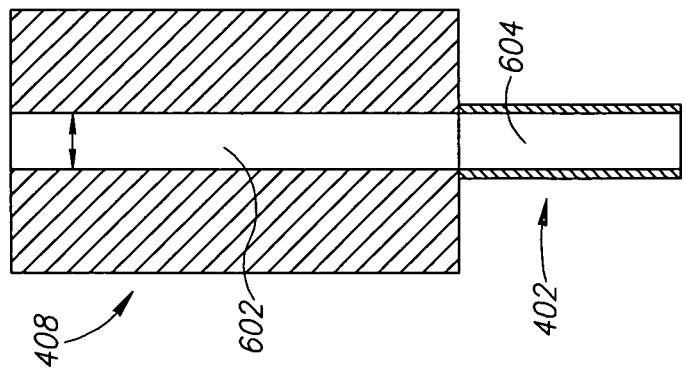

FIG. 6B shows an alternative design, in which a barrel 408' has a lumen 606 with a greater inner diameter and thus a greater storage volume. Optionally, the greater diameter provides an additional hydraulic amplification factor as the diameter changes. Optionally, a sudden change in diameter may cause turbulence, resistance and/or void creation. In some materials, diameter change requires compression of the material. Optionally, as shown, a gradual change in diameter is provided, with an intermediate sloped section 608 with an inner diameter varying between the diameters of lumen 606 and 604. Optionally, the pusher has a diameter matching lumen 606 and does not fit into lumen 604. Optionally, an extension is provided to the pusher, which extension does fit in lumen 604.

Referring to FIG. 6C, a gradually changing lumen 610 is provided in a barrel 408". Optionally, the distal end of the pusher is made of a flexible material, which can conform to the change in diameter. Optionally, the flexible material is harder than the injected material. Alternatively or additionally, the distal end of the pusher is shaped to match the geometry of lumen 610.

In an exemplary embodiment of the invention, the lumen of the barrel is larger than the diameter of the pusher, at least in a proximal section of the barrel. After the pusher advances an amount of material into the bone, the pusher is retracted and the material remaining in the barrel is rearranged so that the next advance of the pusher will advance it. Optionally, the rearranging is by advancing a second plunger having a diameter similar to that of the barrel. Optionally, this plunger is coaxial with the pusher.

The delivery tube may have various cross-sectional shapes, for example, circular, rectangular, arcuate and/or square. Optionally, the cross-section is matched to the shape of extrusion apertures. Optionally, the inside of the apertures is made sharp to cut the extruded material as it is advanced, instead of or in addition to plastically deforming or shearing it.

Exemplary Viscosity/Plasticity and Pressure

In an exemplary embodiment of the invention, the provided material has a viscosity of above 600 Pascal-second. Optionally, the material is advanced into the body using a pressure of at least 40 atmospheres or higher, for example, 100 or 200 atmospheres or more. If the material is plastic, it may have a hardness, for example, of between 10A shore and 100A shore.

In an exemplary embodiment of the invention, pressure requirements are relaxed at a beginning of a procedure, for example, if a void is created by bone access or by rotation of the delivery system.

In an exemplary embodiment of the invention, the outer diameter of the delivery system is, for example, 2 mm, 3 mm, 4 mm, 5 mm or intermediate or smaller or larger diameters. Optionally, the wall thickness of the delivery system is 0.2 or 0.3 mm. Optionally, the wall thickness increases towards the distal tip.

It should be noted that the pressure used for delivery may depend on one or more of: the friction between the material and the delivery system, the length of material being pushed, the pressure applied to the material, the pressure desired to be applied by the material to the vertebra, the manner in which the extrusion applies pressure against the vertebra, the viscosity of the material and/or other causes of resistance to motion of the material.

Lower pressures may be used, for example, if it is deemed that the vertebra may be damaged or material leakage possible.

The volume injected may be, for example, 2-4 cc for a typical vertebra and as high as 8-12 cc or higher. Other volumes may be appropriate, depending for example, on the volume of space 308 and the desired effect of the injection.

In an exemplary embodiment of the invention, the rate of injection is 0.25 cc/sec. Higher or lower rates may be provided, for example, between 25 cc/sec and 0.1 cc/sec or less, and between 25 cc/sec and 1 cc/sec or more. Optionally, the rate is controlled using electronic or mechanical circuitry. Optionally, the rate is decided by an operator responsive to expected or imaged bone deformation in response to the pressure. Optionally, the rate is changed over the length of the procedure, for example, being higher at a beginning and lower at an end. Optionally, the rate of injection is controlled by the operator (or automatically) responsive to a feedback mechanism, such as fluoroscopy.

Hydraulic Material Provision System

FIG. 7A shows a delivery system 700 which is powered hydraulically. A delivery tube 710 is filled with material to be ejected into the body. Tube 710 is optionally detachable via a connection 712 to a body 714. Optionally, the connection is by threading. Alternatively, a fast connection method, such as a snap connection, is used.

Body 714 converts hydraulic pressure provided via an input port 716 into an advance of a pusher rod 708. Optionally, body 714 is integral with tube 710, but this prevents replacing tube 710 when the material to be ejected is exhausted.

In an exemplary embodiment of the invention, incoming hydraulic (or pneumatic) fluid pushes against a piston 718, which advances pusher 708 directly. Optionally, a hydraulic advantage is provided by the ratios of the piston and the pusher. Optionally, a spring 720 is provided for retracting pusher 708 when the fluid pressure is released.

Optionally, one or more spacers 722 are provided surrounding pusher 708, to prevent buckling thereof. Optionally, the spacers are mounted on spring 720. Optionally, spacers are provided at several axial locations. Alternatively to spacers, fins may extend from pusher 708 to body 714.

Optionally, in use, when material is used up, pressure is reduced, pusher 708 retracts and delivery tube 710 is replaced. Optionally, a barrel filled with material for injection, separate from tube 710 is provided, so that tip 702 does not need to be removed from the body.

Figure 7B:
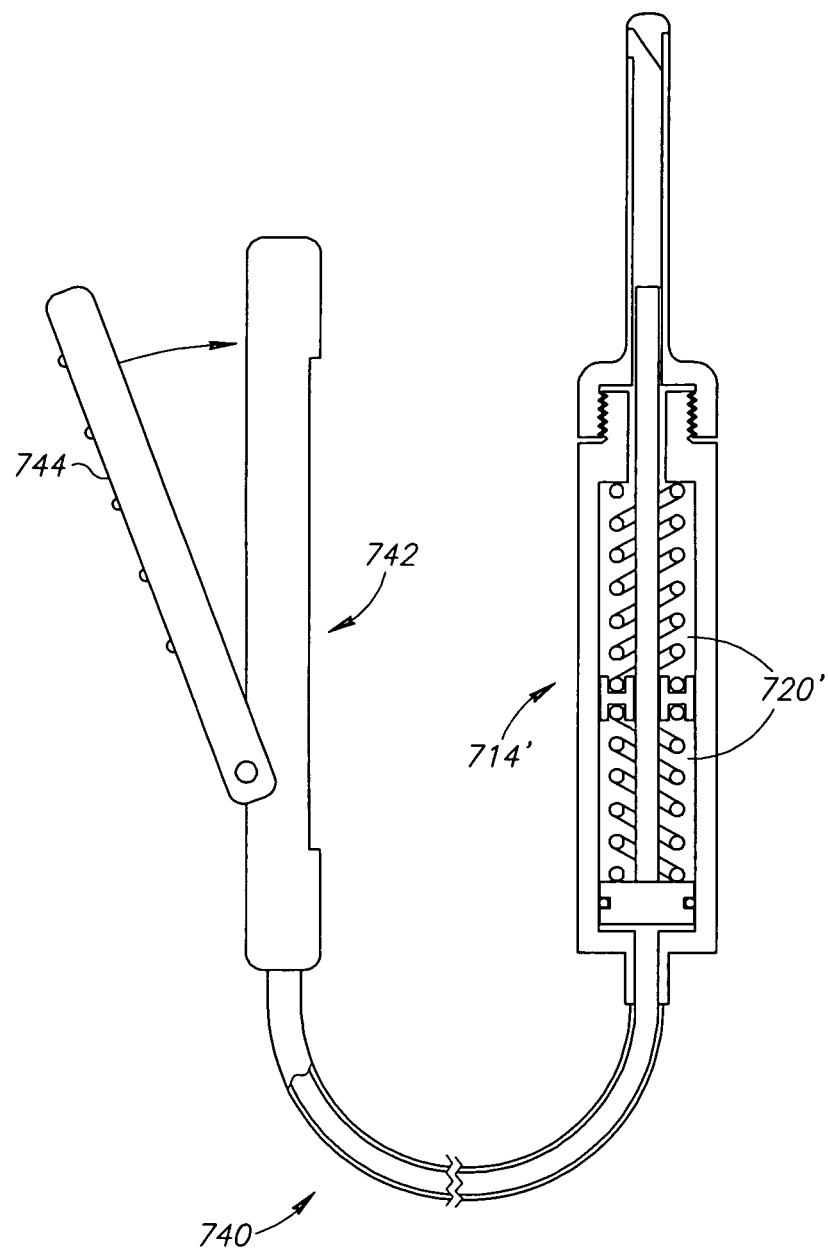
FIGS. 7B and 7C show alternative methods of providing hydraulic power to the system of FIG. 7A, in accordance with exemplary embodiments of the invention.
Figure 7C:
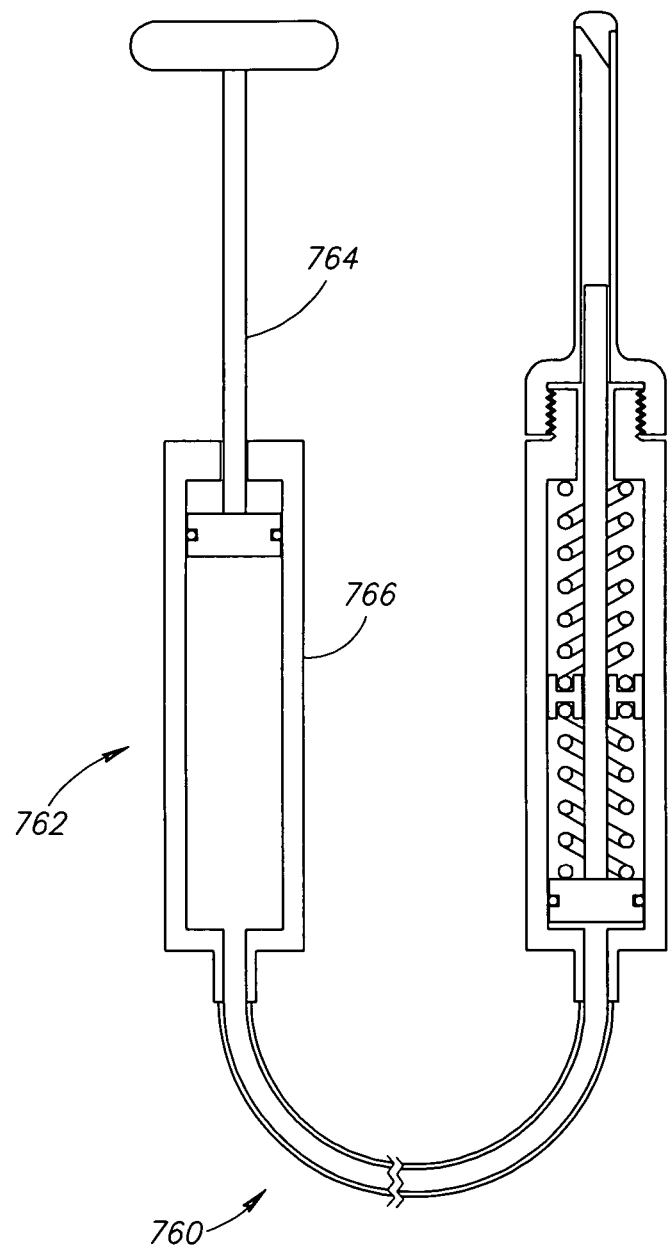

FIGS. 7B and 7C show two alternative methods of providing hydraulic power. In FIG. 7B, a foot pedal pump 740 is used, in which a user places his foot on a pedal 744 and depresses it against a plate 742. Various foot pumps are known in the art. Optionally, a long press releases the pressure. Optionally, the hydraulic subsystem is a sealed system which is provided ready to use (e.g., including fluid) to the user and/or distributor. Exemplary lengths of the flexible tubing are between 0.2 and 3 meters, for example, between 1 and 2 meters. However, greater lengths can be used as well.

Also shown in FIG. 7B is a variant of body 714, indicated as 714'. Instead of a single spring 720, two springs 720' are shown, with the spacer(s) between the springs. Optionally, the use of multiple springs helps maintain the spacers near a middle (or other relative length unit) of the pusher in danger of buckling.

FIG. 7C shows an alternative embodiment, in which a hand pump 760 is used, which pump can be of any type known in the art, for example, a mechanism 762 comprising a piston 764 and a cylinder 766. Optionally, the pumping is by rotating piston 764 elative to cylinder 766, which components include matching threading. Alternatively, linear motion is used. Optionally, a hydraulic gain is achieved between the pump and the delivery mechanism, for example a gain of 1:3, 1:5, 1:10 or any smaller, intermediate or greater gain.

In an exemplary embodiment of the invention, the hydraulic system is provided as a disposable unit, with a non-disposable (or a disposable) foot pump.

Figure 7D:
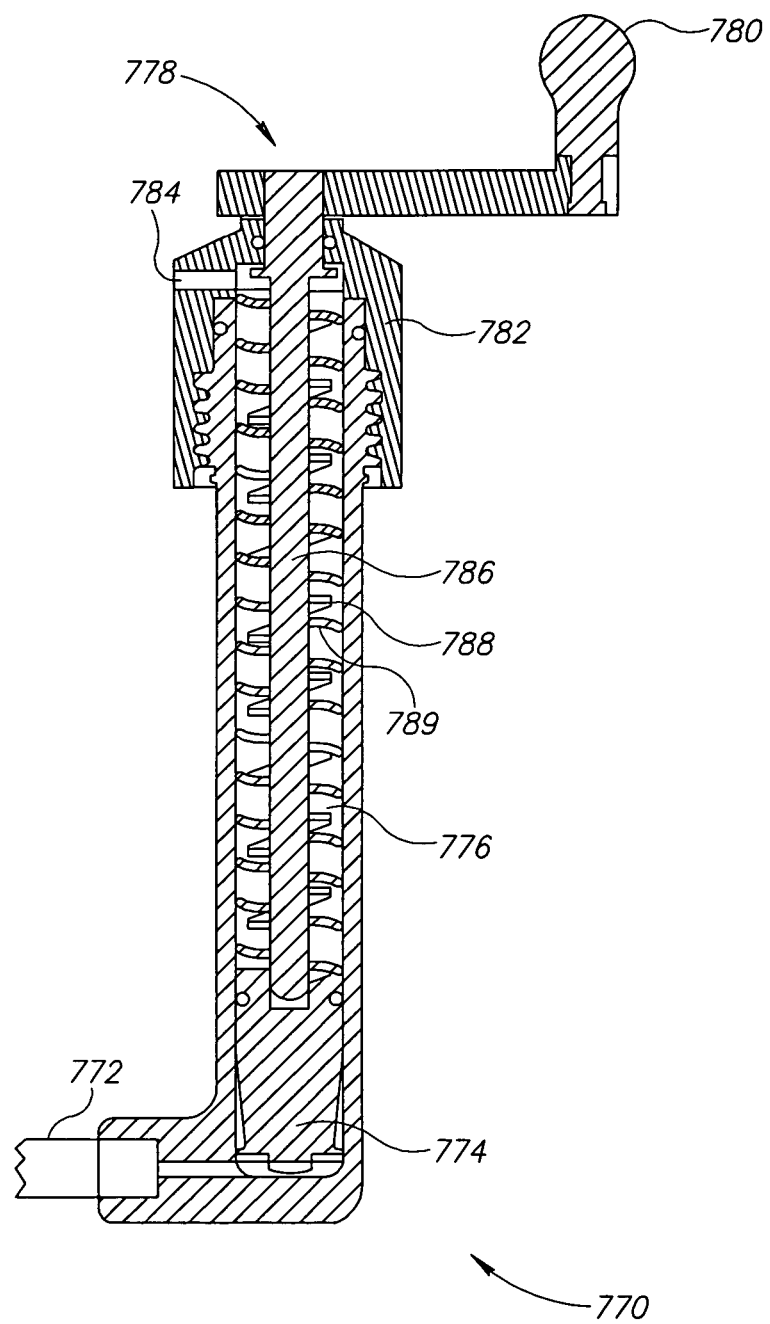
FIGS. 7D and 7E illustrate an exemplary hydraulic system including a disposable unit, in accordance with an exemplary embodiment of the invention.
Figure 7E:
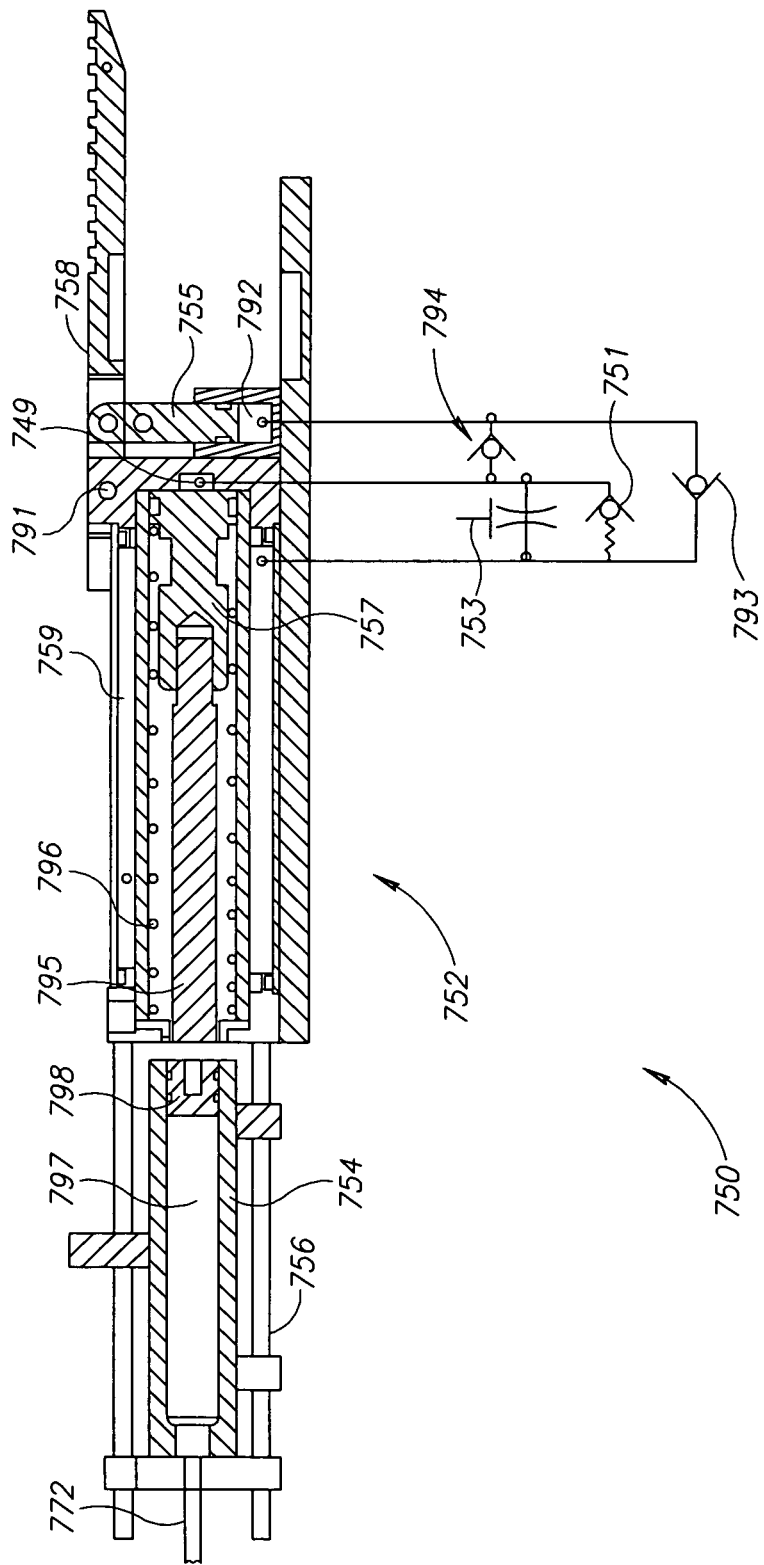

FIG. 7D shows a disposable mixing and storage chamber 770 and FIG. 7E shows a reusable pump 750 with a disposable hydraulic capsule 754.

Referring to FIG. 7D, a same capsule 770 is optionally used both for mixing and for storage/delivery of a material. Optionally, the material is a setting cement such as PMMA. In the embodiment of a hydraulic delivery stream, a flexible tube 772 is optionally permanently connected to a pump (FIG. 7E). When fluid is provided through tube 772, a piston 774 moves through a cylinder volume 776 and pushes the material out (e.g., and into a delivery system). In the figure, the capsule is shown loaded with a mixer 778. Optionally, materials are provided into volume 776 using a detachable funnel (not shown) and then the funnel is removed and mixer 778 inserted instead. In the exemplary mixer shown, a cap 782 covers cylinder 776. When mixing is completed, this cap may be replaced by a fitting adapted to couple to the delivery tube.

In use, a handle 780 is rotated, rotating a shaft 786 having a rotor 788 defined thereof, for example, as a helix. An optional stator 789 is provided. An optional vent 784 may be connected to a vacuum source, to suck out toxic and/or bad smelling fumes caused by the setting of the material. Optionally, a viscosity of the materials is estimated by the difficulty in turning the handle. Optionally, the handle includes a clutch (not shown) that skips when a desired viscosity is reached. Optionally, the clutch is settable. Optionally, a viscosity meter is used or viscosity is estimated based on temperature, formulation and time from mixing.

Cap 782 optionally includes a squeegee or other wiper, to wipe material off of mixer 778 when it is removed from capsule 770.

Referring to FIG. 7E, tube 772 connects to a capsule 754 which includes a piston 798 and a volume 797, pre-filled with fluid. In an exemplary embodiment of the invention, a frame 756 is provided attached to pump 750 for selectively receiving capsule 754.

Pump 750 is, for example, a hydraulic oil based pump-mechanism 752 that extends a pushing rod 795 which advances piston 798.

In the embodiment shown, a foot pedal 758, attached to an axis 791, forces a piston 755 into a cylinder 792. A one way valve 794 allows the fluid in cylinder 792 to flow into a volume 749 where it pushes against a piston 757. When pedal 758 is released, a spring (not shown) pulls it back to an upward position and allows a hydraulic fluid to flow from a storage chamber 759 (e.g., which surrounds the pump) through a one way valve 793 into cylinder 792.

A pressure relief valve 751 is optionally provided to prevent over pressurizing of cylinder 749. In an exemplary embodiment of the invention, a spring 796 is provided to push back piston 757 and pusher 795 with it, when pressure is released. Optionally, pressure is released using a bypass valve 753, which is manually operated. Once pusher rod 795 is retracted, capsule 740 is optionally removed.

Unit Material Provision System

Figure 8A:
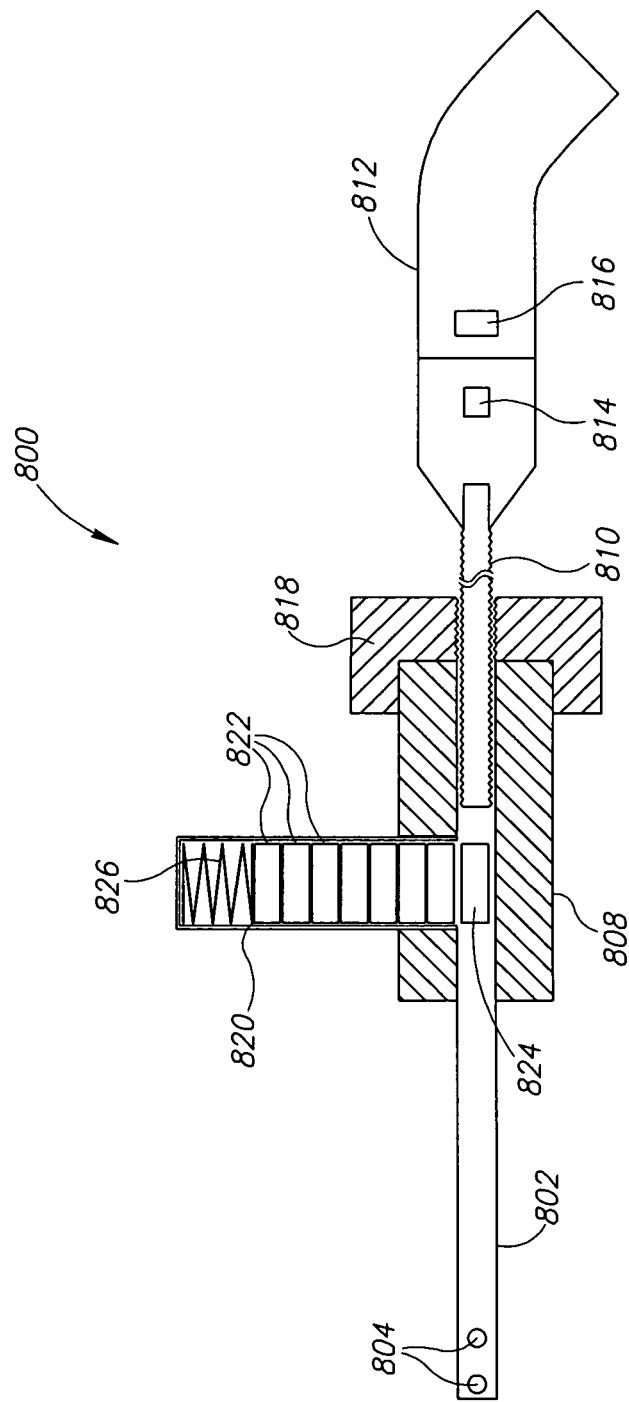
FIG. 8A shows a cassette based delivery system, in accordance with an exemplary embodiment of the invention.

FIG. 8A shows a delivery system 800 in which material is provided as discrete units, each of which is of relatively small volume, for example, ½, ¼, ⅐, ⅙ or less of the amount required for treatment. One potential advantage of working in units is that an operator is more aware of the effect of his/her actions as each action can only inject one unit. Another potential advantage of working in units is that units with different material properties may be provided during a procedure. Another potential advantage is that units being small will generally exhibit a smaller friction with the delivery system.

System 800 comprises a delivery tube 802 having one or more extrusion apertures 804 at its tip. A barrel 808 on which tube 802 is mounted, also includes an optional magazine 820, described below. A body 818 with an optional nut threading is optionally attached to barrel 808. A pusher 810 lies within delivery tube 802 and/or barrel 808.

In an exemplary embodiment of the invention, a handle 812 is provided which includes a battery powered mechanism for advancing pusher 810. A hydraulic mechanism such as described above may be used instead. Optionally, one or more switches are provided, for example, an on/off switch 816 and a direction switch 814. Optionally, when pusher 810 completes its forward motion, it is automatically retracted. Optionally, only a single switch is needed, activation of which causes extrusion of one unit. In an exemplary embodiment of the invention, handle 812 is rotationally locked to body 818, for example using one or more guide pins.

In an exemplary embodiment of the invention, handle 812 comprises a motor and a battery that rotate pusher 810. An alternative mechanism is described below.

Referring to magazine 820, in an exemplary embodiment of the invention, the magazine comprises discrete units 822 of material (a unit 824 is shown inside tube 802). Optionally, a spring 826 is used to push the units towards tube 802. Optionally, the magazine is filled with a contiguous mass of material and the units are defined by the cutting action caused by pusher 810 pushing a unit of material away from the magazine.

In an exemplary embodiment of the invention, a magazine is prepared ahead of time, for example, by a manufacturer, who fills the magazine with a non-setting material.

In an exemplary embodiment of the invention, the magazine is loaded with a series of units of different properties, for example, responsive to an expected progress of a procedure, for example, first providing a soft material and then providing a harder material, or vice versa. Alternatively, a rotating magazine is used, in which a user can select which of several compartments will load barrel 808 next. This allows fine control over the injected material. In an exemplary embodiment of the invention, an operator can remove magazine 820 at any time and replace it with a different magazine. Optionally, this is done while pusher 810 is forward, so that there is no danger of backflow from the body.

Optionally, one or more of the units comprises or is an implant device (rather than an amorphous and/or homogenous mass), for example, an expanding implant or an implant whose geometry does not change. Optionally, one or more of the units comprises a cross-linked material.

In an exemplary embodiment of the invention, the delivery system used comprises two or more delivery tubes (optionally the combined geometry has a cross-section of a circle or of a figure eight). Optionally, each tube has a separate pusher mechanism and/or a separate material source (e.g., a magazine). Optionally, the two tubes are used simultaneously. Optionally, an operator can selectively use one tube. Optionally, the materials provided in each tube are components that react chemically one with another. Optionally, electronic control is provided to control the relative provision rates of the two tubes. Optionally, this allows control over the final material properties. Optionally, the use of two or more tubes allows a layered structure to be built up in the body. Optionally, one of the tubes delivers a setting material and the other tube delivers a non-setting material. In an alternative embodiment, each tube is used to provide a different component of a two component material. Optionally, the two tubes meet at their distal end, to ensure mixing of the components.

In an exemplary embodiment of the invention, the delivered material is CORTOSS by Orthovita inc. (US), a composite of Bis-GMA, Bis-EMA and TEGDMA. This material is optionally mixed along the path in the delivery tube.

In an exemplary embodiment of the invention, instead of the units being provided by a magazine or by a cutting mechanism, a partial unit behavior is provided by the motor of handle 812 stopping after every "unit" advance. Optionally, mechanical stops are provided for a hydraulic mechanism, if used. Optionally, instead of stopping, a sound is provided when a unit is injected or based on a different logic, for example, when 50% or another percentage of planned amount of material is provided. Optionally, a CPU is provided which analyzes an image provided by an imaging system and generates a signal when a sufficient and/or near sufficient and/or over-load amount of material is provided. Other circuitry may be used as well.

Optionally, circuitry is provided for controlling the rate and/or pressure of material provision. Optionally, the circuitry stops advancing if a sudden change in resistance is perceived.

In an exemplary embodiment of the invention, the delivery system includes pre-heating or pre-cooling of the injected material and/or of tube 802. In an exemplary embodiment of the invention, a Peltier cooler and/or a resistance heater are provided in barrel 808. Other cooling or heating methods, such as based on chemical reactions or phase changing materials, may be used.

In an exemplary embodiment of the invention, the magazine is a long coiled magazine. Alternatively or additionally, the deformable material is folded in the magazine. Optionally, the magazine is elongated. Optionally, separate loading and pushing mechanism are provided. In an exemplary embodiment of the invention, for loading, a unit is inserted through a slot in the side of the barrel. For pushing, the unit is advanced under a low pressure past the slot (or the slot is sealed) and only then is significant pressure required to advance the unit, for example, once the leading edge of the unit reaches the extrusion apertures.

Figure 8B:
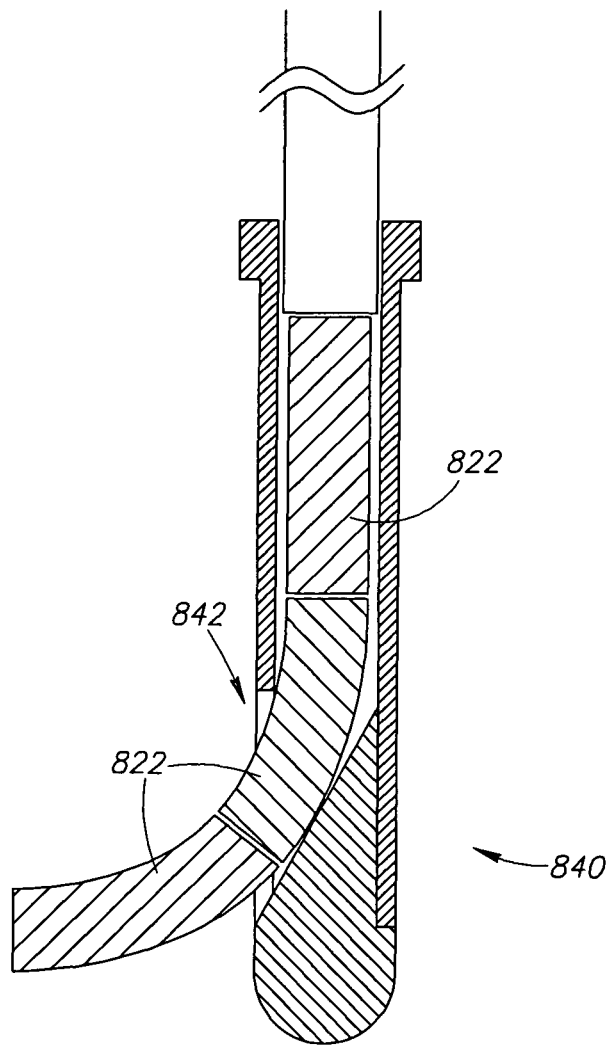
FIG. 8B is a detail showing the delivery of unit element, in accordance with an exemplary embodiment of the invention.

FIG. 8B shows the implementation of a unit delivery method even without a cassette. A delivery tip 840 is shown with an aperture 842 through which multiple units 822 are shown exiting. Optionally, an indication is provided to the user as a unit exits, for example, based on motion of a pusher used. Optionally, the system of FIG. 8A is used to load a series of units 822 into the barrel, for example, pulling back the pusher after each unit is advanced past the cassette.

Battery Powered Pusher

Figure 9A:
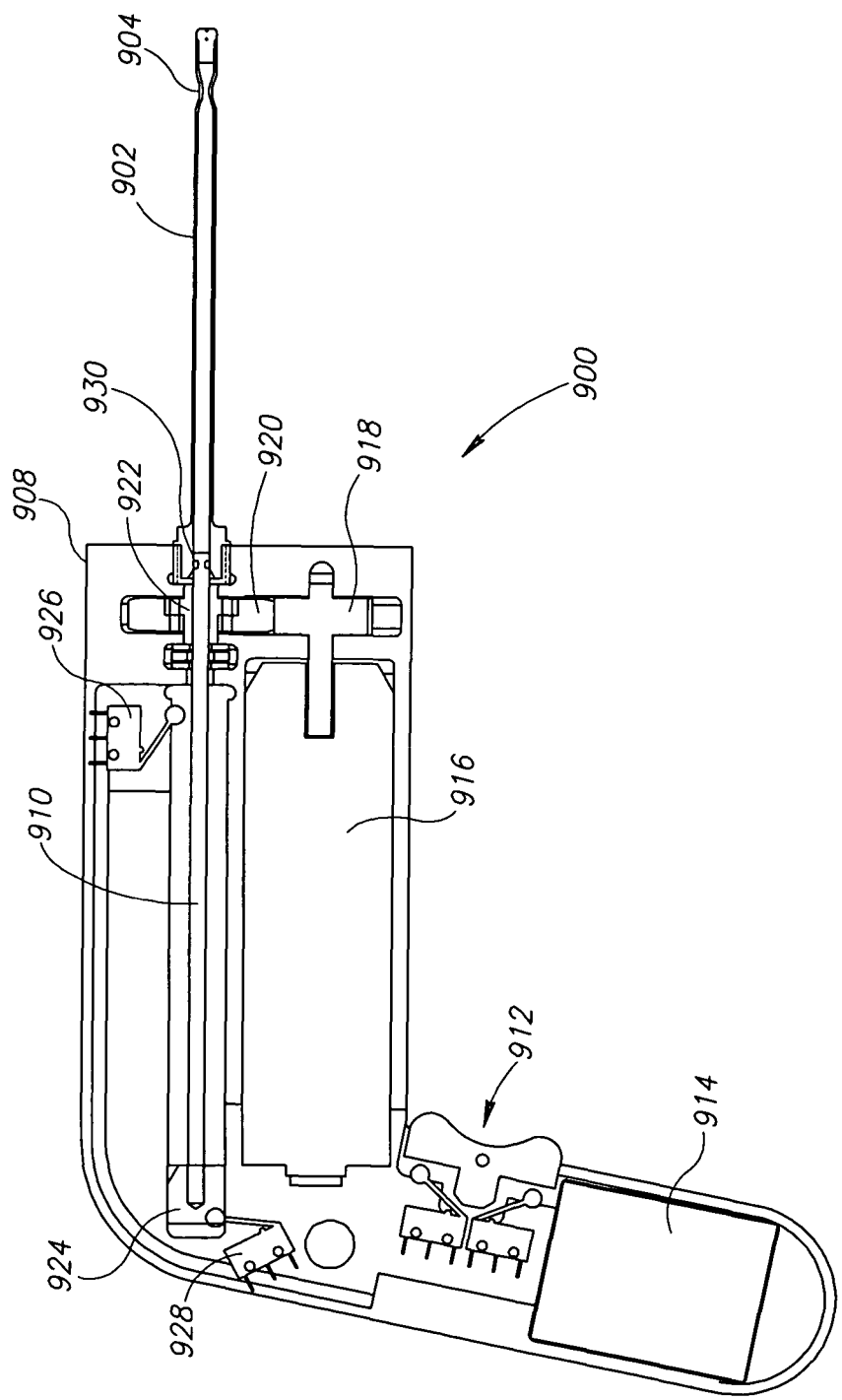
FIGS. 9A and 9B show a material pusher with reduced material twisting, in accordance with an exemplary embodiment of the invention.
Figure 9B:
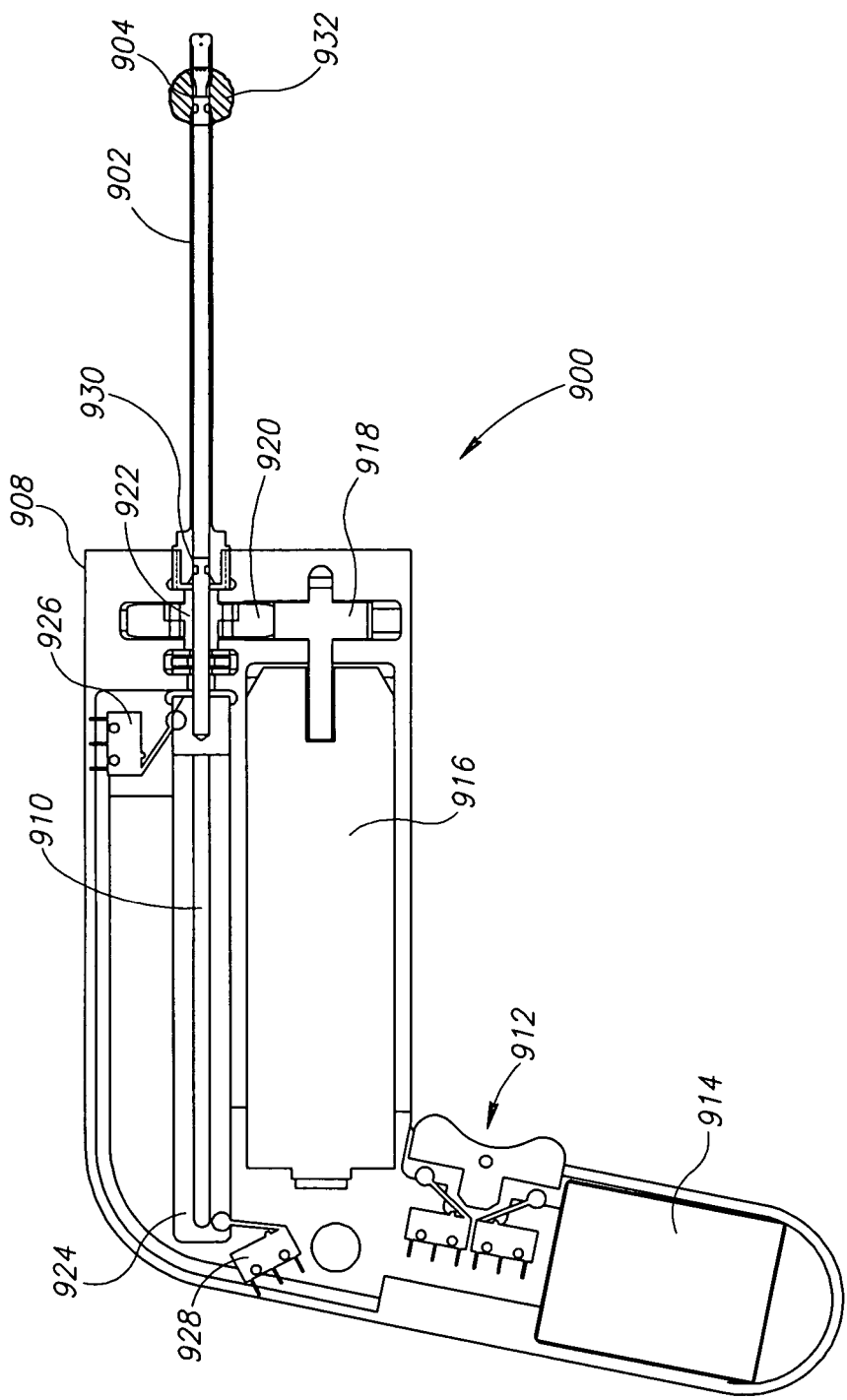

FIGS. 9A and 9B show a material pusher 900 with reduced material twisting, in accordance with an exemplary embodiment of the invention.

As in the delivery systems described above, pusher 900 comprises a delivery tube 902 having one or more apertures 904 near its end. Optionally, an offset is provided between the apertures and the far tip of tube 902, for example, to ensure centering (or other positioning) of the extruded material, for example preventing the material from being provided too close to a far end of the vertebra, if the delivery system is pushed forward.

Tube 902 is mounted (e.g., optionally replaceably) to a body 908. A pusher 910 is used to advance material through tube 902.

In an exemplary embodiment of the invention, in use, an operator presses a switch 912, for example, to select between forward, backwards and no motion of pusher 910. Power from a battery 914 (or a hydraulic or other source) is conveyed to a motor 916. Rotation of the motor causes a nut 922 to rotate relative to pusher 910. Optionally, a series of gears are used which may or may not provide a mechanical advantage, depending on the implementation. In an exemplary embodiment of the invention, motor 916 rotates a gear 918 that rotates a gear 920, which rotates nut 922 which is coaxial thereto. Optionally, a rotation preventing element 924, for example, a rectangular element 924 is mounted on pusher 910 and prevents rotation thereof.

Optionally, one or more sensors are used to detect the extremes of positions of pusher 910, when it is advanced and when it is retracted. In the example shown, a micro-switch 926 and a micro-switch 928 detect the ends of motion of pusher 910, for example, using a bump or electrically conducting section 930 (depending on the sensor type used). Alternatively or additionally, a positional encoder is used, for example, by counting rotation, or a separate encoder as known in the art of encoders.

FIG. 9B shows system 900 after extrusion is effected, showing extrusions 932. Optionally, extrusions 932 are an extension to tube 902, prior to them being cut off by pusher 910. In an exemplary embodiment of the invention, rotation of tube 902 causes extrusions 932 to act as a reamer. In an exemplary embodiment of the invention, the viscosity and shear strength of the material are selected to effect a desired limitation on the reaming abilities, for example, to prevent damage to bone.

Optionally, one or more gears are provided to rotate and/or oscillate the delivery tube as the material is advanced. Optionally, periodic or ramp axial motion is provided, by motor means. Optionally, the distal tip of the delivery tube is made soft, for example by attaching a soft tip thereto, to reduce or prevent damage to the vertebra.

Sleeve Provision System

Figure 10A:
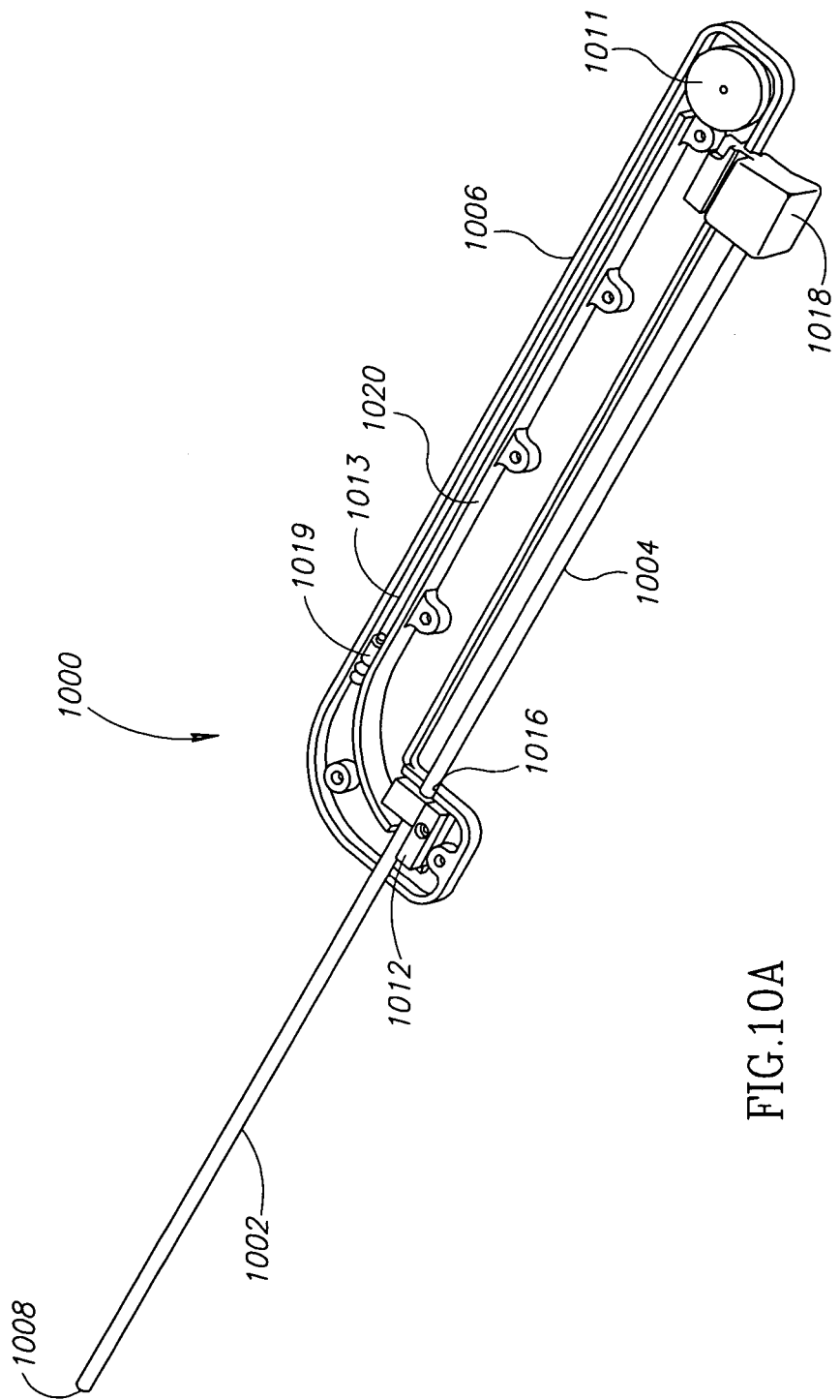
FIGS. 10A-10F show sleeve based material pushers, in accordance with exemplary embodiments of the invention.
Figure 10B:
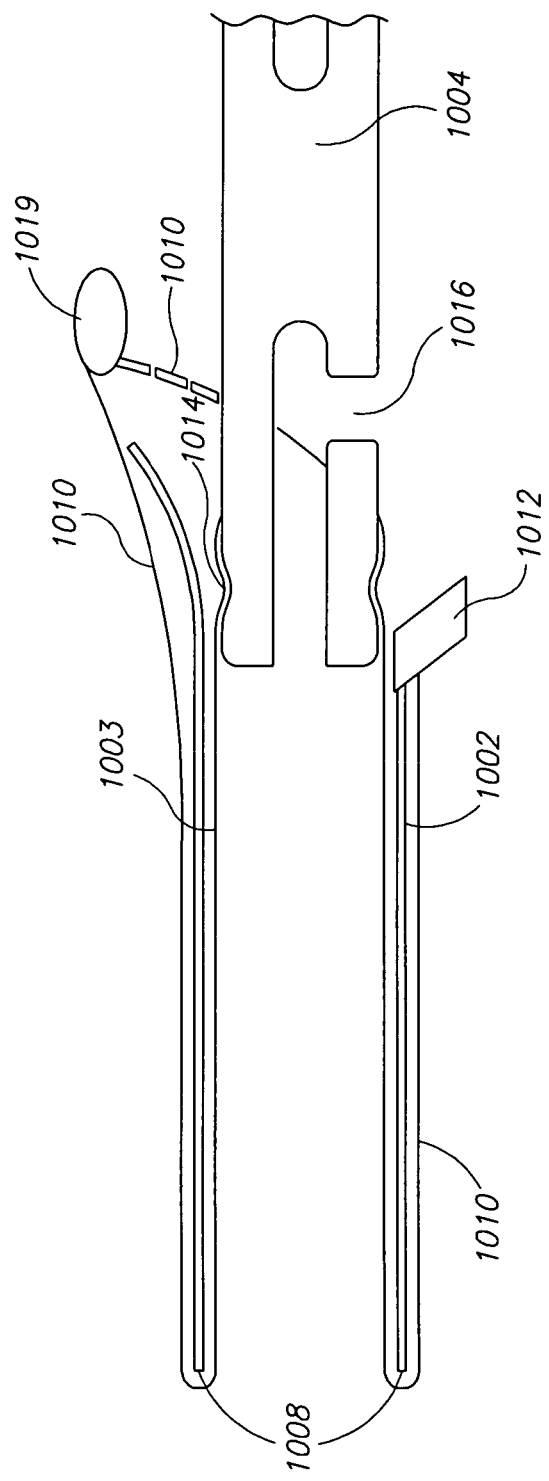

FIGS. 10A and 10B shows a sleeve based delivery system 1000, in accordance with an exemplary embodiment of the invention. FIG. 10A is a general cut-open view of system 1000, in which a sleeve 1010 is not shown. FIG. 10B shows the distal portion of system 1000, including sleeve 1010 mounted thereon.

The embodiment of FIGS. 10A-10B also illustrates a refilling mechanism by which the delivery tube includes a port to which a refill system can be connected to refill the delivery tube with material to be injected into the body.

A pusher 1004 pushes material that is found inside a delivery tube 1002. In the embodiment shown, the material is ejected past a tip 1008 of delivery tube 1002. A sleeve 1010 is provided so that the sleeve lies between the material and delivery tube 1002. An optional tube cutter 1012, such as a knife is shown to optionally split the tube after it exits the body. A pulley system 1011 for collecting the split tube is also shown.

In operation, an amount of material is either provided in tube 1002 or is injected into it, for example, via a port 1016 in pusher 1004. Advancing of pusher 1004, for example, by applying force to a knob 1018 attached thereto, for example manually, using a motor or using other mechanisms described herein, pushes against the material in tube 1002. At the same time, sleeve 1010, which is attached to pusher 1004, for example, by a crimping 1014, is pulled along with the material. Portions of sleeve 1010 reaching distal tip 1008 of tube 1002, fold back towards a body 1006 of delivery system 1000. When sleeve 1010 reaches knife 1012, it is optionally split so that it can pass over tube 1002 and pusher 1004. A thread or wire or other coupling 1013 is attached to the proximal (split) side of sleeve 1010 (e.g., via a connector 1019) and via a pulley 1011 is pulled as pusher 1004 advances. A slide 1020 is optionally provided to guide the motion of the split sleeve.

It should be appreciated that such a sleeve system can also be used for delivering implants rather than material. In one example, a compressed plastic implant, for example, polyurethane, which is compressed radially (and extended axially) is advanced using a sleeve system, to reduce friction. Optionally, the sleeve material is selected according to the material being used and/or the tube material. In another example, the sleeve system is used to deliver a self-expanding implant, for example, as described in WO 00/44319 or in WO 2004/110300, the disclosures of which are incorporated herein by reference.

It is noted that a sleeve system may also be flexible. Optionally, the sleeve is formed of a chain-link or a knitted material, rather than an extruded plastic polymer tube. Optionally, the sleeve is formed of multiple layers of materials, for example by extrusion or by lamination. Optionally, fibers or other strengthening means are provided to reduce elongation. Optionally, the sleeve is formed of a material that withstands heat and/or chemical byproducts caused by PMMA. Optionally, the sleeve is preformed to elastically expand when it exits the delivery tube. Optionally, the sleeve is perforated or includes a plurality of apertures therein.

Optionally, the sleeve elutes one or more treatment materials. Optionally, the sleeve elutes one or more catalysts or catalysis retarding materials, for example, to prevent or slow-down reactions in the delivery system and/or speed them up out of the delivery system.

Optionally, a layer of oil or other lubricant is provided in addition to or instead of the sleeve.

Optionally, the sleeve remains inside the body, for example, being formed of a bio-degrading materials or maintaining its form. Optionally, when degrading, strengthening fibers or other elements remain to enhance the strength of the extruded material or implant.

Figure 10C:
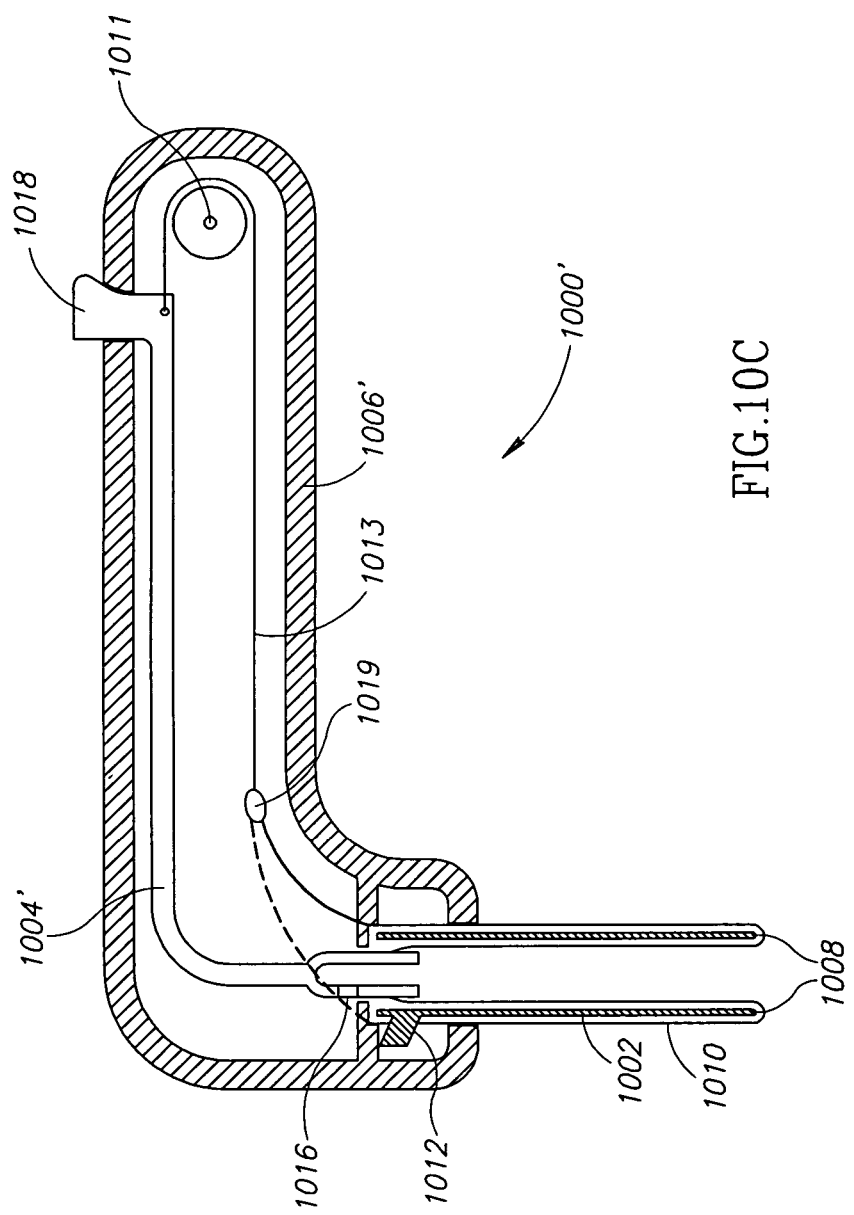

FIG. 10C is a cross-sectional view of a variant system 1000' in which a pusher 1004' is flexible enough to bend. This allows a body 1006' of the device to be manufactured in a non-linear shape, for example, in the shape of revolver, which may be easier to hold. Optionally, one or more wheels, bearings or slides (not shown) are used to guide pusher 1004'. Optionally, pusher 1004' can be made more flexible as some of the motive force used to move the material is provided by the sleeve pulling the material forward. Alternatively or additionally, some reduction is supported by the reduced friction.

Optionally, a sleeve system is used with a magazine system, for example, the units being provided through port 1016.

Optionally, the sleeve is pre-split and includes an overlap to prevent friction in the delivery tube. Optionally, this allows a magazine to load the sleeve from the side.

Figure 10D:
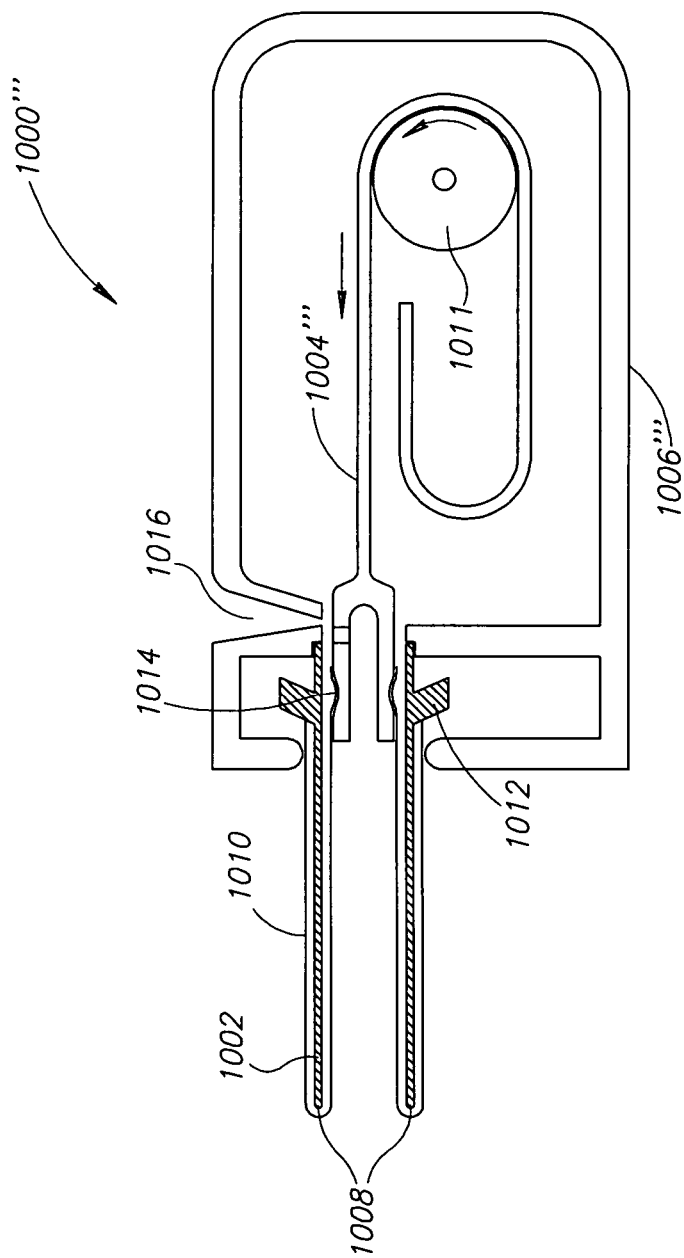

FIG. 10D shows a further, compact, variant 1000″ in which a pusher 1004″ is made flexible enough to fold over itself, so body 1006″ can be of smaller dimensions. It should be noted that these more compact and/or non-linear embodiments can also be practiced without the sleeve feature. The sleeve pullback mechanism is not shown here.

Figure 10E:
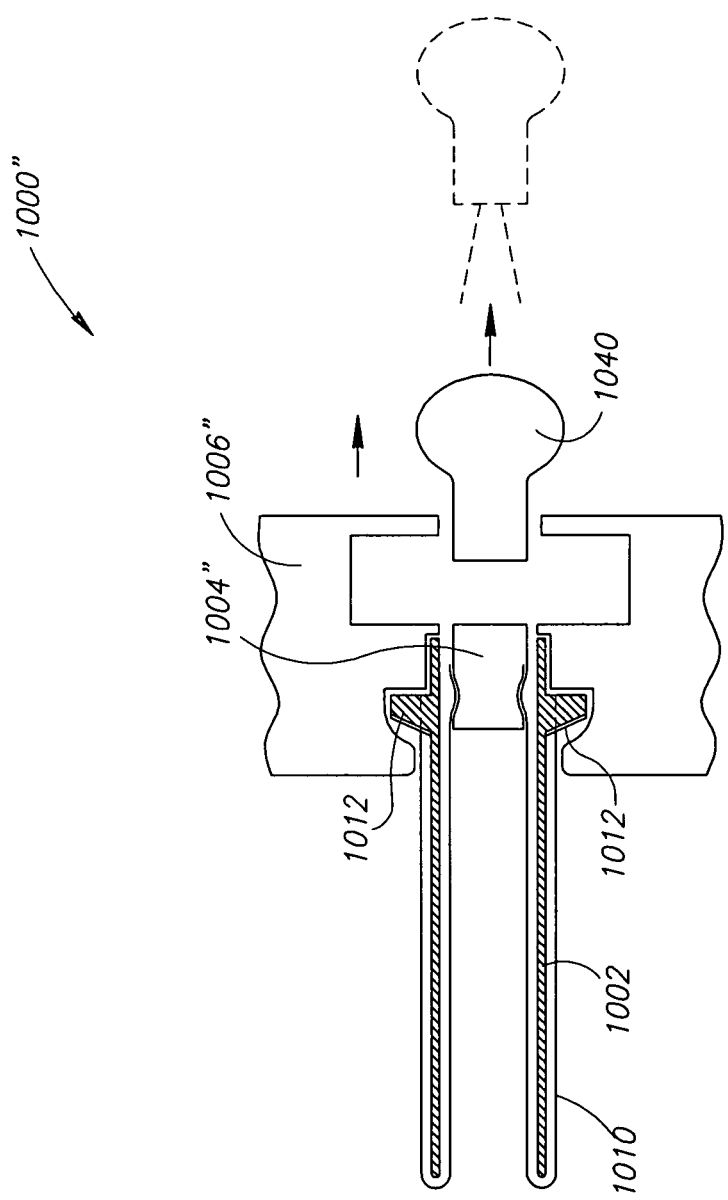

FIG. 10E shows a variant system 1000‴ in which a pusher 1004‴ is reduced in size axially. In this design the motive force is provided by pulling back the cut sleeve 1010 using a knob 1040 (or a motorized or mechanical gain or other means). This pulling back advances a shortened pusher 1004‴. Optionally, pusher 1004‴ is provided as a sealed end of sleeve 1010. A body 1006‴ of the system can be very compact, depending on the method of pulling back on knob 1040. Op two or more symmetrically positioned knifes 1012 are provided, to allow for proper mechanical support of tube 1002 by body 1006‴. Optionally, the tube is precut.

In an exemplary embodiment of the invention, it is noted that pusher 1004 is separated from the injected material by the sleeve. Optionally, a hydraulic system is used to advance the pusher, for example (in FIG. 10F) attaching a flexible tube to pusher 1004‴ in tube 1002.

In an exemplary embodiment of the invention, sleeve 1010 is used to isolate the body itself from the hydraulic system, possibly allowing for a system with a higher probability of leaking.

In the embodiments shown, the material exited from the distal end 1008 of tube 1002. Optionally, a stop is provided at the end, so that the material is forced sideways. Optionally, the stop is not attached to tube 1002 at end 1008 thereof. Rather a thread, running through tube 1002 and/or outside thereof (or more than one thread) attaches the stop to the body of device 1000. Optionally, the thread runs through a narrow lumen formed in pusher 1004.

Alternatively, one or more elements which attach the stop to tube 1002, serve to split sleeve 1010, at tip 1008 of tube 1002. In an exemplary embodiment of the invention, the stop is attached to tube 1002 after the sleeve is mounted thereon. Alternatively, the sleeve is pre-split, pulled through tube 1002, past the elements and attached to connector 1019.

In an alternative embodiment of the invention, the sleeve is provided totally within the delivery tube. In one embodiment (not shown), the delivery tube comprises two coaxial tubes and the inner tube serves as shown by tube 1002 in FIGS. 10A-10E.

In another embodiment, the fact that the delivery tube is full of material is taken advantage of, in that the material (316) serves to prevent the tube from collapsing when it is simultaneously pushed from one end and pulled from the other. This may depend on the viscosity of the material and/or on the shape of the distal tip of the delivery system. Optionally, the distal end is slightly flared to define a folding over location for the sleeve.

Figure 10F:
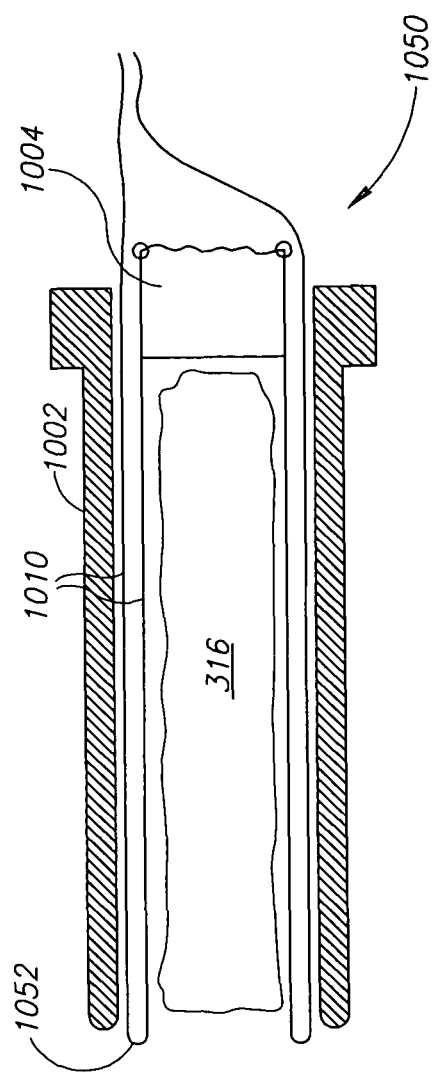

FIG. 10F shows such an embodiment, of a delivery system 1050, in which sleeve 1010 is provided within delivery tube 1002. As can be seen a folding over location 1052 for the sleeve is provided past the end of tube 1002. In an exemplary embodiment of the invention, a ring (not shown) is provided past the end of tube 1002 and around which the sleeve is folded. This ring serves as a scaffold for the folding, but due to its having a diameter greater than an inner diameter of tube 1002 (or at least being misaligned if the ring and/or tube are not circular in cross-section), cannot be pulled into the tube by retraction of sleeve 1010.

In an alternative embodiment of the invention, sleeve 1010 does not fold back towards system 1000. Rather, the sleeve is pushed into the vertebra with the material. Optionally, once out of the confines of tube 1002, the material can tear the tube. In an alternative embodiment, the sleeve remains intact and encloses the material, sausage-like, in the body. The sleeve may be formed of biocompatible, bioabsorbable and/or implant grade material.

Squeeze Based Material Provision

Figure 11A:
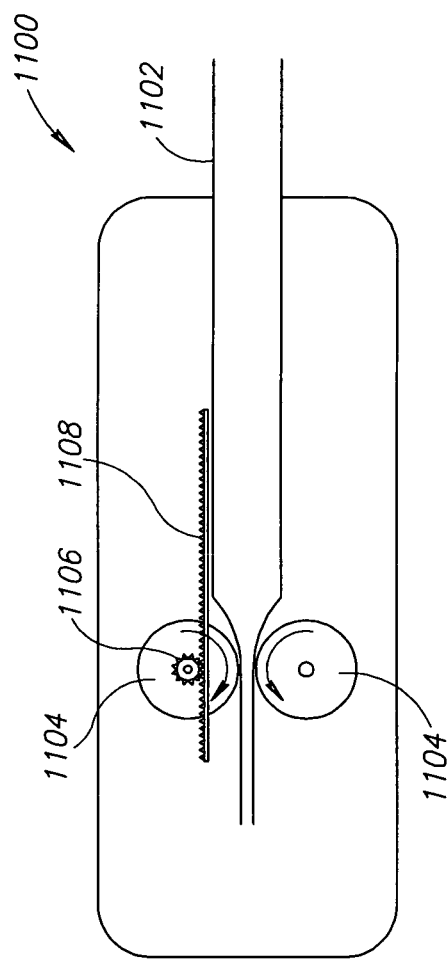
FIGS. 11A and 11B show squeeze based delivery systems, in accordance with exemplary embodiments of the invention.

In an exemplary embodiment of the invention, the material is squeezed out of the delivery system rather than pushed. FIG. 11A shows a squeeze based system 1100, in which a delivery tube 1102 is made out of a squeezable material, such as a polymer or annealed metal. A pair of rollers 1104 (or one roller and an opposing anvil, not shown) advance towards the distal side of tube 1102, squeezing it flat and forcing material that fills the tube to migrate distally. Various motion mechanism can be used. In the figure, the motion mechanism is a linear gear 1108 which engages a gear 1106 that is coaxial with roller 1104. When the roller is rotated, the linear gear advances the roller. Various power sources may be used, for example, electric motors and hydraulic power. Also, other power trains may be used. The rollers are optionally made of stainless steel.

Figure 11B:
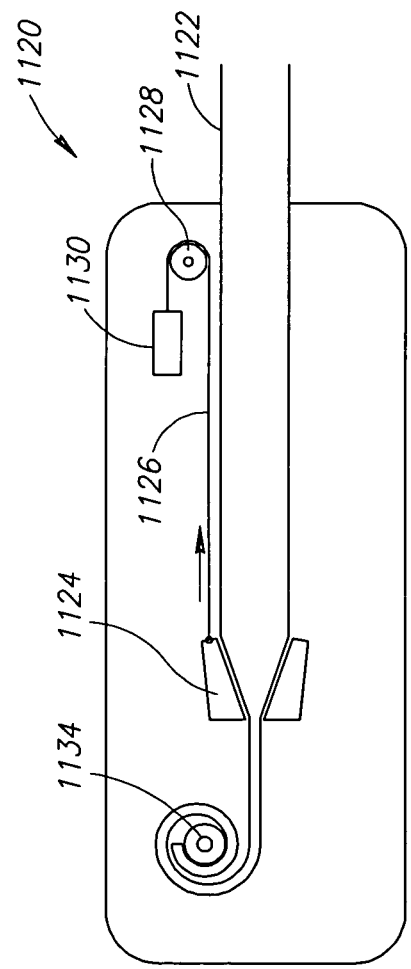

FIG. 11B shows a delivery system 1120, in which a squeeze element 1124 slides rather than rolls against a delivery tube 1122. Tube 1122 is optionally rolled around a pin 1134. Various mechanisms can be used to move squeeze element 1124, for example a motor 1130 attached to a cable 1126 via an optional pulley 1128.

Tamping Method

In an exemplary embodiment of the invention, friction is reduced by reducing the length of motion of the material inside a delivery tube. In one method, a small amount of material is provided into a distal side of a delivery tube (while outside the body). Then the distal part is inserted into the body and a tamping tool is provided into the proximal part.

This process may be repeated several times until a desired amount of material is provided into the body.

Penetrating Delivery System

In some embodiment of the invention, the delivery system also penetrates to the bone and/or penetrates the bone. Optionally, this obviates the need for a separate cannula and/or may simplify the procedure. Optionally, the delivery tube is kept in the body when it is being refilled with material to be injected.

Figure 12A:
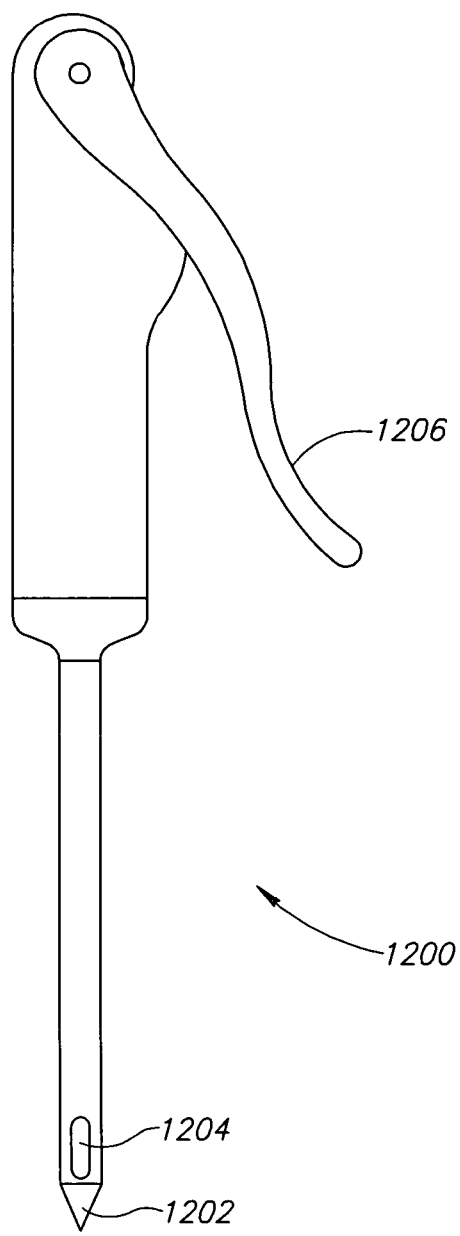
FIGS. 12A, 12B, and 12D illustrate a one step access and delivery system, in accordance with an exemplary embodiment of the invention.
Figure 12B:
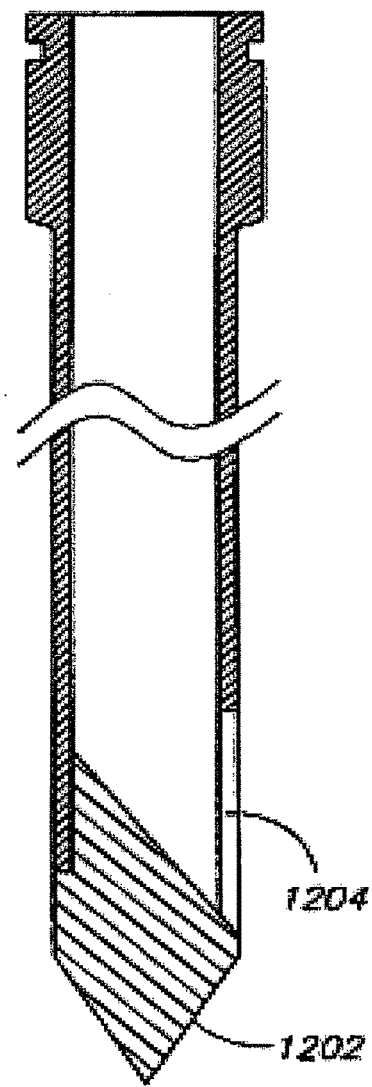
Figure 12D:
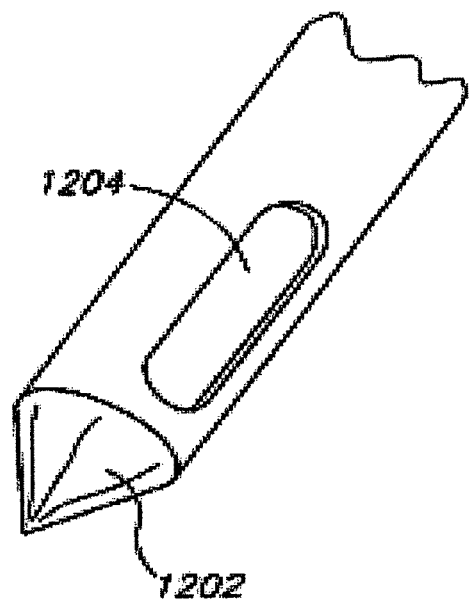

FIG. 12A shows a penetrating delivery system 1200. A distal tip 1202 is formed in a manner suitable for drilling in bone. This is shown in greater detail in FIGS. 12B and 12D.

A hydraulic pump or mechanical ratchet advance mechanism is optionally used, with a handle 1206 used for pumping shown.

A potential advantage of a one piece system is that fewer parts are needed. If the system is preloaded with all the material needed, for example, at a manufacture, no equipment changes are needed. Optionally, the use of a side aperture 1204 allows the tip to be a drilling tip. Optionally, the use of smaller diameter tubes allows fewer parts to be used, as drilling is simplified.

Optionally, the proximal end of system 1200 is adapted for tapping with a mallet.

Figure 12C:
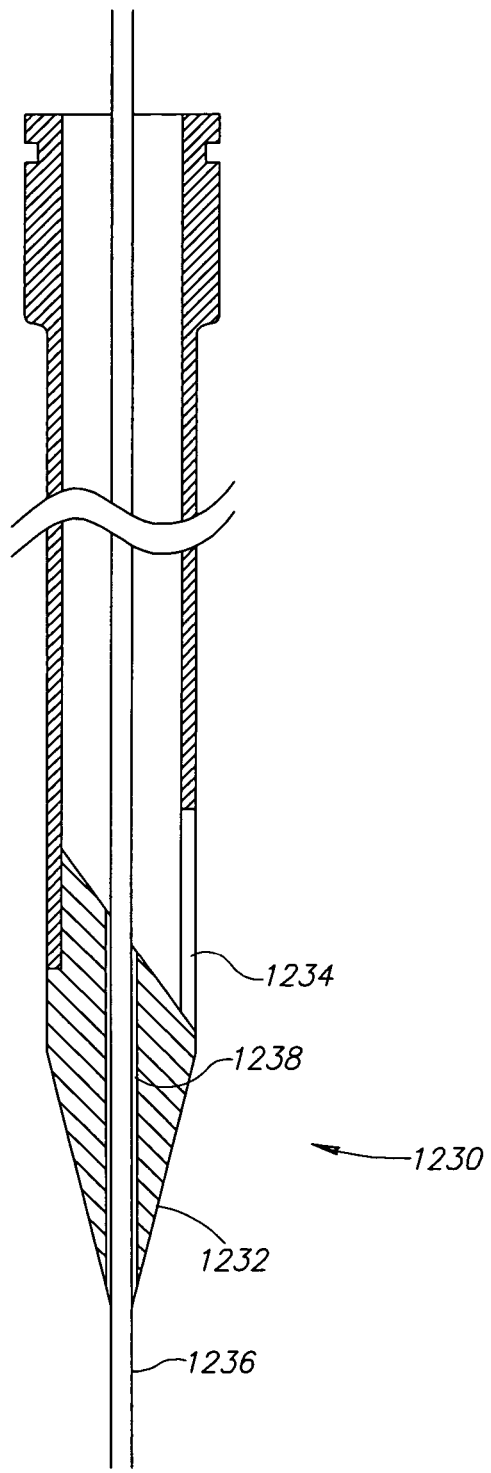
FIG. 12C shows an over-the-wire delivery system, in accordance with an exemplary embodiment of the invention.

FIG. 12C shows an alternative embodiment of a system, 1230, in which the system is adapted to ride on a guidewire 1236, for example, a K-wire. In an exemplary embodiment of the invention, a bore 1238 is formed in a drilling section 1232 of system 1230. Alternatively, the bore is to the side of the drilling head, for example, exiting through an aperture 1234 which may also be used for extruding material. Optionally, the pusher (not shown) is drilled as well. Optionally, the diameters of the drilled holes are too small for the material to exit through. Alternatively, bore 1238 is used for extruding material, after the K-wire is removed.

In an exemplary embodiment of the invention, the material is predrilled with a bore, to allow passage of the guidewire therethrough. Optionally, this bore is provided with a sleeve. It is noted that absent axial pressure on the material, the material will generally not flow into the drilled bore. Alternatively or additionally, the guidewire is coated with a suitable friction reducing coating, solid or fluid.

Optionally, the delivery tube is loaded after the delivery tube is guided into the body (and the guidewire removed), for example using a barrel storage means or a unit magazine as described above.

Optionally, a separate lumen is defined for a K-wire. Optionally, that lumen is a collapsible lumen. However, until pressure is applied to the material to be delivered, it remains un-collapsed. Once the guidewire completed its task, it is removed and pressure applied to the material, collapsing the guidewire channel and improving the flow characteristics (by increasing effective inner diameter of the delivery tube.

In an exemplary embodiment of the invention, a cannula is not needed, for example, if the delivery system rides on the guidewire or if the delivery system is used to directly penetrate the bone. Optionally, the delivery tube of the delivery system is not removed once inserted into or to the bone, for example, using a barrel or pumping mechanism as described above to reload the delivery mechanism if required. Once the system is reloaded, the pusher can advance the material into the delivery tube where it can then be advanced into the bone.

Optional Additional Therapy

In an exemplary embodiment of the invention, the provision of material is enhanced by additional therapy. Optionally, the additional therapy comprises thermal therapy. Optionally, the material is pre-heated or pre-cooled. Optionally, the pre-heating or pre-cooling also serves a purpose of controlling the material properties and/or setting behavior.

In an exemplary embodiment of the invention, the heating is by contact heat (conduction) or by light, for example a flash lamp or a laser source. Alternatively or additionally, the delivery system radiates heat. Optionally, a microwave or other wireless heating method is used.

Optionally, heating is provided separately from material provision. In one example, a heated guidewire is provided into the vertebra. Optionally, the guidewire extends one or more protrusions, to guide thermal energy into the nearby tissue. Optionally, a thermal sensor is provided to control the temperature in the vertebra and/or prevent over heating.

Exemplary Materials

Various materials are suitable for use with exemplary embodiments of the invention. Some of the materials which can be used in some embodiments of the invention are known materials, for example, PMMA, however, they may be used at unusual conditions, for example at a semi-hardened condition. Also, while putty materials may be known, they are not typically used for injection through a small bore into bone.

It should be noted that while specific examples are described it is often the case that the material composition will be varied to achieve particular desired mechanical properties. For example, different diagnoses may suggest different material viscosities.

In an exemplary embodiment of the invention, for non-hardening materials, the material can be allowed to set outside the body. After such setting the material may be washed or ventilated. In this manner, some materials with potentially hazardous by-products can be safely mixed and then used in the body. Optionally, a material is tested to make sure toxic byproducts are removed to below a safety threshold. Optionally, a testing kit is provided with the delivery system.

In an exemplary embodiment of the invention, the material is selected so that its mechanical properties match the bone in which it will be implanted. In an exemplary embodiment of the invention, the material is matched to healthy or to osteoporostic trabecular bone. Optionally, the mechanical properties of the bone are measured during access, for example, based on a resistance to advance or using sensors provided through the cannula or by taking samples, or based on x-ray densitometers measurements.

In general, PMMA is stronger and has a higher modulus than trabecular bone. For example, Trabecular bone can have a strength of between 3-20 megapascal and a Young modulous of 100-500 megapascal. Cortical bone, for example, has strength values of 170-190 gigapascal and Young modulus of 13-40 gigapascal. PMMA typically has values about half of Cortical bone.

In an exemplary embodiment of the invention, the material is selected to be less than 120% as strong and/or young modulus as the expected bone to be treated. Optionally, the values of one or both of strength and young modulus are 10%, 20%, 30%, 40% or less reduced from that of trabecular bone. It should be noted that if less of the vertebra is filled, the injected material will be supported, at least in part, by trabecular rather than cortical bone, depending for example on the method of filing of interior 308.

Exemplary Non-Hardening Material

In an exemplary embodiment of the invention, the material used is a putty like material. One example of a putty-like material is a hydroxyapatite with an increased ratio of sodium alginate. For example, the increased ratio can be 8% or 10%. While this material does harden in the body, it does not set to a hardened condition absent humidity. Thus it can be prepared ahead of time and pre-stored in a delivery system, for example by a manufacturer. In an exemplary embodiment of the invention, the added material slows down water absorption so that while sufficient water enters the material to initiate setting, not enough enters to cause dissolution. An example of this material is described in Ishikawa et al., "Non-decay fast setting Calcium phosphate cement: Hydroxyapatite putty containing an increased amount of sodium alginate", J Biomed Mater Res 36 1997, 393-399, the disclosure of which is incorporated herein by reference. More details may be found in "Effects of neutral sodium hydrogen phosphate on setting reaction and mechanical strength of hydroxyapatite putty", by Kunio Ishikawa, Youji Miyamoto, Masaaki Takechi, Yoshiya Ueyama, Kazuomi Suzuki, Masaru Nagayama and Tomohiro Matsumura, in J Biomed Mater Res, 44, 322-329, 1999, the disclosure of which is incorporated herein by reference.

Other calcium derivative cements, bone chips and/or fillers may be used as well. Bone chips, depending on processing may have a limited shelf life. Some of these materials generally harden (or combine with bone growth) after a relatively long time, such as more than a week, more than a month or more than 3 months.

Additional Exemplary Non-Hardening Material

Figure 13:
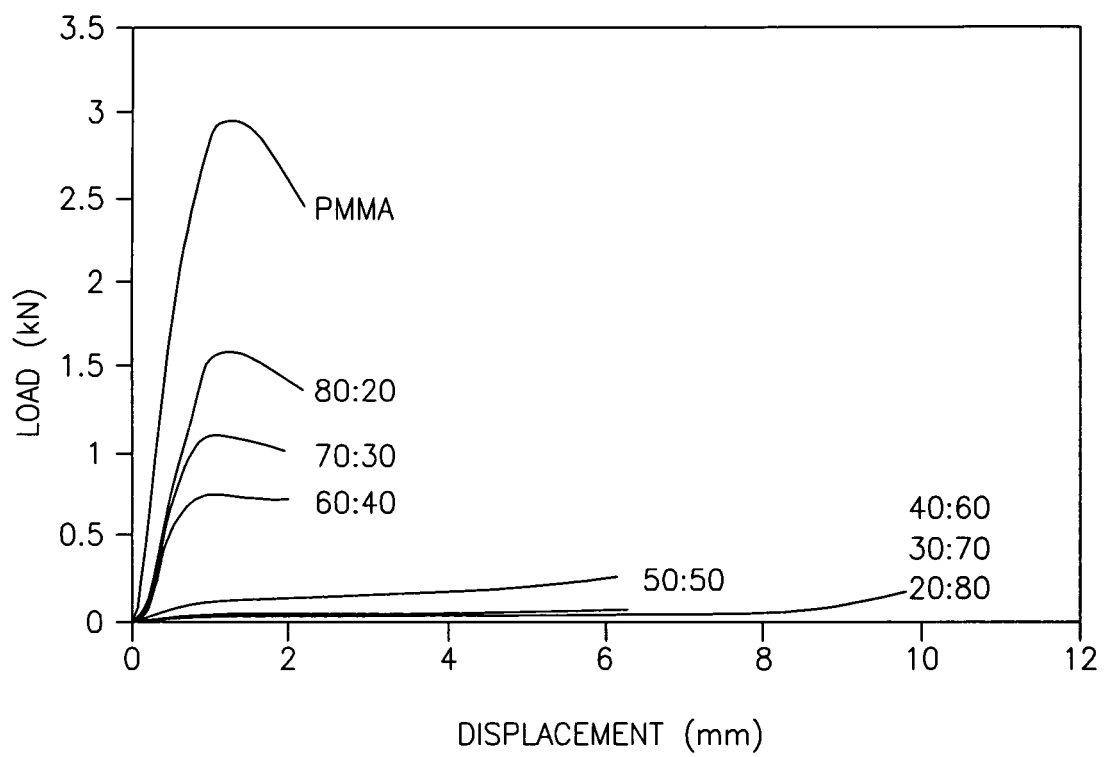
FIG. 13 is a graph showing compressibility of a material in accordance with an exemplary embodiment of the invention.

In an exemplary embodiment of the invention, the material used is a mixture of LMA (lauryl methacrylate) and MMA (methyl methacrylate). Depending on the ratio used, different mechanical properties and viscosities can be achieved. FIG. 13 is a graph showing the relative viscosities of PMMA and various ratios of the copolymer material. In the example shown, as the ratio of LCA decreases, viscosity goes down.

Diblock copolymers of MMA and LMA were synthesized by anionic polymerization using DPHLi as initiator in THF at −40° C. with the sequential addition of monomers. The molecular weight distribution of the polymers was narrow and without homopolymer contamination when LMA was added to living PMMA chain ends.

In an exemplary embodiment of the invention, the ratio used are 80:20, 70:30, 60:40, 50:50, 30:70, 20:80 or intermediate, smaller or larger ratios (by volume).

Experiment: Materials and Methods
Starting Materials

Medicinal distillate methyl methacrylate and lauryl methacrylate stabilized with 10-100 ppm of the monomethyl ether of hydroquinone were used as received from Fluka, Germany. Benzoyl peroxide (BPO) was purchased from BDH Chemicals, England. N Barium sulfate (BS) was obtained from Sigma-Aldrich (Israel). All solvents were analytical-grade from Biolab (Jerusalem, Israel) and were used as received.

Polymerization

Polymerization reactions were carried out in a single necked round bottom flask equipped with a magnetic stirring. In a typical reaction, 60 ml MMA (0.565 mol), 50 ml LMA (0.137 mol), 220 mg of Benzoyl Peroxide (0.9 mmol), and 100 ml THF were transferred. The amount of BPO was adjusted to each of the compositions according to the total amount of the monomer's mols. The amount of the THF was equal to the total volume of the monomers (table 1). The content was heated to a polymerization temperature of 70-75° C. for 20 hours, then the solution was precipitated in sufficient amount of methanol and left to mix for four hours. Finally, the polymer was dried in an oven at 110° C. under vacuum.

TABLE 1 copolymers composition

| Copolymer (MA:LMA) | MA (ml/mol) | LMA (ml/mol) | BPO (mg/mol) | THF (ml) |
| --- | --- | --- | --- | --- |
| 100:0 | 100(0.94) | 0(0) | 285(1.18) | 100 |
| 80:20 | 80(0.75) | 20(0.07) | 258(1.06) | 100 |
| 70:30 | 70(0.66) | 30(0.10) | 239(0.99) | 100 |
| 60:40 | 60(0.56) | 40(0.14) | 220(0.9) | 100 |
| 50:50 | 50(0.47) | 50(0.17) | 201(0.83) | 100 |
| 40:60 | 40(0.38) | 60(0.20) | 182(0.75) | 100 |
| 30:70 | 30(0.28) | 70(0.24) | 163(0.67) | 100 |
| 20:80 | 20(0.19) | 80(0.27) | 144(0.6) | 100 |
| 0:100 | 0(0) | 100(0.34) | 107(0.44) | 100 |

The dried polymer was milled to a fine powder (Hsiangtai Sample mill, model sm-1, Taiwan) and mixed with barium sulfate (30% w/w). The mixture was heated in a glass inside a sand bath to 140° C., until melting of the polymer. The mixture left to cool, and milled again. This procedure was repeated at least three times, until a homogeneous off-white polymer was received, which could be melted into loadable slugs for the delivery systems and magazines described above.

Characterization

Molecular weight and polydispersity were analyzed by Gel permeation chromatography, GPC system consisting of a Waters 1515 isocratic HPLC pump with a Waters 2410 refractive-index detector and a Rheodyne (Coatati, Calif.) injection valve with a 20-μL loop (Waters Ma). The samples were eluted with $CHCl_3$ through a linear Ultrastyragel column (Waters; 500-Å pore size) at a flow rate of 1 mL/min.

$^1$H—NMR spectra were recorded on a Varian 300 MHz instrument using $CDCl_3$, as solvents. Values were recorded as ppm relative to internal standard (TMS).

A Cannon 1C A718 Ubbelhold viscometer was used for the viscosity measurements of the polymer. The measurements were performed at 30° C. with toluene as a solvent.

Water Absorption Capacity

Swelling behavior of acrylic bone cements was carried out from accurately weighed films of 0.8 mm thickness. Films were introduced in 0.9 wt % NaCl solution (20 ml) and kept at 37° C. The water sorption kinetics in 20 ml saline solution were evaluated in two specimens of each bone cement (containing 30% barium sulphate).

Equilibrium gain was determined gravimetrically at different periods of time. The uptake of water was recorded at 30 min intervals in the beginning and spacing out these intervals until the equilibrium was attained. At appropriate times, the samples were removed, blotted with absorbent paper to remove the water attached on its surface and weighed. The percentage of Equilibrium gain was obtained from each specimen using the following expression:

$$\text{Hydration degree}(\%) = \frac{\text{Weight of swollen specimen} - \text{initial weight of specimen}}{\text{initial weight of specimen}} \times 100$$

Results:
  100% PMMA: Average 1.845% (+0.045)
  Initial weight (g) 0.2156 and 0.2211
  Weight of specimen at equilibrium (g) 0.2195 and 0.2253
  Equilibrium gain (%): 1.8 and 1.89;
  60% PMMA, 40% PLMA: Average 1.65% (+0.235)
  Initial weight (g): 0.1161 and 0.1402
  Weight of specimen at equilibrium (g) 0.1183 and 0.1422
  Equilibrium gain (%): 1.42 and 1.89;
  50% PMMA, 50% PLMA: Average: 1.02% (+0.28)
  Initial weight (g): 2700 and 0.2371
  Weight of specimen at equilibrium (g) 0.2720 and 0.2400
  Equilibrium gain (%): 0.74 and 1.3;

Compression Testing

These tests were conducted using an Instron 4301 universal testing machine provided with a load cell of 5 kN, and at a cross-head speed of 20 mm/min. A known weight of polymer was melted in a glass inside a sand bath. The bath was heated at 150° C. for two hours, and then barium sulfate was added (30% w/w) and mixed well several times, until homogenous dough was received. Cylindrical specimens of 6 mm in diameter and 12 mm high were prepared by forcing the melted copolymers into the holes of a Teflon mold. One side of the mold was covered with Teflon plates and secured with clamps. The specimens were cooled for 20 minutes in the mold, then the upper side was cut to the mold shape, and the specimens removed from the mold, finished to a perfect cylindrical shape. The test took place at least 1 week after aging in air at 23±1° C. For each cement composition, six specimens were tested.

The elastic modulus and the maximal strength force were obtained.

Results:

Molecular Weights and Viscosity Measurement

The number and weight average molecular weights of poly(La-MA), poly(MMA) and their copolymers were obtained from gel permeation chromatography. The polydispersity index varies in the range of 1.6 to 2.87. The viscosities of the polymers are obtained using Toluene as solvent at 25° C. The intrinsic viscosities (η) were obtained by extrapolating $\eta_{sp\ c}^{-1}$ to zero concentration. The molecular weights and viscosities are presented in Table II.

TABLE II composition

| Feed Ratio | | GPC analysis of polymers | | | |
|---|---|---|---|---|---|
| MMA:LMA Vol.-% (mol-%) | NMR Analysis [MMA]:[LMA] | $M_n$ | $M_w$ | Polydispersity | [η] |
| 100:0 (100:0) | 100:0 | 65190 | 119544 | 1.833 | 0.544 |
| 8:2 (91.5:8.5) | [88]:[12] | 69118 | 119194 | 1.724 | 0.421 |
| 7:3 (87:13) | 87:13 | 63006 | 112442 | 1.78 | 0.393 |
| 6:4 (84:16) | 84:16 | 73295 | 118384 | 1.615 | 0.366 |
| 1:1 (74:26) | 69:31 | 94167 | 135880 | 1.44 | 0.351 |
| 4:5 (69:31) | 70:30 | 55455 | 104711 | 1.888 | 0.316 |
| 4:6 (64:36) | 62:38 | 75648 | 134745 | 1.781 | 0.305 |
| 3:7 (56:44) | 56:44 | 35103 | 79986 | 2.27 | 0.221 |
| 2:8 (40:60) | 40:60 | 23876 | 68720 | 2.87 | 0.178 |
| 0:100 (0:100) | 0:100 | 27350 | 75146 | 2.74 | 0.083 |

Compressive Test

The results of the compressive test are collected in Table III as a function of compressive strength and modulus. The influence on the mechanical behavior of adding lauryl methacrylate monomers can be clearly observed. The introduction of higher percentages produces a decrease that is more pronounced at 50% (v/v) LA. The compressive modulus shows a drastic decrease as the content of LA increases. This drop may be related to the structure modification of the matrix by the introduction of LMA. This drop may also limit the use of some compositions for some applications.

TABLE III compression test results

| Composition MA:LA (V %) | Max strength (Mpa) | Modulus (Mpa) |
|---|---|---|
| 1:0 | 106.8(9) | 2478(220) |
| 8:2 | 82.5(17.1) | 1100.7(129) |
| 7:3 | 63.3(13.2) | 634.5(116) |
| 6:4 | 48(11) | 550(250) |
| 5:5 | 18.9(4.5) | 69.6(20) |
| 4:6 | 1.9(0.2) | 49.5(11.8) |
| 3:7 | 19.19(3.42) | 8.3(1.2) |
| 2:8 | 0.253(0.06) | 1.71(0.417) |

Material Modifications

Optionally, various additives are added to the materials described herein, to modify their properties. The adding can be before setting or after setting, depending on the material. Exemplary materials that can be added include fibers (e.g., carbon nanotubes or glass fibers) of various lengths and thicknesses, aggregates and/or air bubbles.

In an exemplary embodiment of the invention, if the material is manufactured to be anisotropic, it can be advanced into the body in a desired direction, for example, by selecting a delivery path (e.g., storage, tube, aperture) to reduce twisting and/or deformation. Optionally, such materials are provided as short units (FIG. 8).

Softening and Semi-Hardening Materials

In an exemplary embodiment of the invention, the material used softens after provision into the body. In an exemplary embodiment of the invention, the material comprises an additive that disperses or weakness in water or body fluids, for example, salt. A softening material may be useful if the forces required for height restoration are smaller than the forces required for maintaining height. Softening times are optionally controlled by mixing in a gel material which slows down water penetration into the extruded material.

Semi-Hardening Materials

In an exemplary embodiment of the invention, the material used sets to non-hardened condition. In an exemplary embodiment of the invention, the material comprises MMA, LMA and NMP. NMP solvates in water, allowing the material to set somewhat. In an exemplary embodiment of the invention, a hardened condition is avoided, possibly preventing the induction of fractures in nearby vertebra.

Use of Hardening Materials

In an exemplary embodiment of the invention, the above described devices (e.g., delivery) are used with a material which sets to a hardened condition, for example, PMMA or other bone cements and fillers. In an exemplary embodiment of the invention, the material is provided in a kit that includes a timer and/or a viscometer, so that an operator can estimate the workability and viscosity of the material and its usefulness for height restoration without leakage. Optionally, the time includes a temperature senor and provides an estimate of workability time based on the temperature and the time the components of the PMMA were mixed.

In an exemplary embodiment of the invention, a setting material is formulated to have a high viscosity for a working window of significant duration, for example, 2, 4, 5, 8, 10 or intermediate or more minutes.

In an exemplary embodiment of the invention, the following formulation is used: a set of beads formed of PMMA/Styrene of diameter 10-200 microns and an amount of 20 cc MMA per 9.2 grams beads. In an exemplary embodiment of the invention, MMA solvates and/or encapsulates the beads and the viscosity of the mixture remains high, at the beginning due to the solvation and friction between the beads and later, as the beads dissolve, due to the progressing of polymerization. The beads may also be provided in a mixture comprising a range of sizes. It should be noted that the properties of the materials may be selected to improve a viscosity working window, even if strength of the final cement is compromised.

In an exemplary embodiment of the invention, the working viscosity is set by selecting the bead size and/or material ratios.

Additional Implant Devices

Optionally, an implant is also injected into the vertebra, for example, before, during or after injection of the material. Exemplary implants are metal or polymer cage or intra ventricular devices and enclosing mesh or solid bags or balloons. Optionally, bone graft is injected. Optionally, where an implant is provided, the material is extruded through the implant, for example from an axial section thereof in a radial direction.

Optionally, devices such as described in PCT applications PCT/IL00/00458; PCT/IL00/00058; PCT/IL00/00056; PCT/IL00/00055; PCT/IL00/00471; PCT/IL02/00077; PCT/IL03/00052; and PCT/IL2004/000508, PCT/IL2004/000527 and PCT/IL2004/000923, the disclosures of which are incorporated herein by reference, are used.

Optionally, the material is extruded into a performed cavity, for example a cavity formed using an inflatable balloon. Optionally, the material is extruded into an intervertebral space, for example a disc-space.

Optionally, a material which sets to a hardened condition, for example, PMMA is co-extruded with or extruded before or after material which does not so set. Optionally, the setting material comprises less than 60% of the material, for example, less than 40%, less than 20% or intermediate values.

Other Tissue and General

While the above application has focused on the spine, other tissue can be treated as well, for example, compacted tibia plate and other bones with compression fractures and for tightening implants, for example, hip implants or other bone implants that loosened, or during implantation. Optionally, for tightening an existing implant, a small hole is drilled to a location where there is a void in the bone and material is extruded into the void.

It should be noted that while the use in bones of the above methods and devices provide particular advantages for bone and vertebras in particular, optionally, non-bone tissue is treated, for example, cartilage or soft tissue in need of tightening. Optionally, the delivered material includes an encapsulated pharmaceutical and is used as a matrix to slowly release the pharmaceutical over time. Optionally, this is used as a means to provide anti-arthritis drugs to a joint, but forming a void and implanting an eluting material near the joint.

It will be appreciated that the above described methods of implanting and treating may be varied in many ways, including, changing the order of steps, which steps are performed more often and which less often, the arrangement of elements, the type and magnitude of forces applied and/or the particular shapes used. In particular, various tradeoffs may be desirable, for example, between applied forces, degree of resistance and forces that can be withstood. Further, the location of various elements may be switched, without exceeding the spirit of the disclosure, for example, the location of the power source. In addition, a multiplicity of various features, both of method and of devices have been described. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. In addition, some of the features of the invention described herein may be adapted for use with prior art devices, in accordance with other exemplary embodiments of the invention. The particular geometric forms used to illustrate the invention should not be considered limiting the invention in its broadest aspect to only those forms, for example, where a cylindrical tube is shown, in other embodiments a rectangular tube may be used. Although some limitations are described only as method or apparatus limitations, the scope of the invention also includes apparatus programmed and/or designed to carry out the methods.

Also within the scope of the invention are surgical kits which include sets of medical devices suitable for implanting a device or material and such a device. Section headers are provided only to assist in navigating the application and should not be construed as necessarily limiting the contents described in a certain section, to that section. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A composite tool for accessing bone, comprising:
    an elongate body, having:
        a head having a distal tip configured to penetrate bone, the head being disposed on a distal end of the elongate body;
        at least one aperture formed in a sidewall of the elongate body proximal to the distal end and being configured to extrude material radially therethrough and into bone;
        a lumen adapted to deliver material to the aperture; and
        a guidewire channel formed within at least a portion of the elongate body;
    wherein the guidewire channel is collapsible in response to pressurizing material to be delivered through the lumen.

2. The tool according to claim 1, further comprising a source of material under pressure coupled to a proximal portion of the elongate body for delivering the material into the lumen.

3. The tool according to claim 2, wherein the source of material is a hydraulic source.

4. The tool according to claim 2, wherein the material comprises at least one material adapted to function in a capacity other than as a structural support.

5. The tool according to claim 1, wherein the elongate body and the head are integrally formed.

6. The tool according to claim 2, wherein the pressure is at least 40 atmospheres.

7. The tool according to claim 2, wherein the pressure is at least 100 atmospheres.

8. The tool according to claim 1, wherein the elongate body comprises a plurality of extrusion apertures formed in a sidewall thereof adapted to extrude material into bone.

9. The tool according to claim 2, wherein the material comprises PMMA bone cement.

10. The tool according to claim 9, wherein when the material is delivered into the lumen of the elongate body, the material has a viscosity between 600 and 1800 Pascal-seconds for at least 5 minutes.

11. The tool according to claim 1, further comprising a source of material under pressure coupled to a proximal portion of the elongate body, the material comprising PMMA bone cement.

12. The tool according to claim 11, wherein when the material is delivered into the lumen of the elongate body, the material has a viscosity between 600 and 1800 Pascal-seconds for at least 5 minutes.

* * * * *